US010926081B2

(12) United States Patent
Sibary et al.

(10) Patent No.: US 10,926,081 B2
(45) Date of Patent: Feb. 23, 2021

(54) IMPLANTABLE STIMULATING ASSEMBLY

(71) Applicant: Cochlear Limited, Macquarie University (AU)

(72) Inventors: Peter Raymond Sibary, Macquarie University (AU); Nicholas Charles Pawsey, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 710 days.

(21) Appl. No.: 15/249,799

(22) Filed: Aug. 29, 2016

(65) Prior Publication Data
US 2017/0056646 A1    Mar. 2, 2017

Related U.S. Application Data

(60) Provisional application No. 62/211,434, filed on Aug. 28, 2015.

(51) Int. Cl.
*A61N 1/37* (2006.01)
*A61N 1/05* (2006.01)
*A61N 1/378* (2006.01)
*A61N 1/36* (2006.01)

(52) U.S. Cl.
CPC ......... *A61N 1/0541* (2013.01); *A61N 1/3787* (2013.01); *A61N 1/36038* (2017.08)

(58) Field of Classification Search
CPC ............. A61N 1/0541; A61N 1/36036; A61N 1/3787
See application file for complete search history.

(56) References Cited

U.S. PATENT DOCUMENTS

| 4,488,561 A | 12/1984 | Doring |
| 6,730,015 B2 | 5/2004 | Schugt et al. |
| 7,006,875 B1 | 2/2006 | Kuzma et al. |
| 8,126,564 B2 | 2/2012 | Gantz |
| 8,812,121 B2 | 8/2014 | Risi et al. |
| 9,522,268 B2 * | 12/2016 | Dhanasingh ......... A61N 1/0541 |
| 2003/0009095 A1 | 1/2003 | Skarda |
| 2003/0093139 A1 | 5/2003 | Gibson et al. |
| 2004/0220651 A1 | 11/2004 | Kuzma et al. |

(Continued)

FOREIGN PATENT DOCUMENTS

EP    0818123 B1    1/2003

OTHER PUBLICATIONS

International Search Report and Written Opinion for PCT/IB2016/055161, dated Dec. 8, 2016.

(Continued)

*Primary Examiner* — Rex R Holmes
(74) *Attorney, Agent, or Firm* — Piloff Passino & Cosenza LLP; Martin J. Cosenza

(57) ABSTRACT

An elongate stimulation assembly of an implantable stimulation device, including an intra-cochlear portion including an array of electrodes, and an extra-cochlear portion extending from the intra-cochlear portion, wherein the extra-cochlear portion includes a plurality of electrical lead wires in electrical communication with the array of electrodes and a malleable component extending in an elongate manner such that the malleable component is located further away from a longitudinal axis of the extra-cochlear portion than at least one of the electrical leads of the plurality of electrical leads.

32 Claims, 46 Drawing Sheets

(56) References Cited

U.S. PATENT DOCUMENTS

| | | |
|---|---|---|
| 2009/0088651 A1 | 4/2009 | Shuros et al. |
| 2011/0034969 A1* | 2/2011 | Capcelea ............. A61N 1/0541 607/57 |
| 2011/0040364 A1 | 2/2011 | Dadd et al. |
| 2011/0295352 A1 | 12/2011 | Thenuwara et al. |
| 2011/0319907 A1 | 12/2011 | Gallegos et al. |
| 2014/0214145 A1 | 7/2014 | Zimmerling et al. |
| 2015/0157852 A1 | 6/2015 | Jolly et al. |
| 2015/0202423 A1 | 7/2015 | Adenusi et al. |

OTHER PUBLICATIONS

Extended European Search Report for EP Application No. 16 840 932.4, dated Jul. 19, 2019.

* cited by examiner

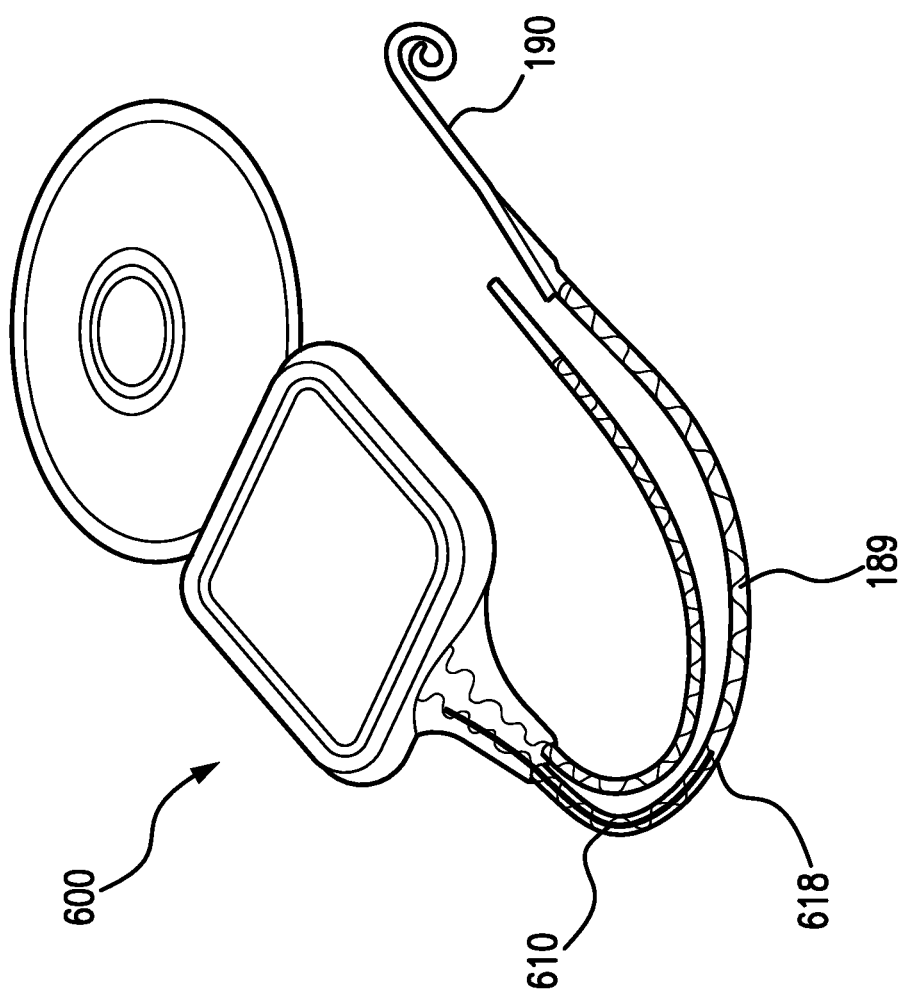

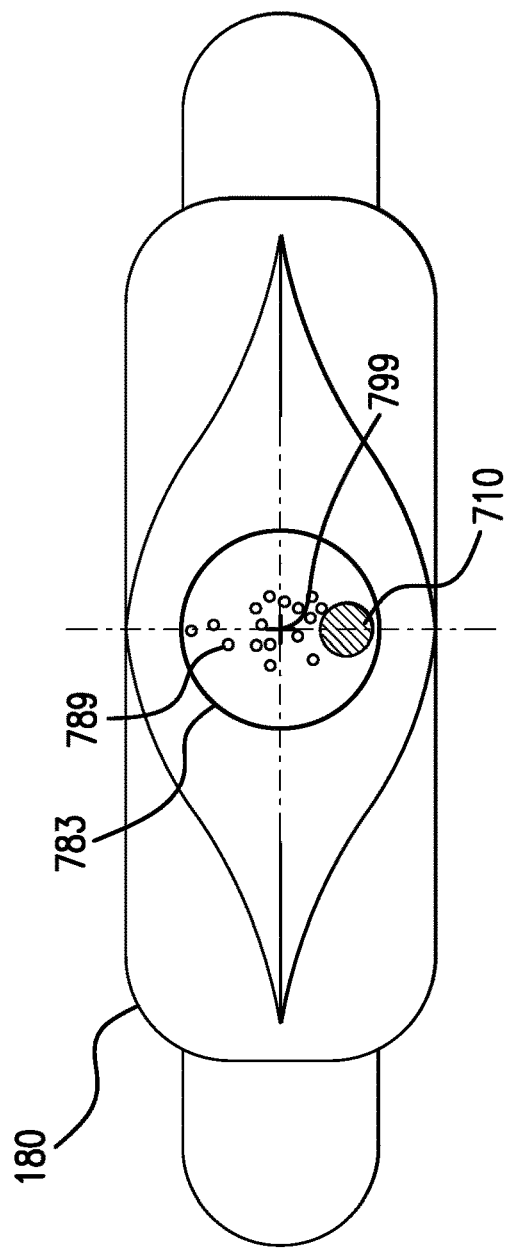
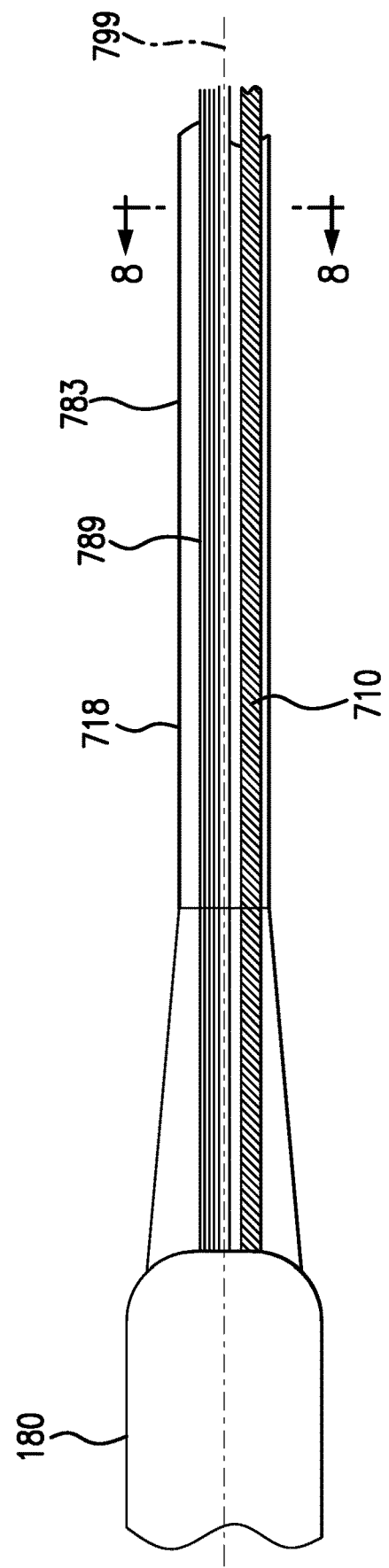
FIG. 8
FIG. 7

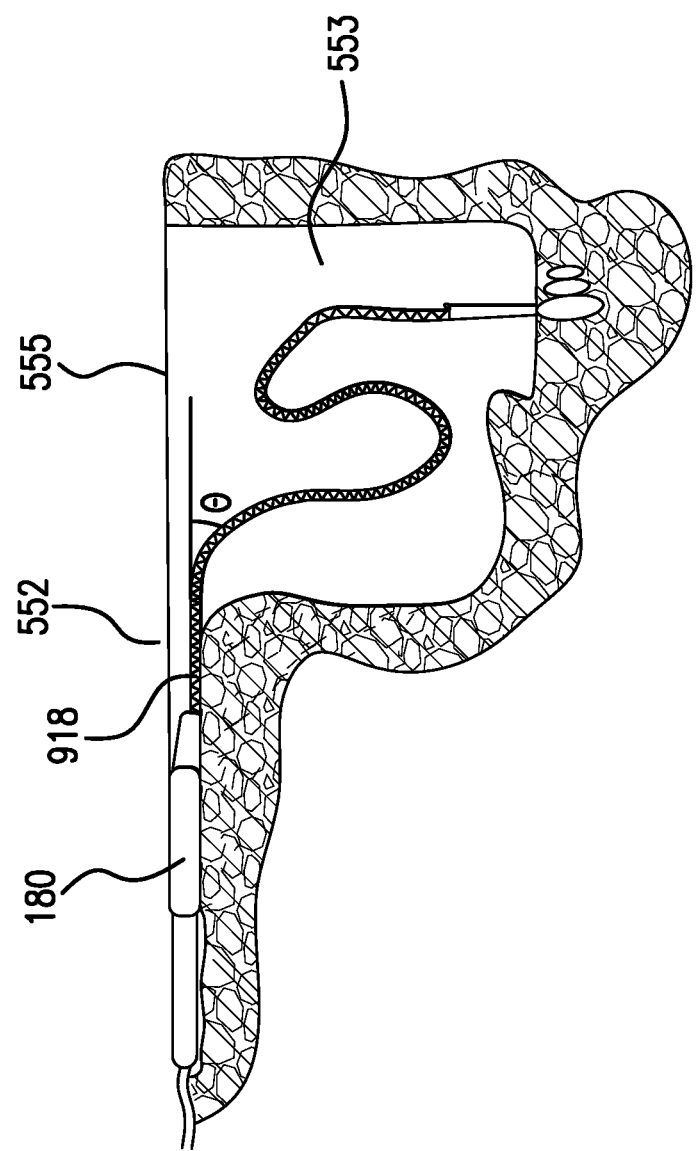

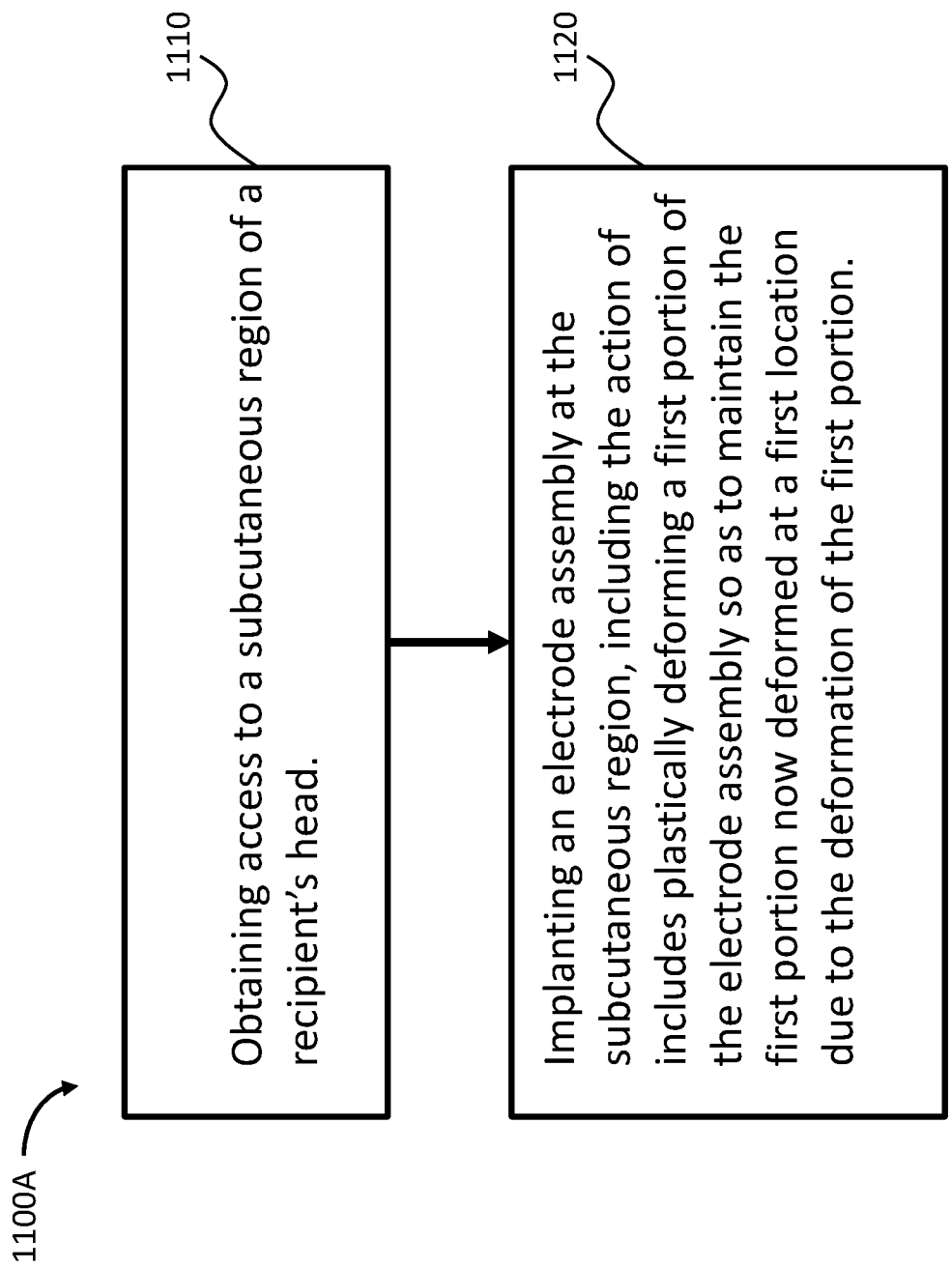

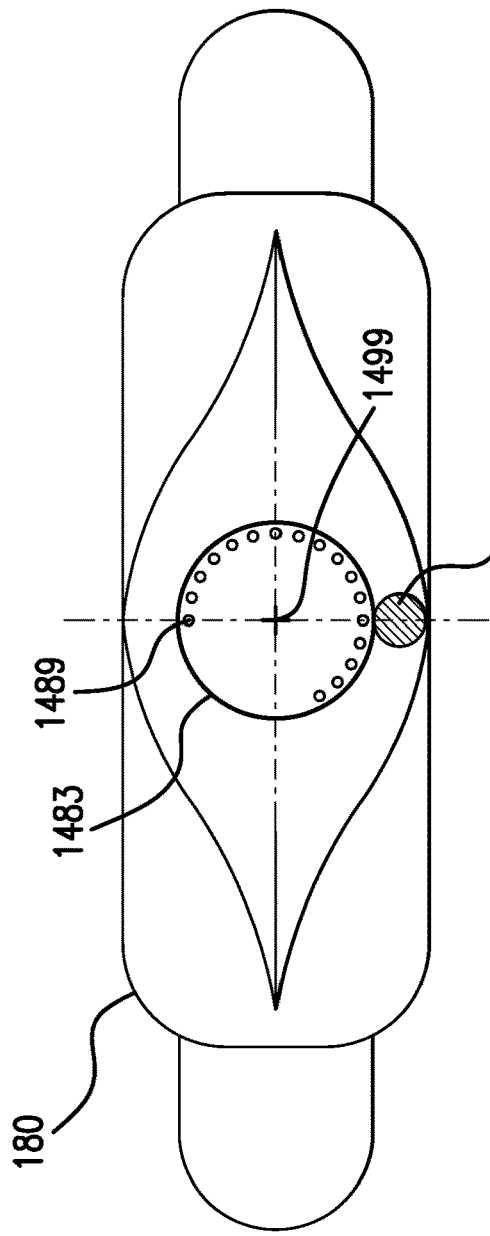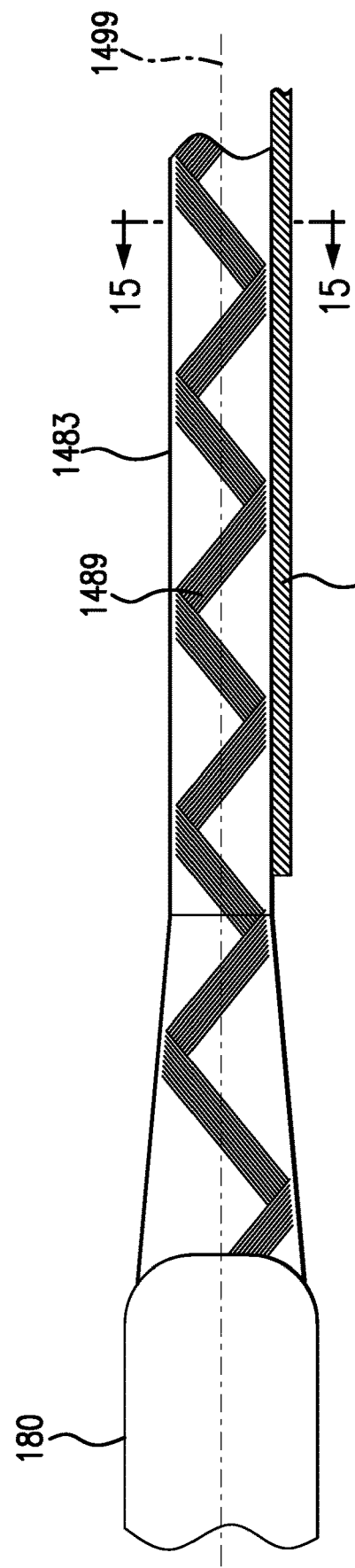

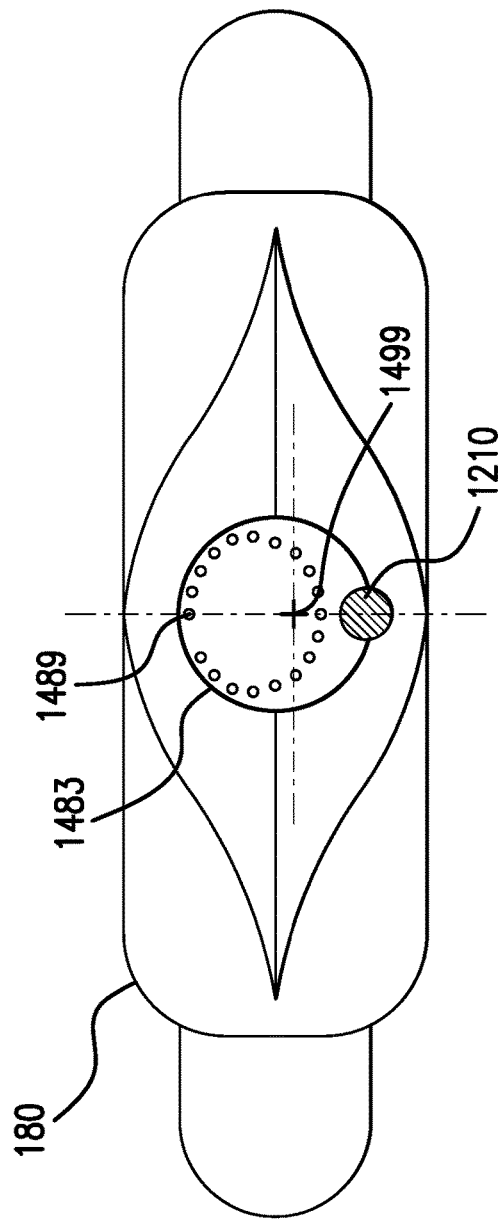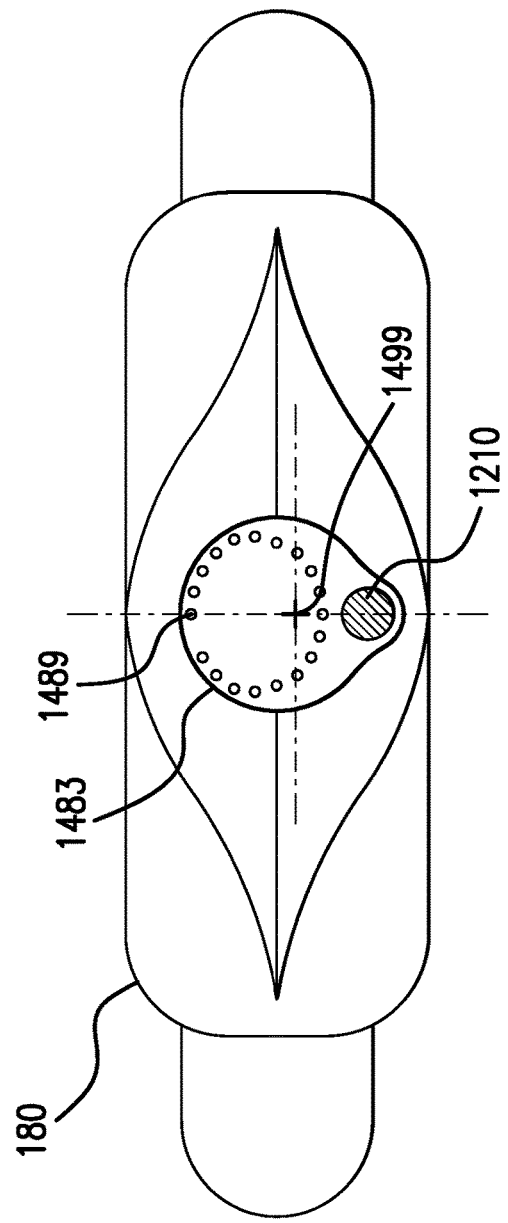
FIG. 16A
FIG. 16B

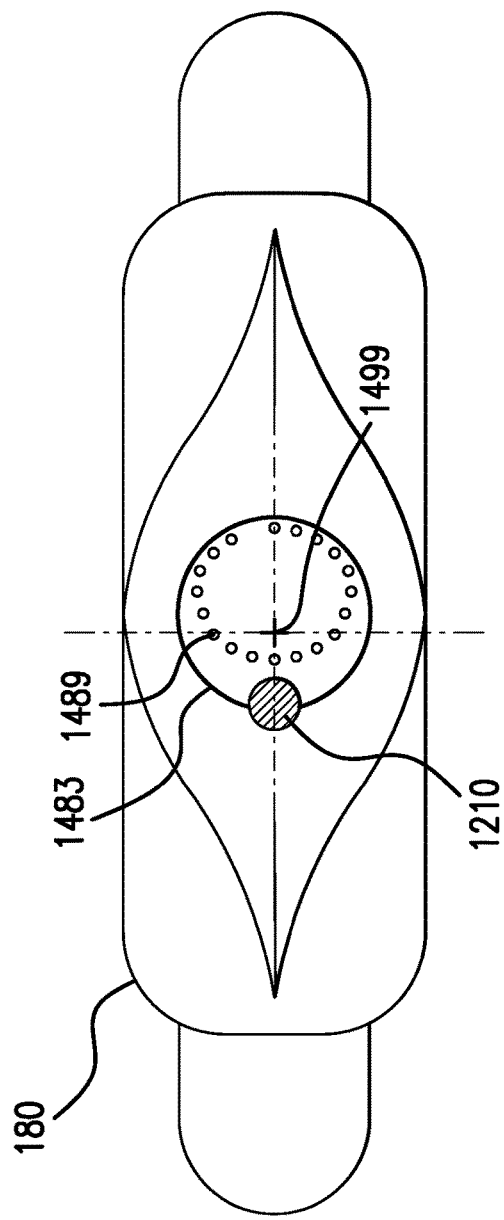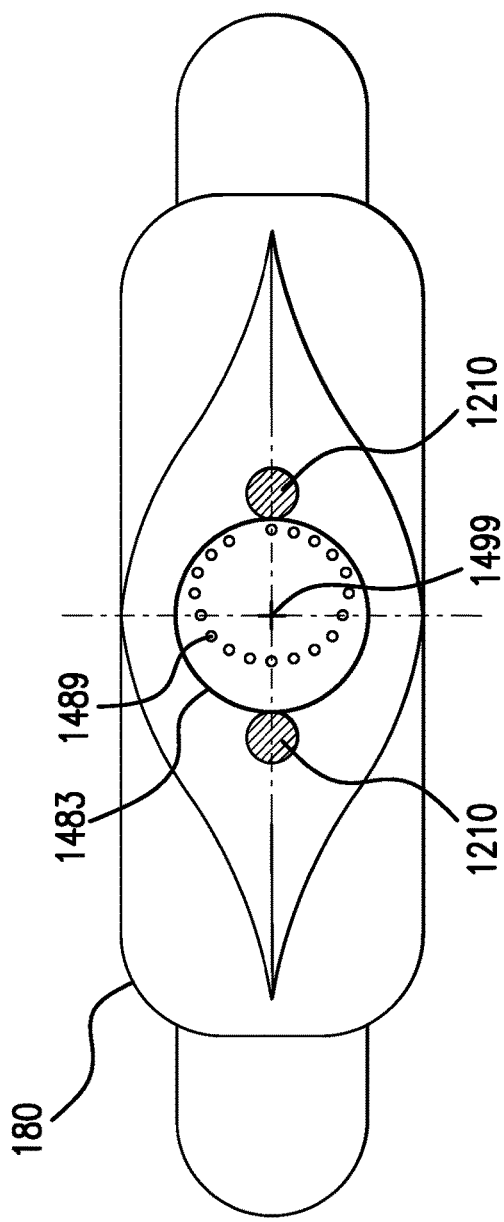

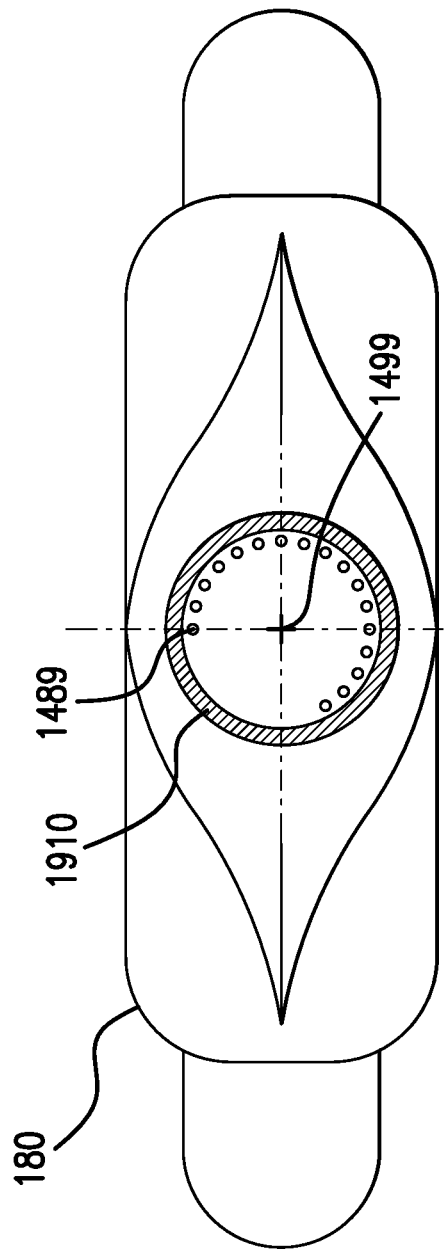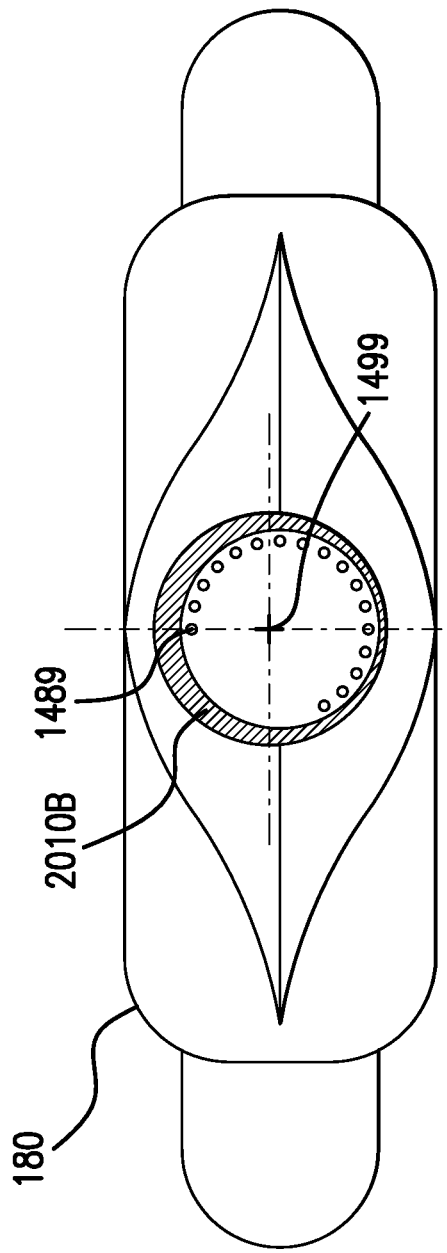

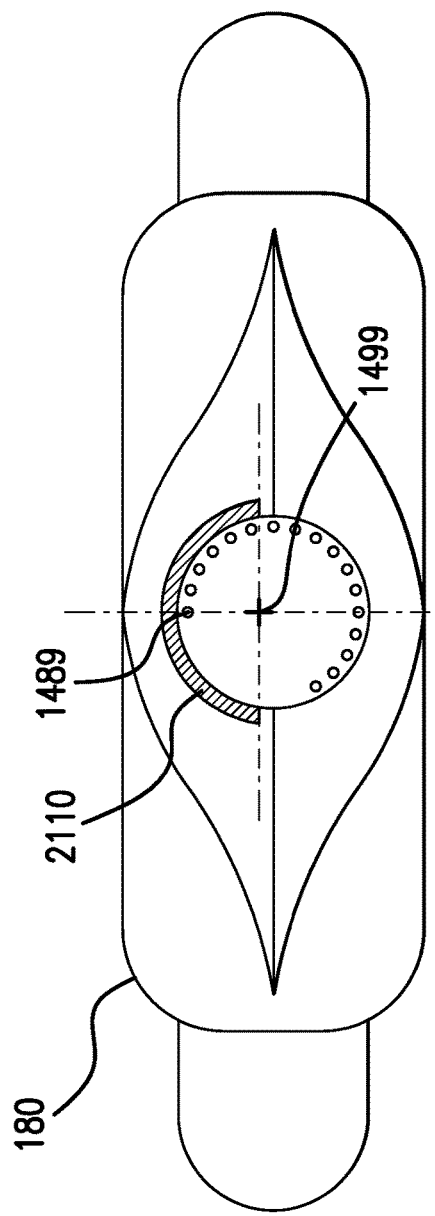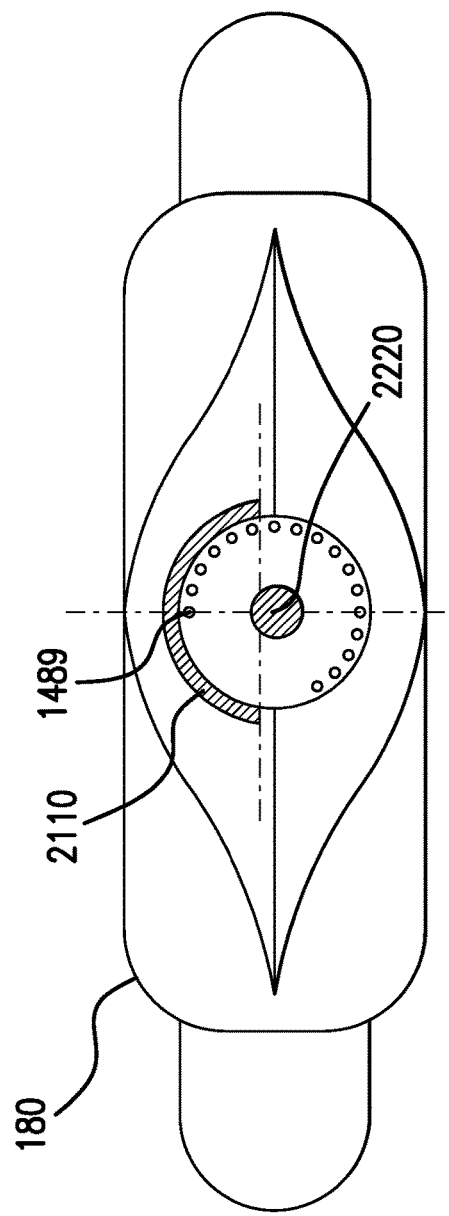

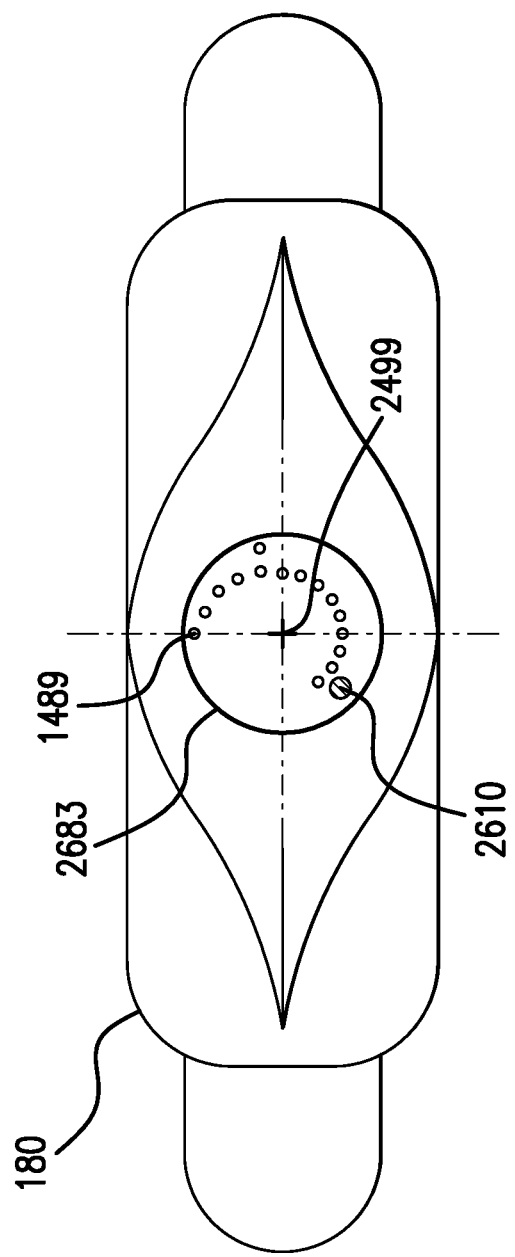

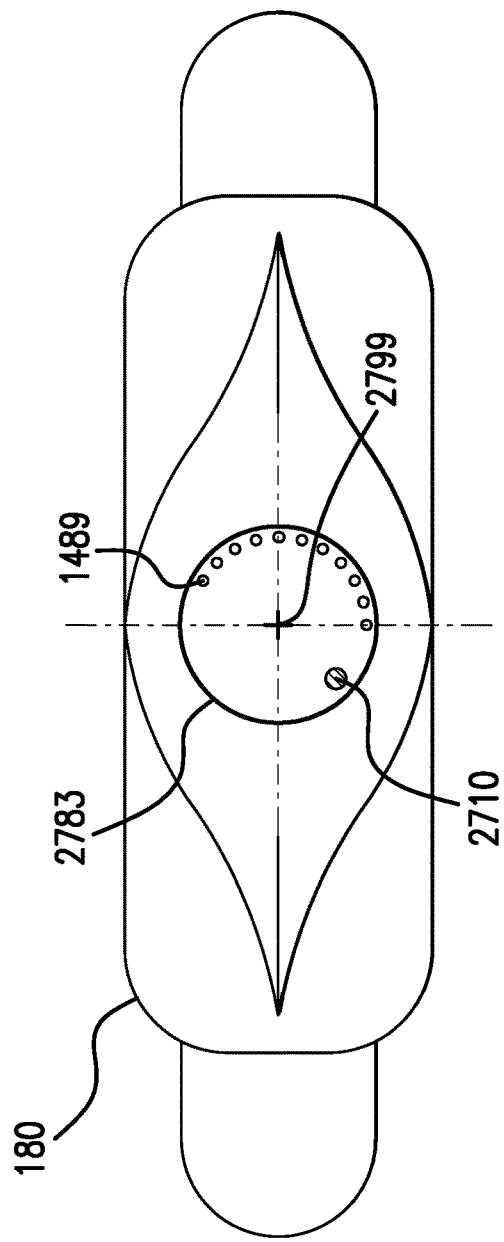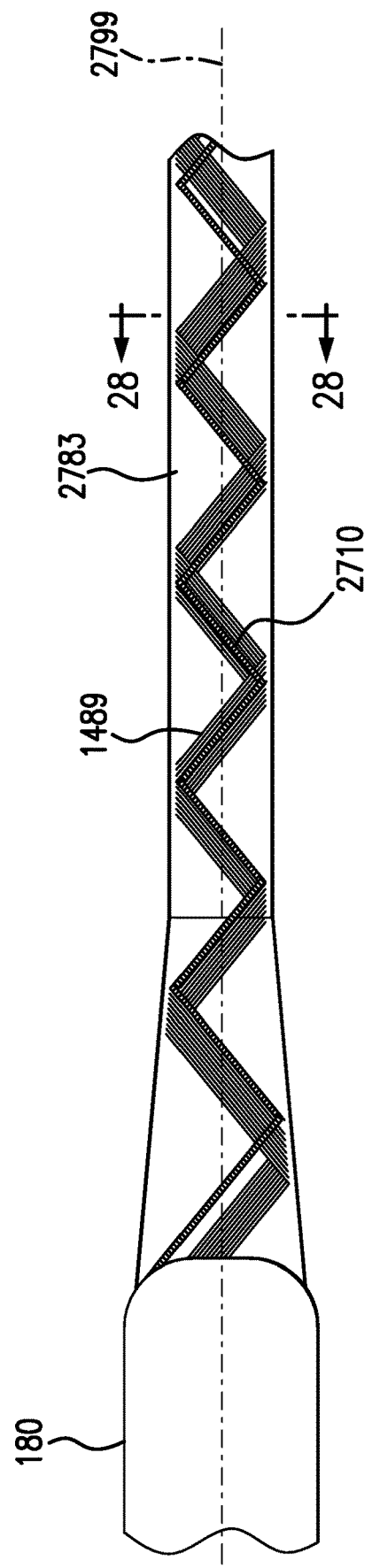
FIG. 28
FIG. 27

IMPLANTABLE STIMULATING ASSEMBLY

CROSS-REFERENCE TO RELATED APPLICATIONS

This application claims priority to Provisional U.S. Patent Application No. 62/211,434, entitled IMPLANTABLE STIMULATING ASSEMBLY, filed on Aug. 28, 2015, naming Peter Raymond Sibary of Macquarie University, Australia, as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In an exemplary embodiment, there is an elongate stimulation assembly of an implantable stimulation device, comprising an intra-cochlear portion including an array of electrodes, and an extra-cochlear portion extending from the intra-cochlear portion, wherein the extra-cochlear portion includes a plurality of electrical lead wires in electrical communication with the array of electrodes and a malleable component extending in an elongate manner such that at least a portion of the malleable component is located further away from or the same distance from a longitudinal axis of the extra-cochlear portion than a portion of least one of the electrical leads of the plurality of electrical leads.

In another exemplary embodiment, there is an elongate stimulation assembly of a cochlear implant, comprising an intra-cochlear portion including an array of electrodes, and lead wires extending from the intra-cochlear region in electrical communication with the array of electrodes, the lead wires being located in an elongate lead body, and a malleable component extending in an elongate manner at least partially along with the lead wires, wherein the malleable component is located closer to an outer surface of the lead body than at least one of the lead wires or wherein the malleable component is located the same distance from the outer surface of the lead body as at least one of the lead wires.

In another exemplary embodiment, there is a device, comprising a stimulating assembly of an implantable stimulating device, including a lead assembly made at least partially of elastic material having a tendency/desire to return to an original shape/spring back from a position placed by the surgeon (springiness), wherein the device is configured to resist movement of at least a portion of the lead assembly, the movement of the lead assembly due to the elastic nature of this material.

In another exemplary embodiment, there is a method, comprising obtaining access to a subcutaneous region of a recipient's head, implanting a stimulating assembly at the subcutaneous region, wherein the action of implanting the electrode assembly includes plastically deforming a first portion of the stimulating assembly so as to maintain the first portion now deformed at a first orientation due to the deformation of the first portion.

BRIEF DESCRIPTION OF THE DRAWINGS

Embodiments of the present invention are described below with reference to the attached drawings, in which:

FIG. 6 is a schematic of an apparatus to which some teachings detailed herein have been applied;

FIG. 7 is a quasi-functional side view of a portion of the embodiment of FIG. 6;

FIG. 8 is a cross-sectional view of the embodiment of FIG. 7;

FIGS. 10C-F are side-views of a portion of the anatomy of a human along with other exemplary embodiments;

FIG. 11A is a flowchart according to an exemplary method;

FIG. 14 is a quasi-functional side view of a portion of the an alternate embodiment of the embodiment of FIG. 6;

FIG. 15 is a cross-sectional view of the embodiment of FIG. 14;

FIG. 16A is a cross-sectional view of an alternate embodiment of the embodiment of FIG. 6;

FIG. 16B is a cross-sectional view of another alternate embodiment of the embodiment of FIG. 6;

FIG. 17 is a cross-sectional view of another alternate embodiment of the embodiment of FIG. 6;

FIG. 18 is a cross-sectional view of another alternate embodiment of the embodiment of FIG. 6;

FIG. 19 is a cross-sectional view of another alternate embodiment of the embodiment of FIG. 6;

FIG. 20 is a cross-sectional view of another alternate embodiment of the embodiment of FIG. 6;

FIG. 21 is a cross-sectional view of another alternate embodiment of the embodiment of FIG. 6;

FIG. 22 is a cross-sectional view of another alternate embodiment of the embodiment of FIG. 6;

FIG. 26 is a cross-sectional view of another alternate embodiment of the embodiment of FIG. 6;

FIG. 27 is a quasi-functional side view of a portion of another embodiment of the embodiment of FIG. 6;

FIG. 28 is a cross-sectional view of the embodiment of FIG. 24;

DETAILED DESCRIPTION

Figure 1A:
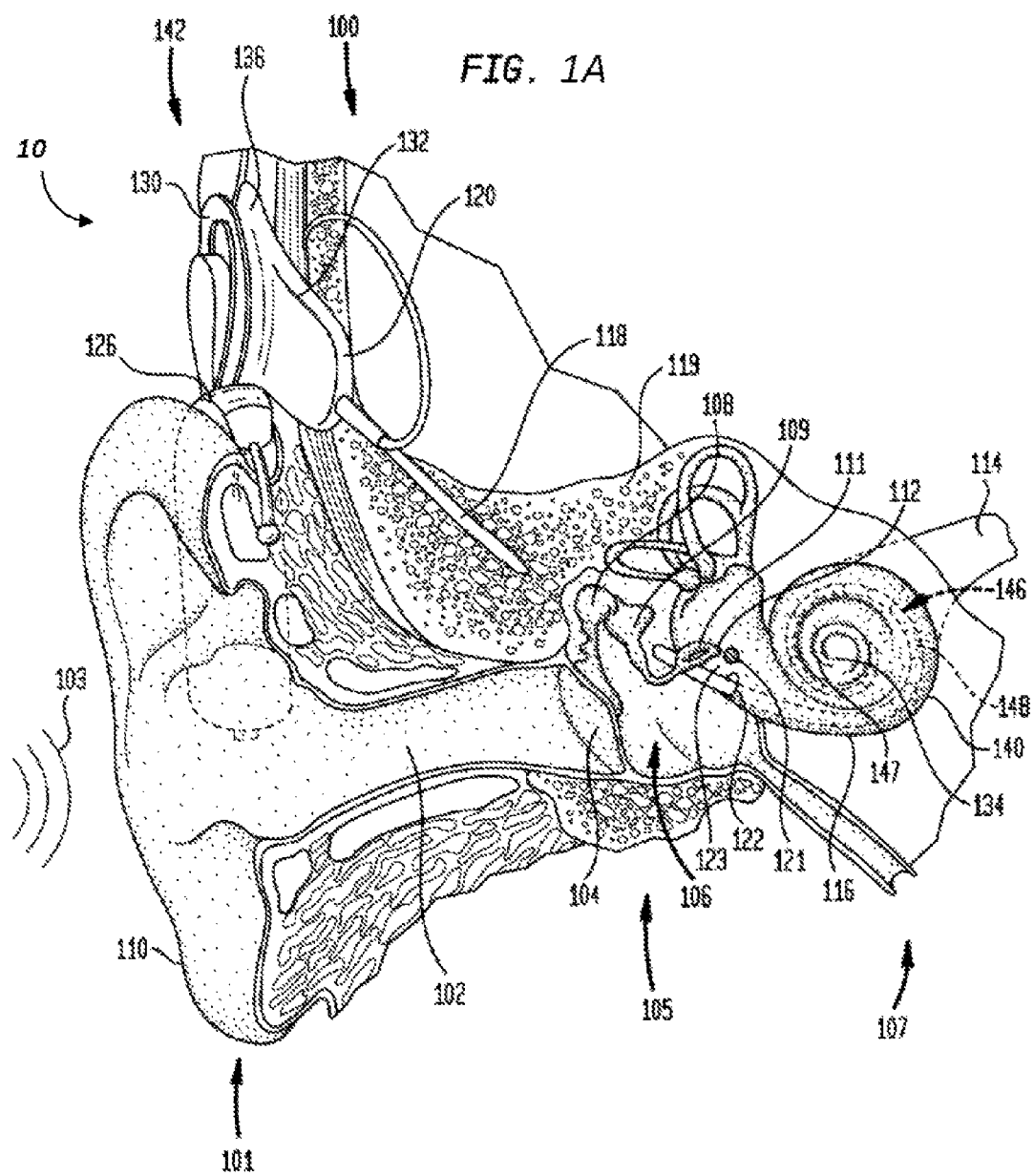
FIG. 1A is a perspective view of an exemplary hearing prosthesis utilized in some exemplary embodiments.

FIG. 1A is perspective view of a totally implantable cochlear implant according to an exemplary embodiment, referred to as cochlear implant 100, implanted in a recipient. The cochlear implant 100 is part of a system 10 that can include external components, as will be detailed below.

In an alternate embodiment, the cochlear implant system is not a totally implantable system. By way of example, the cochlear implant system includes an external component that includes a microphone and a sound processor. The sound processor processes signals from the microphone, and generates a signal that is transmitted transcutaneously to an implantable component which then uses the signal to stimulate tissue and evoke a hearing percept.

It is noted that in some conventional parlances, the entire system 10 is referred to as a cochlear implant, especially in the case of a cochlear implant that is not totally implantable. Herein, the phrase cochlear implant refers to the implantable component, and the phrase cochlear implant system refers to the entire system 10. That is, the phrase cochlear implant corresponds to the implantable component of a non-totally implantable cochlear implant system.

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant.

In the illustrative arrangement of FIG. 1A, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand/or multi-strand platinum or gold wire. External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand/or multi-strand platinum or gold wire.

Cochlear implant 100 further comprises a main implantable component 120 and an elongate stimulating assembly 118. In embodiments of the present invention, internal energy transfer assembly 132 and main implantable component 120 are hermetically sealed within a biocompatible housing. In embodiments of the present invention, main implantable component 120 includes a sound processing unit (not shown) to convert the sound signals received by the implantable microphone in internal energy transfer assembly 132 to data signals. Main implantable component 120 further includes a stimulator unit (also not shown) which generates electrical stimulation signals based on the data signals. The electrical stimulation signals are delivered to the recipient via elongate stimulating assembly 118.

Elongate stimulating assembly 118 has a proximal end connected to main implantable component 120, and a distal end implanted in cochlea 140. Stimulating assembly 118 extends from main implantable component 120 to cochlea 140 through mastoid bone 119. In some embodiments stimulating assembly 118 may be implanted at least in basal region 116, and sometimes further. For example, stimulating assembly 118 may extend towards apical end of cochlea 140, referred to as cochlea apex 134. In certain circumstances, stimulating assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating assembly 118 comprises a longitudinally aligned and distally extending array 146 of electrodes 148, disposed along a length thereof. As noted, a stimulator unit generates stimulation signals which are applied by stimulating contacts 148, which, in an exemplary embodiment, are electrodes, to cochlea 140, thereby stimulating auditory nerve 114. In an exemplary embodiment, stimulation contacts can be any type of component that stimulates the cochlea (e.g., mechanical components, such as piezoelectric devices that move or vibrate, thus stimulating the cochlea (e.g., by inducing movement of the fluid in the cochlea), electrodes that apply current to the cochlea, etc.). Embodiments detailed herein will generally be described in terms of a stimulating assembly 118 utilizing electrodes as elements 148. It is noted that alternate embodiments can utilize other types of stimulating devices. Any device, system or method of stimulating the cochlea can be utilized in at least some embodiments.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in main implantable component 120, or disposed in a separate implanted location.

It is noted that the teachings detailed herein and/or variations thereof can be utilized with a non-totally implantable prosthesis. That is, in an alternate embodiment of the cochlear implant 100, the cochlear implant 100, and thus system 10, is a traditional hearing prosthesis.

While various aspects of the present invention are described with reference to a cochlear implant (whether it be a device utilizing electrodes or stimulating contacts that impart vibration and/or mechanical fluid movement within the cochlea), it will be understood that various aspects of the embodiments detailed herein are equally applicable to other stimulating medical devices having an array of electrical simulating electrodes such as auditory brain implant (ABI), functional electrical stimulation (FES), spinal cord stimulation (SCS), penetrating ABI electrodes (PABI), and so on. Further, it is noted that the teachings herein are applicable to stimulating medical devices having electrical stimulating electrodes of all types such as straight electrodes, perimodiolar electrodes and short/basal electrodes. Also, various aspects of the embodiments detailed herein and/or variations thereof are applicable to devices that are non-stimulating and/or have functionality different from stimulating tissue, such as for, example, any intra-body dynamic phenomenon (e.g., pressure, or other phenomenon consistent with the teachings detailed herein) measurement/sensing, etc., which can include use of these teachings to sense or otherwise detect a phenomenon at a location other than the cochlea (e.g., within a cavity containing the brain, the heart, etc.). Additional embodiments are applicable to bone conduction devices, Direct Acoustic Cochlear Stimulators/Middle Ear Prostheses, and conventional acoustic hearing aids. Any device, system, or method of evoking a hearing percept can be used in conjunction with the teachings detailed herein. The teachings detailed herein are applicable to any device, system or method where an elongate lead having elastic properties or the like has utilitarian value with respect to positioning thereof.

Figure 1B:
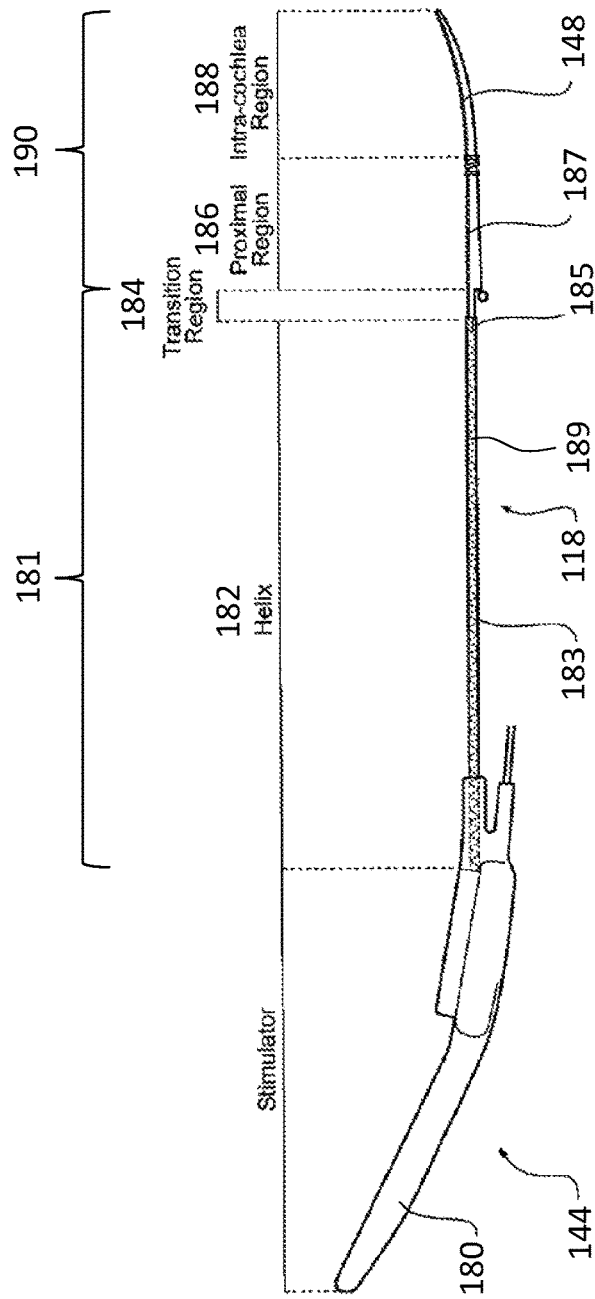
FIG. 1B is a side view of the implantable components of the cochlear implant illustrated in FIG. 1A.

Still focusing on a cochlear implant, FIG. 1B is a side view of the cochlear implant 100 without the other components of system 10 (e.g., the external components). Cochlear implant 100 comprises a receiver/stimulator 180 (combination of main implantable component 120 and internal energy transfer assembly 132) and an elongate stimulating assembly 118. Stimulating assembly 118 includes a helix region 182 that includes a body 183 in which is embedded (e.g., in the case where the body is silicone or another biocompatible material molded around wire leads) or otherwise containing (e.g., in the case where the body is a conduit or tube) electrical lead wires 189 in a helix (more on this below), a transition region 184 (which can be part of the body 183), a proximal region 186, and an intra-cochlear region 188. The proximal region 186, in this embodiment, is connected to the transition region 184 via a distinct connection 185, although in other embodiments, the transition region is blended into the helix region 182 (and the proximal region 186). Proximal region 186 and intra-cochlear region 188 form an electrode array 190. The portion of the stimulating assembly 118 that extends from the receiver/stimulator 180 to the electrode array 190 is referred to herein as the lead assembly, indicated by reference numeral 181 in FIG. 1A. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the stimulating assembly 118. In some exemplary embodiments, nubs 187 are provided on the outer surface of the proximal region to aid in the manipulation of the electrode array assembly 190 during insertion of the intra-cochlear region into the cochlea. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected to receiver/stimulator 180, through which respective stimulating electrical signals for each electrode contact 148 travel.

It is noted that in some embodiments, the helix region 182 does not extend as far as that depicted in FIG. 1A, and the transition region 184 is thus longer. That is, in some exemplary embodiments, the helix region 182 does not extend substantially the full length between the receiver/stimulator 180 and the proximal region 186, but instead extends less than that (e.g., about half the distance), where the remaining distance is established by substantially straight lead wires, or at least wires that are not substantially helixed. Any arrangement of lead wires that can enable the teachings detailed herein and/or variations thereof to be practiced can be utilized in some exemplary embodiments.

Figure 2:
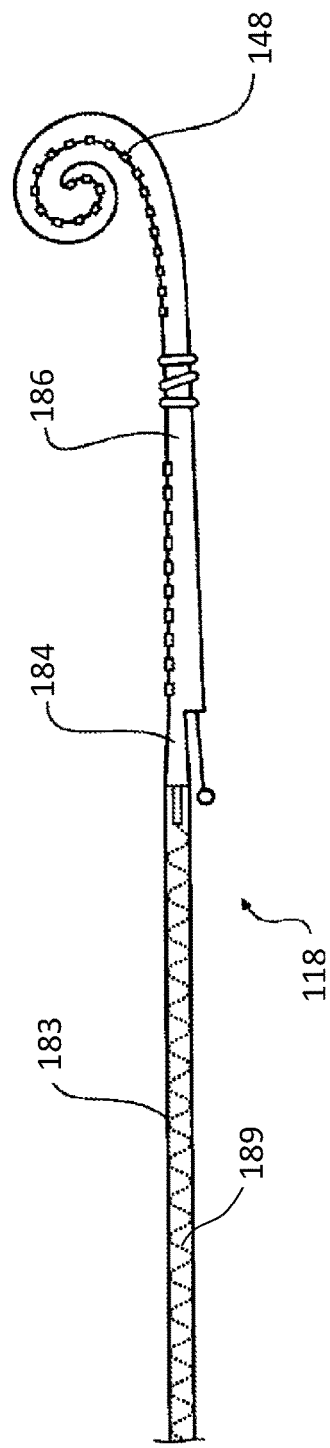
FIG. 2 is a side view of an embodiment of the electrode array illustrated in FIGS. 1A and 1B in a curled orientation.

FIG. 2 is a side view of a portion of stimulating assembly 118 where the electrode array of the electrode array assembly 190 is in a curled orientation, as it would be when inserted in a recipient's cochlea, with electrode contacts 148 located on the inside of the curve. FIG. 2 depicts the electrode array of FIG. 1B in situ in a patient's cochlea 140.

Figure 3:
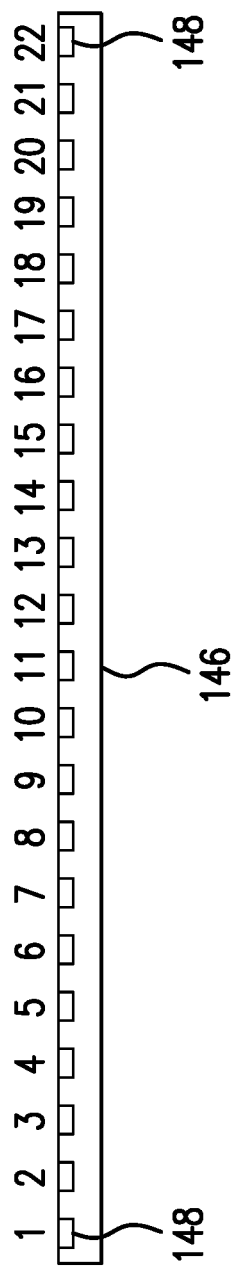
FIG. 3 is a functional schematic of an electrode array including 22 electrodes spaced apparat from one another.

FIG. 3 illustrates a more detailed view, albeit functionally, of an exemplary electrode array 146 comprising a plurality of electrodes 148 labeled 1-22, in accordance with an embodiment. In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel). Briefly, it is noted that during stimulation by the electrodes to evoke a hearing percept, one or more electrodes 148 is activated at a given electrode stimulation level (e.g., current level).

Figure 4:
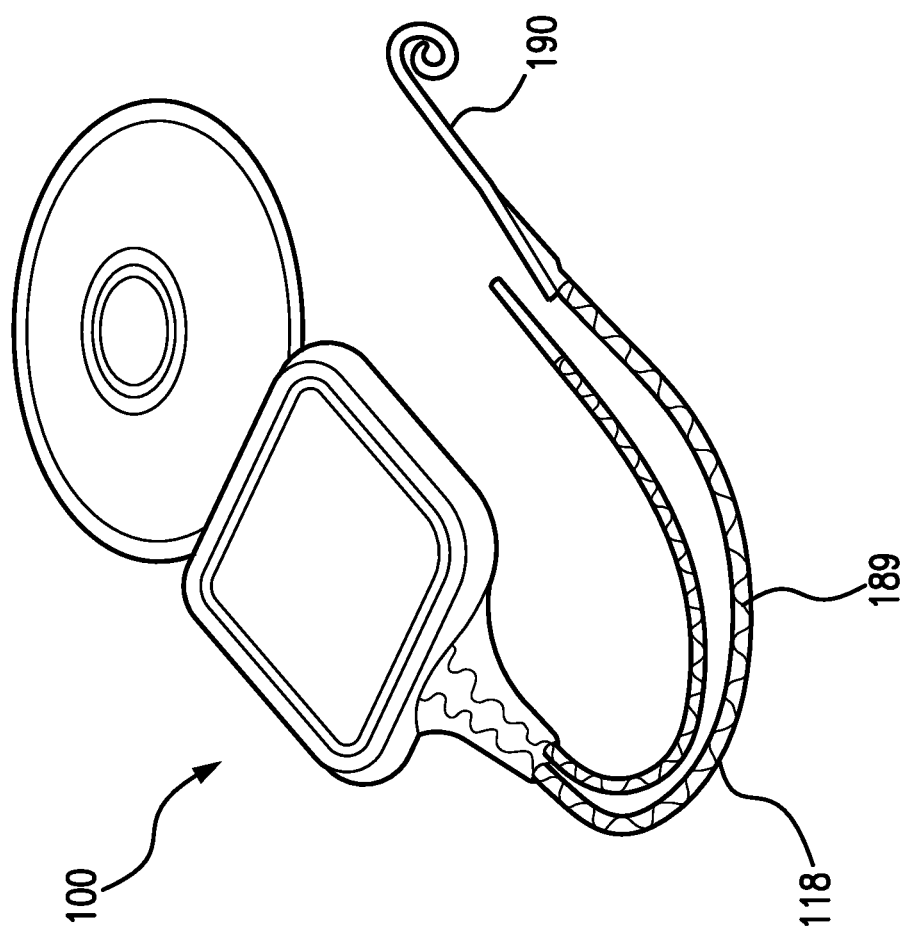
FIG. 4 is a schematic of an apparatus to which some teachings detailed herein are applicable.

FIG. 4 depicts an isometric view of a cochlear implant 100 corresponding to the cochlear implant 100 detailed above.

Figure 5:
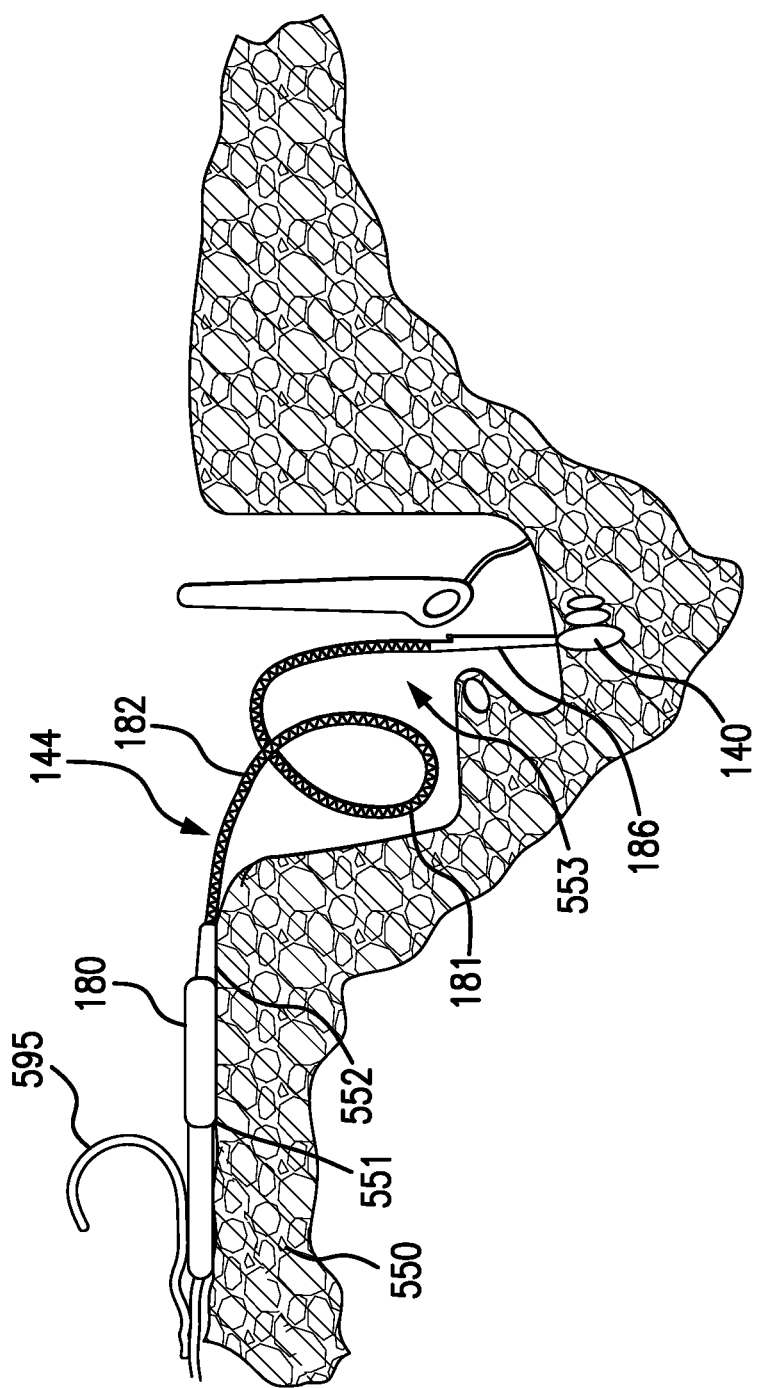
FIG. 5 is a side-view of a portion of the anatomy of a human along with an exemplary embodiment.

FIG. 5 depicts an exemplary cochlear implant 100 implanted in a recipient just before "closing" during the surgical implantation process. As can be seen, receiver/stimulator 180 lies in a bed 551 formed in the mastoid bone 550 of a recipient, with a skin flap 595 of the scalp of the recipient's head folded back. The bed 551 provides a space for location of the receiver/stimulator 180 to retain the receiver/stimulator in place in the patient's skull and to minimize protrusion of the receiver/stimulator package from the skull when in place after the skin flap 595 is placed back over the receiver; stimulator. A channel 552 is also provided to accommodate the base of the stimulating assembly 118 and the portion of the helix region 182 (or the transition region, if such is that long) of the lead assembly located therein that extends from the receiver/stimulator 180. A hole is drilled into the mastoid bone to allow the electrode array assembly 190 to enter the cavity established by the middle ear and the mastoid cavity 553 and provide access to the round window of the cochlea 140. The area of bone that is removed to provide access to the cochlea 140 is referred to as the mastoid cavity 553. FIG. 5 shows that the stimulating assembly 118 is configured to be long enough to permit the surgeon to manipulate the stimulating assembly 118 into the cochlea 140, as well as to take account for any growth in the patient's skull, if implanted at a young age. Accordingly, in some exemplary embodiments, the surgeon sometimes forms a loop in the transition region of the electrode array assembly that is then placed in the mastoid cavity 553, to account for any excess lead length. However, as will be detailed below, in some alternate exemplary embodiments, this loop is not formed, and alternate actions/arrangements are provided to account for the extra length of the lead.

It is noted that in at least some exemplary embodiments, a portion of the helix region and/or the transition region of the stimulating assembly 118 can be tucked underneath a bony overhang of bone forming a portion of the boundary of a mastoid cavity. Such will be described below in greater detail. In an exemplary embodiment, this can have utilitarian value in that such can secure, or otherwise at least temporarily retain, a portion of the stimulating assembly 118 at a given location. In this regard, the retained portion is separated from the skin overhanging the mastoid cavity 553 by the bony overhang. Still further, in an exemplary embodiment, at least during the surgical procedure, while the portion that is retained underneath the bony overhang is so retained, it is easier to close the skin flap 595. This is because, by way of example only and not by way of limitation, the stimulating assembly 118 is retained from "springing up" out of the mastoid cavity 553. In this regard, it is noted that in at least some exemplary embodiments, the makeup of the stimulating assembly 118, at least with respect to the portions of the helix region and/or the transition region, or at least the portion extending between the receiver/stimulator 180 and the electrode array 190 (the lead assembly 181), or at least a portion thereof, is elastic in nature, in that it has a desire to "spring back" or otherwise return to a first orientation when placed in a second orientation (e.g., returning to a generally straight orientation). In this regard, in an exemplary embodiment, the lead assembly behaves in a manner somewhat analogous to a rubber band, where once the rubber band is unrestrained, it returns to a given shape. In this regard, in an exemplary embodiment, it is due to the elastic tendencies of the lead assembly, or at least the elastic tendencies of some of the material that makes up the lead assembly, that result in the phenomenon of the lead assembly springing out of the mastoid cavity 553. In this regard, in at least some instances, it can be relatively difficult to place the lead assembly 181 in an orientation that will result in the lead assembly 181 remaining within the mastoid cavity 553 at least enough so that the closing process can be executed. Because of this, it can be sometimes difficult to maintain the lead assembly 181 underneath and/or in contact with the bony overhang. Still further, even after the skin flap 595 is secured back in place, after closing, the lead assembly can "migrate" away from the aforementioned bony overhang and come into contact with the skin (the underside of the skin), and can rub/irritate the bottom of the skin in that the stimulating assembly can put pressure on the underside of the skin if it comes into contact with the underside of the skin in general, and if the elasticity of the stimulating assembly is such that it puts an upward force on to the underside of the skin. In some scenarios, the stimulating assembly can rub through the skin to extrude out of the skin. This tends to be undesirable with at least some recipients. In an exemplary embodiment, this can be due to the elastic tendencies of the lead assembly 181, or at least a portion thereof. Accordingly, in an exemplary embodiment, there is an implanted cochlear implant that includes a stimulating assembly having a portion thereof extending from the exit of the channel to the cochlea that is not in contact with skin of the recipient, where the portion extending between the channel exit and the cochlea is about 30 mm, 35 mm, 40 mm, 45 mm, 50 mm, 55 mm, 60 mm or more in length or any value or range of values therebetween in about 1 mm increments. An exemplary embodiment that, in some embodiments, thereof, has utilitarian value in that some and/or all of the aforementioned difficulties/phenomena can be alleviated or otherwise prevented, will now be described.

FIG. 6 depicts an exemplary cochlear implant 600 having the functionality of cochlear implant 100 detailed above. Indeed, in an exemplary embodiment, cochlear implant 600 is identical to cochlear implant 100 and/or any other cochlear implant having a stimulating assembly 118, except that in this exemplary embodiment, cochlear implant 600 includes a device configured to prevent, or at least resist, movement of at least a portion of the lead assembly 181 of the stimulating assembly 118, at least in a manner greater than that with respect to conventional cochlear implants. More specifically, in an exemplary embodiment, FIG. 6 includes a stimulating assembly 618 of an implantable stimulating device, such as by way of example only and not by way of limitation, a cochlear implant, that includes a lead assembly made at least partially of material having elasticity/elastic qualities. That is, in the absence of at least some of the teachings detailed herein, the lead assembly would have a tendency or otherwise a "desire," due to the material properties associated with the lead assembly (e.g., the use of silicone to establish a body thereof, the use of spring-like electrical lead wires, etc.), to return to a first orientation when placed into a second orientation (e.g., spring away from the bony overhang noted above, uncoil, wind upwards towards the underside of the skin from a position where the array was away from the skin, etc.). In an exemplary embodiment, as noted above, in the absence of at least some of the teachings detailed herein, this can result in the lead assembly extending out of the mastoid cavity during the surgical procedure implanting the cochlear implant 600. Accordingly, in this exemplary embodiment, this device is configured to resist movement of at least a portion of the lead assembly, wherein the movement of the lead assembly is due to the elasticity of the lead assembly. In an exemplary embodiment, the movement associated with the elasticity is resisted or otherwise prevented from occurring due to a structure co-located with the lead assembly. In an exemplary embodiment, this entails a malleable portion 610, as can be seen in FIG. 6.

Briefly, it is noted that all disclosures herein regarding to resistance of movement also corresponds to a disclosure of the prevention of movement, and vice versa. Still further, all disclosure herein with regard to resistance of movement and/or prevention of movement corresponds to a disclosure of maintenance of a given orientation and/or position of the electrode array, and vice versa. Still further, all disclosure herein with regard to these aforementioned features also corresponds to a disclosure of enabling the positioning of the electrode array at a given location and subsequently maintaining that positioning. In this regard, the malleable feature can be considered to provide a dual role of both resisting movement, while also enabling the relatively precise positioning of the lead assembly.

It is noted that FIG. 6 depicts a quasi-conceptual schematic of a cochlear implant 100 including the aforementioned structure. In this regard, it is noted that the structure 610 is depicted as being located within the stimulating assembly 118. As will be described below, in some alternative embodiments, the aforementioned structures will be located outside the stimulating assembly 118. To be clear, some additional exemplary embodiments will be described below. The focus of this portion of the specification is to describe the general concepts of at least some exemplary embodiments with respect to an exemplary embodiment where the structure 610 is embedded in a body establishing the lead assembly 181, where, as will be detailed below, other exemplary embodiments exist where the structure is co-located with the lead assembly 181, but the structure is located outside the body establishing the lead assembly 181.

FIG. 7 depicts an exemplary cross-sectional view of an exemplary embodiment of a cochlear implant having a receiver/stimulator 180 from which extends a stimulating assembly 718 that includes a lead assembly corresponding to any of the lead assemblies detailed above, that also includes a malleable metal wire 710, corresponding to the structure 610 of FIG. 6, embedded in the body 783 establishing the lead assembly. As can be seen, wire leads 789 extend from the receiver/stimulator 180. In an exemplary embodiment, these wire leads 789 are embedded in silicone, which establishes the body 783 of the lead assembly. The wire leads depicted in FIG. 7 are depicted as leads that are straight. However, as will be detailed below, leads in a helix arrangement can be utilized in some alternate embodiments (straight leads and leads in a helix configuration can be combined in some embodiments). Additional details of this will be described below.

FIG. 8 depicts a cross-sectional view of the stimulating assembly 718, along with the receiver/stimulator 180 in the background, where the bottom of the receiver/stimulator 180 corresponds to the surface that is placed against the mastoid bone when placed in the bed 551 (i.e., the bottom of the bed contacts the bottom of the receiver/stimulator). As can be seen, malleable wire 710 is embedded in the silicone body 783 of the stimulating assembly 718, and is orientated such that it is closer to the bottom of the receiver/stimulator than the top of the receiver/stimulator.

In an exemplary embodiment, the metal wire 710 is made of platinum or some other "soft" metal. That said, in some embodiments, depending on the dimensions, a stainless steel or the like could be used (providing that the diameter was thin enough to enable the bending having utilitarian value detailed herein). Other metals and alloys can be utilized. Any metal and/or alloy that is malleable in a given structural configuration that can enable the teachings detailed herein and/or variations thereof to be practiced can be utilized in at least some embodiments. Other types of material can be utilized as well, such as by way of example only and not by way of limitation, a plastically deformable polymer, again providing that the teachings detailed herein and/or variations thereof can be practiced.

In an exemplary embodiment, the diameter of a cross-section of the malleable structure, which cross-section can have a circular cross-section, lying on a plane normal to the longitudinal axis thereof, is about 0.2 mm, although greater or smaller diameters can be utilized. In an exemplary embodiment, the diameter, which can be a maximum diameter, is about 0.1 mm, 0.15 mm, 0.2 mm, 0.25 mm or about 0.3 mm or any value or range of values there between in about 0.01 mm increments.

In an exemplary embodiment, the malleable structures detailed herein are not utilized to conduct electricity or signals. Instead, in some embodiments, they are only used for and configured to be used for the spatial maintenance features described herein. In an exemplary embodiment, the malleable structures are structurally different (significantly structurally different in most embodiments) than the electrical lead wires extending from the receiver stimulator of the implant to the electrode array. Indeed, in an exemplary embodiment, the diameter of the malleable structure(s) is an order of magnitude larger than that of a given lead wire. Moreover, as detailed herein, the malleable structures impart spatial maintenance capabilities of the elongate body that are not achieved in the presence of the lead wires alone. In is regard, in an exemplary embodiment, the malleable structures are configured to enable positioning of the elongate stimulating assembly 118 at locations, with the receiver stimulator and the electrode array held in place, and the elongate stimulating assembly unrestrained, at locations that cannot be positioned without the malleable structure (i.e., if the malleable structure was not present, but just the leads were present), all other things being equal. In an exemplary embodiment, the elongate simulating assembly can be placed into a configuration where the elongate simulating assembly subtends an angle of at least 90 degrees, 120 degrees, 150 degrees. 175 degrees, 180 degrees, 195 degrees, 210 degrees, 230 degrees, 250 degrees, 275 degrees, 300 degrees, 330 degrees and/or 360 degrees or more, and maintain that configuration without any component of the implant being secured to anything (e.g., the implant simply laying on a table, etc.).

As seen in FIG. 7, the lead assembly of the stimulating assembly 718 has a longitudinal axis 799. As can be seen, the wire 710 is located further away from the longitudinal axis 799 than the wire leads 789, or at least one wire lead. In this regard, as can be seen, the malleable wire 710 is located further away from the longitudinal axis than at least one of the electrical leads 789. While in some embodiments, the malleable wire 710 is located further from the longitudinal axis than any of the wire leads, in some alternate embodiments, some wire leads are located further from the longitudinal axis or located the same distance from the longitudinal axis as the wire 710, while one or more other wire leads are located closer to the longitudinal axis 799 than the malleable wire 710, or at least located, with respect to the closest approach of the wire leads, at the same distance from the longitudinal axis as the malleable wire (at its closes approach). Thus, in an exemplary embodiment, the extra-cochlear portion of the stimulating assembly 118 includes a plurality of electrical lead wires in electrical communication with the array of electrodes and a malleable component extending in an elongate manner such that the malleable component is located further away from a longitudinal axis of the extra-cochlear portion than at least one of the electrical leads of the plurality of electrical leads.

It is further noted that in an exemplary embodiment, at least a portion of the malleable component is located further away from or the same distance from a longitudinal axis of the extra-cochlear portion than a portion of least one of the electrical leads of the plurality of electrical leads.

Still further, in an exemplary embodiment, the malleable wire 710 is located, with respect to the longitudinal axis, at a location where its greatest distance (e.g., the surface facing away from the longitudinal axis) is located no closer than the closest distance (e.g., the surface facing towards the longitudinal axis) of at least one wire lead. That is, if the malleable wire were to orbit about the longitudinal axis, and the at least one wire lead were to remain stationary, the orbit of the malleable wire would cause the malleable wire to strike the at least one malleable lead. That said, as noted above, in an alternative embodiment, if the malleable wire were to orbit about the longitudinal axis, and the at least one wire lead were to remain stationary, the orbit of the malleable wire would not strike the at least one lead, but instead will go around the at least one lead.

As noted above, the embodiment of FIGS. 7 and 8 is depicted as having straight electrode wires embedded in the silicone body. With respect to the cross-section depicted in FIG. 8, only some of the electrode wires 789 are depicted for purposes of clarity. It will be noted that in at least some exemplary embodiments, there are 22 electrical lead wires, one electrical lead wire for each electrode 148. That said, in some alternate embodiments, more or fewer electrode wires are present.

Thus, in view of the above, in an exemplary embodiment, there is an elongate stimulation assembly of a stimulating implant, such as a cochlear implant, comprising an intra-cochlear portion including an array of electrodes (e.g., region 188 of FIG. 1B), and an extra-cochlear portion extending from the intra-cochlear portion (e.g., lead assembly 181 along with the proximal region 186, again with reference to FIG. 1B). In an exemplary embodiment, the extra-cochlear portion includes a plurality of electrical lead wires in electrical communication with the array of electrodes and a malleable component (e.g., malleable wire 710) extending in an elongate manner such that the malleable component is located further away from a longitudinal axis 799 of the extra-cochlear portion than at least one of the electrical leads 789 of the plurality of electrical leads 789. In at least some exemplary embodiments, the malleable component is a metallic element which, as detailed above, in an exemplary embodiment, is a metal wire embedded in the lead portion of the stimulating assembly 118. In an exemplary embodiment, the malleable wire 710 is embedded in silicone, which silicone forms the silicone body in which at least some of the wire leads are also embedded.

Figure 9A:
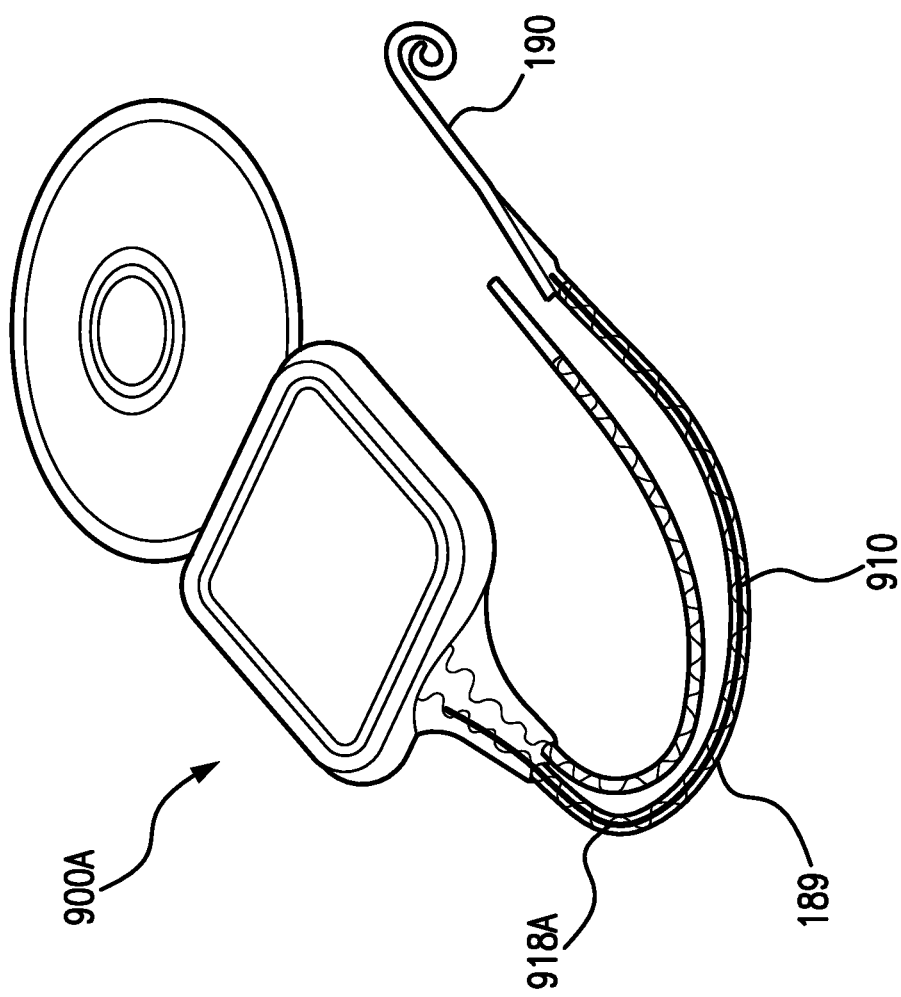
FIG. 9A is a schematic of another apparatus to which some teachings detailed herein have been applied.

FIG. 6 depicts structure 610 extending only partially along the length of the stimulating assembly 618. In this regard, in an exemplary embodiment, the extra-cochlear region of the stimulating assembly 618 is between about 70 and 80 mm (e.g., about 70, 71, 72 73, 74, 75, 76, 77, 78, 79, or about 80 mm), and structure 610 extends about 25 mm, and thus the malleable region of the stimulating assembly extends about 25 mm. It is noted that the lengths of extension of the structure 610 can be greater or smaller in some embodiments. In an exemplary embodiment, it can extend about 5 mm, 10 mm, 15 mm, 20 mm, 25 mm, 30 mm, 35 mm, 40 mm, 45 mm, 50 mm, 55 mm, 60 mm, 65 mm, or about 70 mm or more or any value or range of values therebetween in about 1 mm increments (e.g., 32 mm, 54 mm, about 7 mm to about 52 mm, etc.). Indeed, as can be seen in FIG. 9A, an exemplary alternate cochlear implant 900A includes a stimulating assembly 918A that includes structure 910 that extends at least substantially the full length between the receiver/stimulator 180 and the electrode array assembly 190. Further, in at least some exemplary embodiments, the structure 910A can further extend into the proximal region 186 of the electrode array assembly 190.

It is further noted that in an exemplary embodiment, the structure 610 (or any of the related structures detailed herein and/or variations thereof) can also be or in the alternative be implemented in the elongate assembly that supports the extra-cochlear electrode (e.g., the electrode that provides the "return" (at least in part) for the current flowing from the electrodes located in the cochlea (the other of the elongate structures of FIG. 6). Indeed, in an exemplary embodiment, the teachings detailed herein regarding the structure 610 and/or alternate embodiments thereof are applicable to any elongate structure that has the aforementioned elastic tendencies associated with stimulating assembly 618 (or even structures that do not have such elastic tendencies).

As depicted in FIG. 7, the structure forming the malleable wire 710 extends from the housing of the receiver/stimulator 180. In an exemplary embodiment, the structure can be connected to the housing of the receiver/stimulator 180. Indeed, in an exemplary embodiment, the end of the malleable wire 710 can be rigidly fixed to the housing. That said, in an alternative embodiment, the malleable wire 710 can be offset from the housing, as will be seen in an alternate exemplary embodiment below. In this regard, because, in at least some exemplary embodiments, malleable portion has utility at locations away from the housing of the receiver/stimulator 180, and, in at least some embodiments, there is little to no utilitarian value with respect to locating the malleable portion at and/or proximate the housing, the malleable portion can be offset from the housing of the receiver/stimulator 180. Any location of the malleable structures that can enable the teachings detailed herein to be practiced can be utilized in at least some embodiments.

Figure 9B:
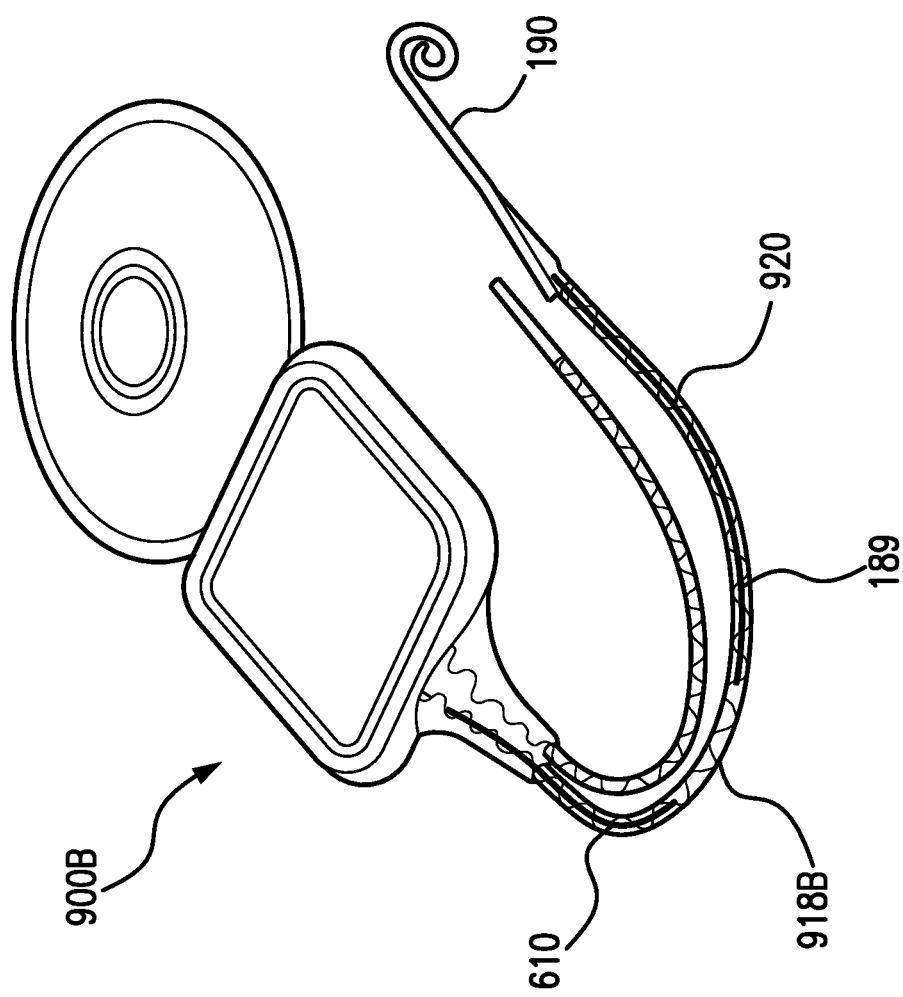
FIG. 9B is a schematic of another apparatus to which some teachings detailed herein have been applied.

FIG. 9B depicts an alternate cochlear implant 900B that includes a stimulating assembly 918B that includes structure 610 as detailed above with respect to FIG. 6 and structure 920 that extends from the electrode array 190 (although in other embodiments, it can be offset from the electrode array 190) towards the receiver/stimulator about 25 mm, leaving a section between structure 610 and structure 920 that is not malleable (a structure that is about 25 mm, in an exemplary embodiment). Thus, with respect to this embodiment, there is a receiver/stimulator of a cochlear implant connected to a lead assembly at a first location of the lead assembly. The cochlear implant, includes a first structural component (structure 610, which can be a malleable wire corresponding to malleable wire 710 detailed above, or can correspond to any other of the structures detailed herein or other structures that can enable the teachings detailed herein to be practiced) separate) and second structural component (structure 920, which can be a malleable wire corresponding to malleable wire 710 detailed above, or can correspond to any other of the structures detailed herein or other structures that can enable the teachings detailed herein to be practiced) separate from the first structural component. In this exemplary embodiment, the first structural component is located proximate the receiver/stimulator, and the second structural component is located remote from the first structural component.

Still further, in an exemplary embodiment, the first structural component is configured to prevent, or at least resist, movement of at least a first portion of the lead apparatus of the stimulating assembly of the cochlear implant, which movement can correspond to the movement resulting from the elasticity of at least a portion of the material making up the lead assembly (e.g., silicone), the first portion of the lead apparatus being proximate the first structural component. Also, the second structural component is configured to prevent, or at least resist, movement of at least a second portion of the lead apparatus, again, which movement can correspond to the movement resulting from the elasticity of at least a portion of the material making up the lead assembly, the second portion of the lead apparatus being proximate the second structural component.

Still further in view of FIG. 9B, the lead assembly of the stimulating assembly of cochlear implant 900B includes a third portion unrestrained from movement due to elasticity of the third portion, the third portion being located between the first portion and the second portion (e.g., between structure 610 and 920 of FIG. 9B.). In some exemplary embodiments, there is an electrode array located at a location, with respect to the lead assembly, opposite to the location where the lead assembly connects to the receiver/stimulator 180.

In an exemplary embodiment, the malleable portions of the cochlear implants detailed herein can have utilitarian value in that it can enable the lead assembly, or at least a portion thereof, to be deformed to an orientation that is deemed utilitarian with respect to the anatomy of a recipient (albeit in a potentially altered state due to the surgery (e.g., the creation of the mastoid cavity) which orientation will be maintained after the establishment of the orientation. In this regard, in an exemplary embodiment, the cochlear implant 600 is configured to resist the movement of the at least a portion of the lead assembly due to the elasticity via a structure, such as malleable wire 710, co-located with the lead assembly, wherein the structure is configured to deform upon the application of sufficient force. This applied force is greater than a force applied to the structure via the elasticity (and, in some embodiments, opposite that force). As will now be described, this force moves the lead assembly along with the deformation so that the lead assembly can be positioned, or at least a portion of the lead assembly can be positioned, at a desired orientation, while the malleability of the structure holds the lead assembly/portion thereof at the desired position/orientation after the positioning.

Figure 10A:
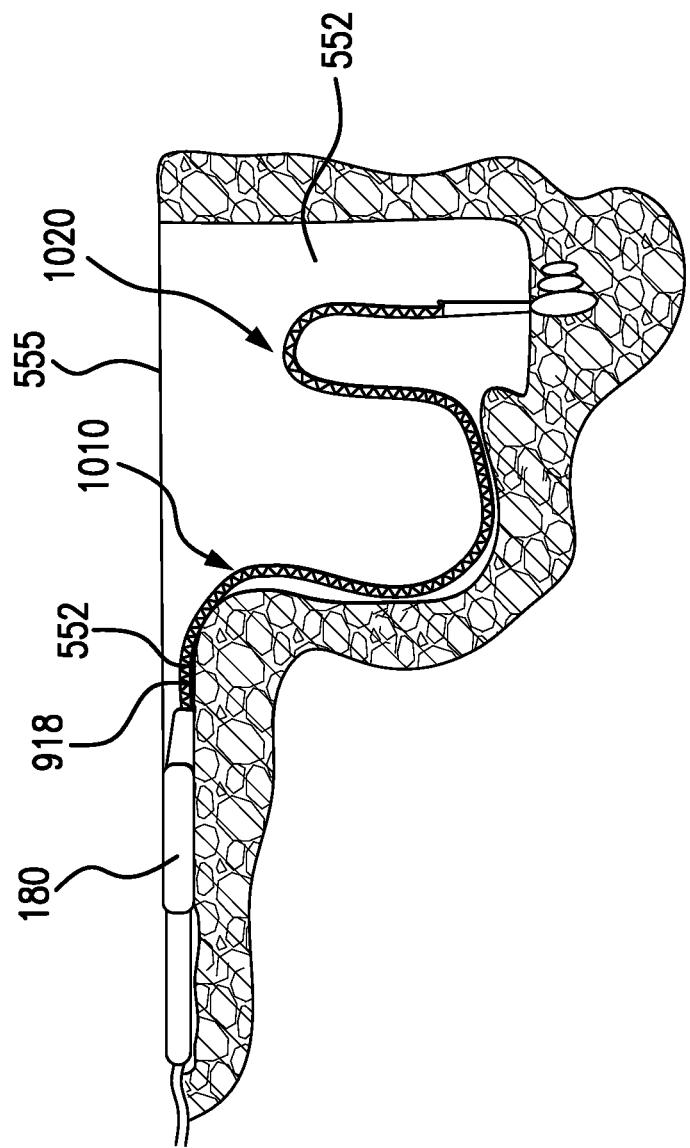
FIG. 10A is a side-view of a portion of the anatomy of a human along with another exemplary embodiment.
Figure 10B:
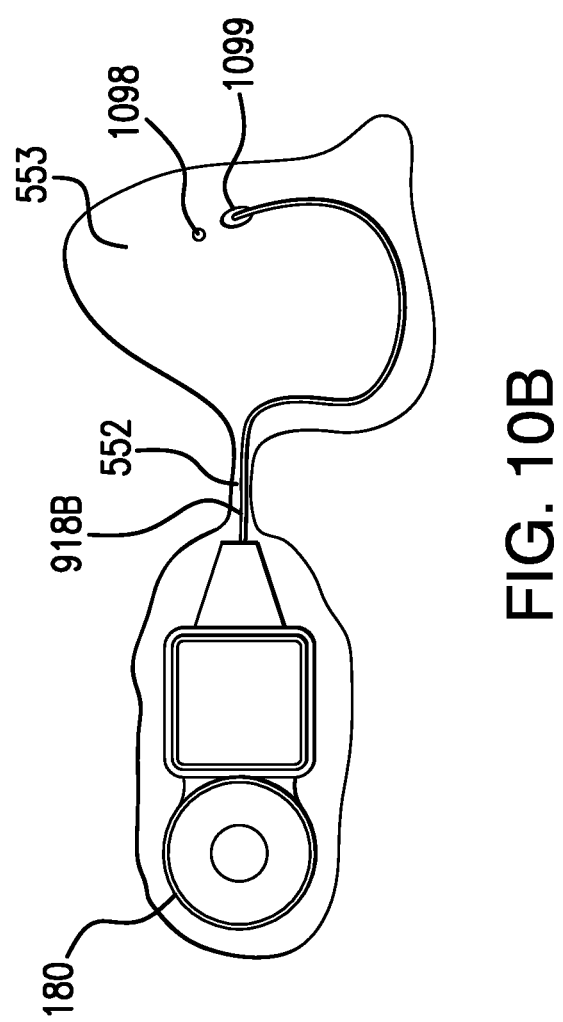
FIG. 10B is a top-view of a portion of the anatomy of a human along with another exemplary embodiment.
Figure 10C:
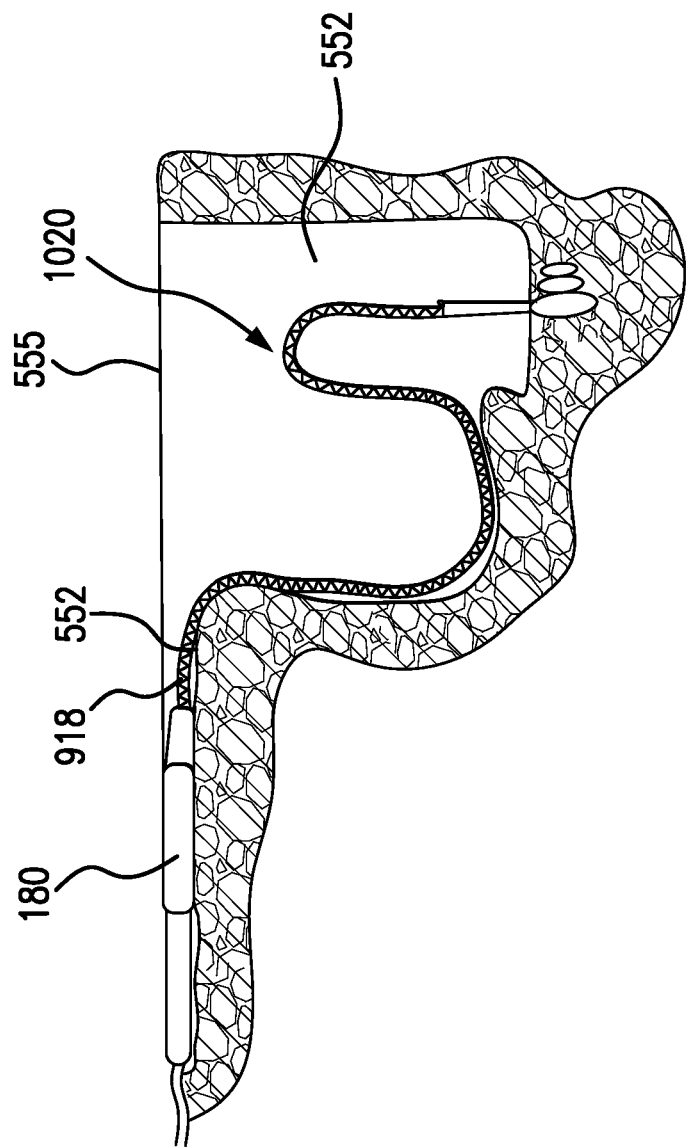
Figure 10D:
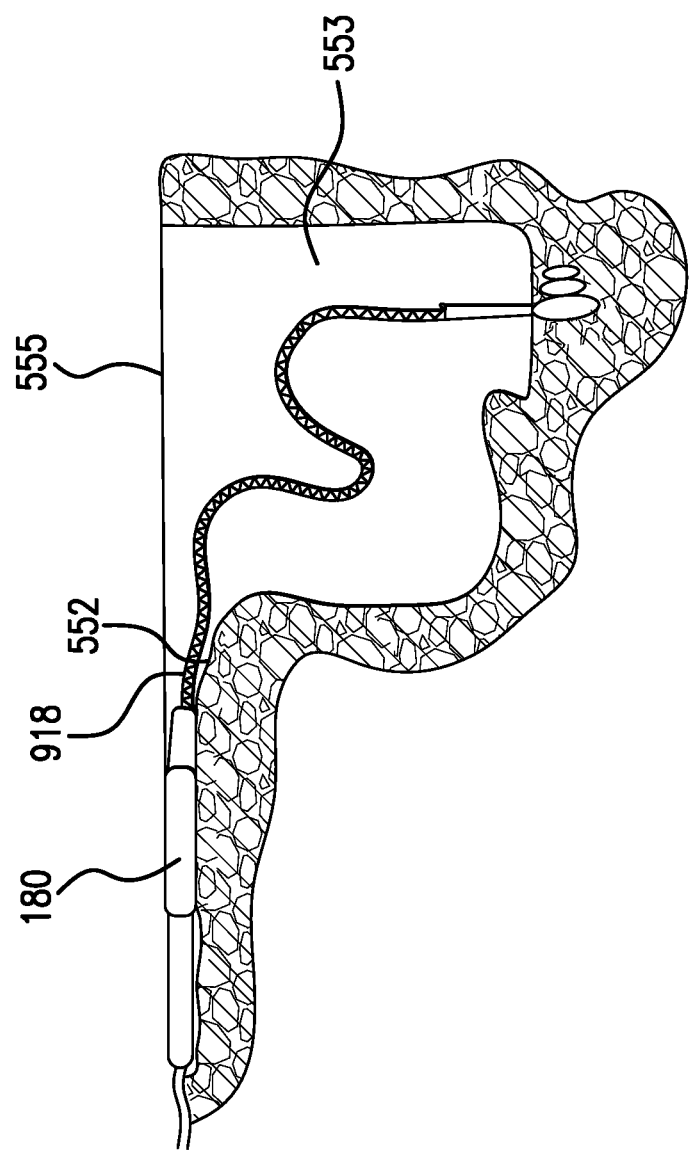
Figure 10E:
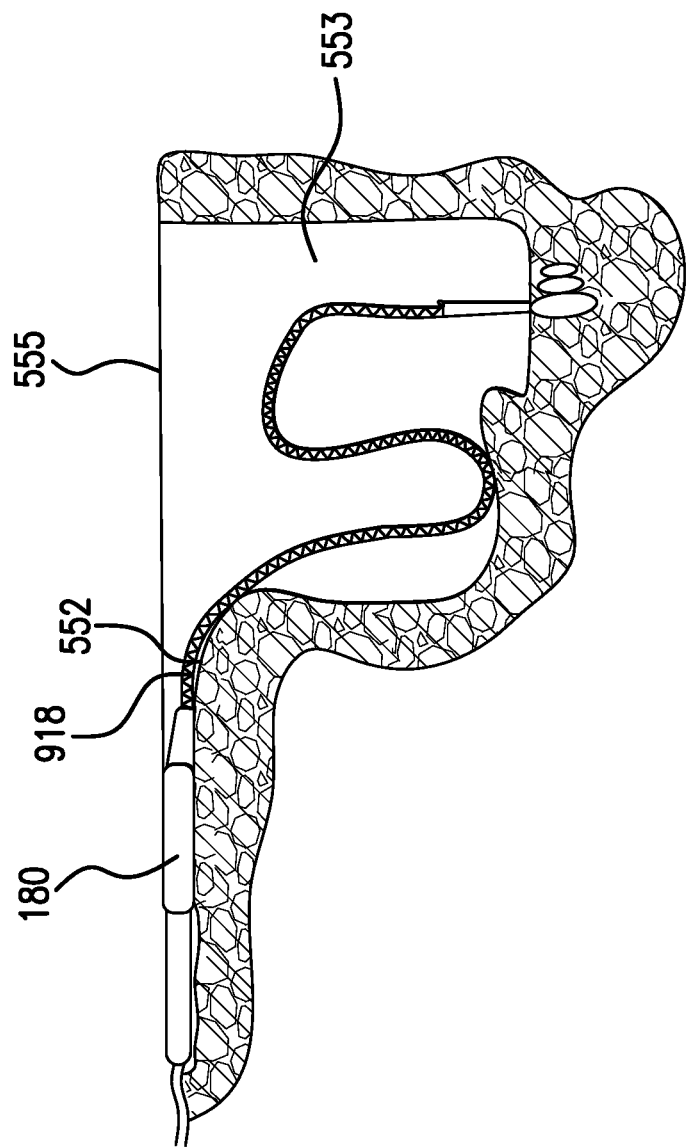

FIG. 10A depicts a side view of an implanted cochlear implant 900B according to an exemplary embodiment, and FIG. 10B depicts a top view of FIG. 10A, showing the mastoid cavity 553 and the middle ear cavity (all skin has been removed for clarity) and the round window 1098 and oval window 1099 of the cochlea, with the stimulating assembly 918B extending into the oval window 1099. Generally, the view of FIG. 10A is corollary to the view of FIG. 5, with some additional details with respect to the surfaces of the mastoid bone that have been removed for implantation of the cochlear implant 900B, and to reflect the fact that an exemplary cochlear implant having the malleable structures detailed herein is utilized.

As can be seen, the receiver/stimulator 180 of cochlear implant 900B lies in bed 551 that is cut into the mastoid bone 550. Dashed line 555 represents the "top" of the mastoid bone with respect to the portions thereof that have not been altered for implantation (i.e., it depicts the background rim of the excavations), and is presented in dashed line format for purposes of clarity. A portion of the lead assembly of the stimulating assembly 918B lies in the channel 552. However, the portion of the lead assembly immediately proximate to the channel's exit into the mastoid cavity 553 is bent downward to follow the contour of the surface of the mastoid cavity. In conceptual terms, the lead assembly flows like water over a waterfall (although it can veer to the left or the right, as indicated by FIG. 10B, where the direction of flow is from the channel 552 into the mastoid cavity 553). In some embodiments, the bottom surface of the lead assembly remains in contact with the mastoid bone at least proximate to the exit of the channel 552. In some embodiments, the bottom surface of the lead assembly remains at least generally in contact with the mastoid bone at least for a distance of about 1 mm, about 2 mm, about 3 mm, about 4 mm, about 5 mm, or about 6 mm or any value or range of values therebetween in about 0.1 mm increments, with respect to a distance from the exit of the channel 552 into the mastoid cavity 553. In this exemplary embodiment, there is no retention between the channel exit and the surface of the cochlea with respect to the lead assembly (e.g., no fasteners or fixtures holding the lead apparatus in place between those locations, etc.). Still further, in some exemplary embodiments, no part of the mastoid bone or the anatomy forming the middle ear cavity (other than the entrance to the cochlea, if indeed that is deemed part of the middle ear cavity) provides positive resistance to movement of the lead assembly (e.g., due to the overhang), and, in some exemplary embodiments, no part of the mastoid bone or the anatomy forming the middle ear cavity (other than the entrance to the cochlea, if indeed that is deemed part of the middle ear cavity) provides any resistance to movement of the lead assembly (e.g., due to friction forces).

In an exemplary embodiment, the stimulating assembly is configured so as to retain the stimulating assembly within the mastoid cavity entirely due to its own structure without any intervening forces or other resistance from the anatomy of the recipient between the location of the exit of the channel and the entrance of the cochlea (although a portion of the stimulating assembly could still be in contact with the anatomy—it just does not need to be in such contact to achieve the aforementioned functionality). Still further, in an exemplary embodiment, any or all of the aforementioned functionalities can be achieved without looping the stimulating assembly.

An exemplary embodiment includes a stimulating assembly that is configured to achieve any or all of the aforementioned functionalities Thus, in an exemplary embodiment, the portion of the stimulating assembly extending between the exit of the channel 552 and the entrance of the cochlea (or at least the portion that corresponds to the helix region) is otherwise free to move but for the fact that the malleable structure prevents such movement or otherwise resists such movement, and for the influence of the cochlea and the channel on the stimulating assembly. In an exemplary embodiment, the portion of the stimulating assembly extending between the exit of the channel 552 and the entrance of the cochlea (or at least the portion that corresponds to the helix region) is oriented substantially entirely due to the malleable structure and due to the channel and due to the cochlea (which includes a scenario where there is a portion that does not include the malleable structure—that portion still being oriented due to the malleable structure owing to the fact that the malleable structures establish a trajectory of that portion).

In an exemplary embodiment, the portion of the stimulating assembly extending between the exit of the channel 552 and the entrance of the cochlea (or at least the portion that corresponds to the helix region) is subjected to a restraining force due entirely to the malleable portion and the channel and the cochlea. In an exemplary embodiment, the portion of the stimulating assembly extending between the exit of the channel 552 and the entrance of the cochlea (or at least the portion that corresponds to the helix region) is unrestrained from moving out of the mastoid cavity/upwards towards the inside of the skin by the anatomy of the recipient (save for the influence of the channel and the cochlea).

In some embodiments, the bottom surface of the lead assembly is not in contact with the mastoid bone within the mastoid cavity 553 after exiting the channel 553 within the aforementioned dimensions, but the lead assembly substantially parallels the surface thereof.

FIGS. 10C-F depict some exemplary arrangements of the stimulating assembly after implantation into the recipient.

The aforementioned bending downward is established at bend numeral 1010, which is established by bending or otherwise deforming structure 610 at that location so that it follows the contours of the mastoid bone and extends downward as shown. In an exemplary embodiment, this can be achieved by gripping the stimulating assembly with a pair of tweezers and imparting a twist on to the tweezers thus bending the stimulating assembly such that the malleable structure to forms. The structure 610 establishes the general trajectory of the lead assembly at this relevant area, and thus owing to the properties of the other portions of the lead assembly, the lead assembly generally stays within the mastoid cavity 553, and does not have a tendency to rise above line 555. That said, owing to the fact that this embodiment utilizes cochlear implant 900B, which includes structure 920, a second bend in the lead assembly can be located at bend 1020, which again establishes a trajectory of the lead assembly at this relevant area, thus further maintaining the lead assembly within the mastoid cavity 553. Again, this can be achieved utilizing a pair of tweezers and subjecting the tweezers to the aforementioned twisting, which bends the stimulating assembly, and thus the forms the malleable structure.

It is noted that the bending of the malleable structures detailed herein can occur anywhere along the length thereof. Any bending of the malleable structures that will resist movement of the lead assembly or otherwise maintain or establish a position of the lead assembly such that it remains below the line 555 of the mastoid cavity can be utilized in at least some exemplary embodiments to practice some embodiments.

Accordingly, an exemplary embodiment includes an implanted cochlear implant having a lead assembly having portions corresponding at least generally to the orientations depicted in the figures herein. However, it is noted that other orientations can be utilized as well. Any orientation of the lead assemblies that is established according to the malleable structures detailed herein and/or other types of structures that can enable the teachings detailed herein can be utilized in at least some exemplary embodiments. Corollary to this is that an exemplary embodiment includes methods of implanting a cochlear implant to have such orientations. In this regard, some exemplary methods will now be described.

Figure 11B:
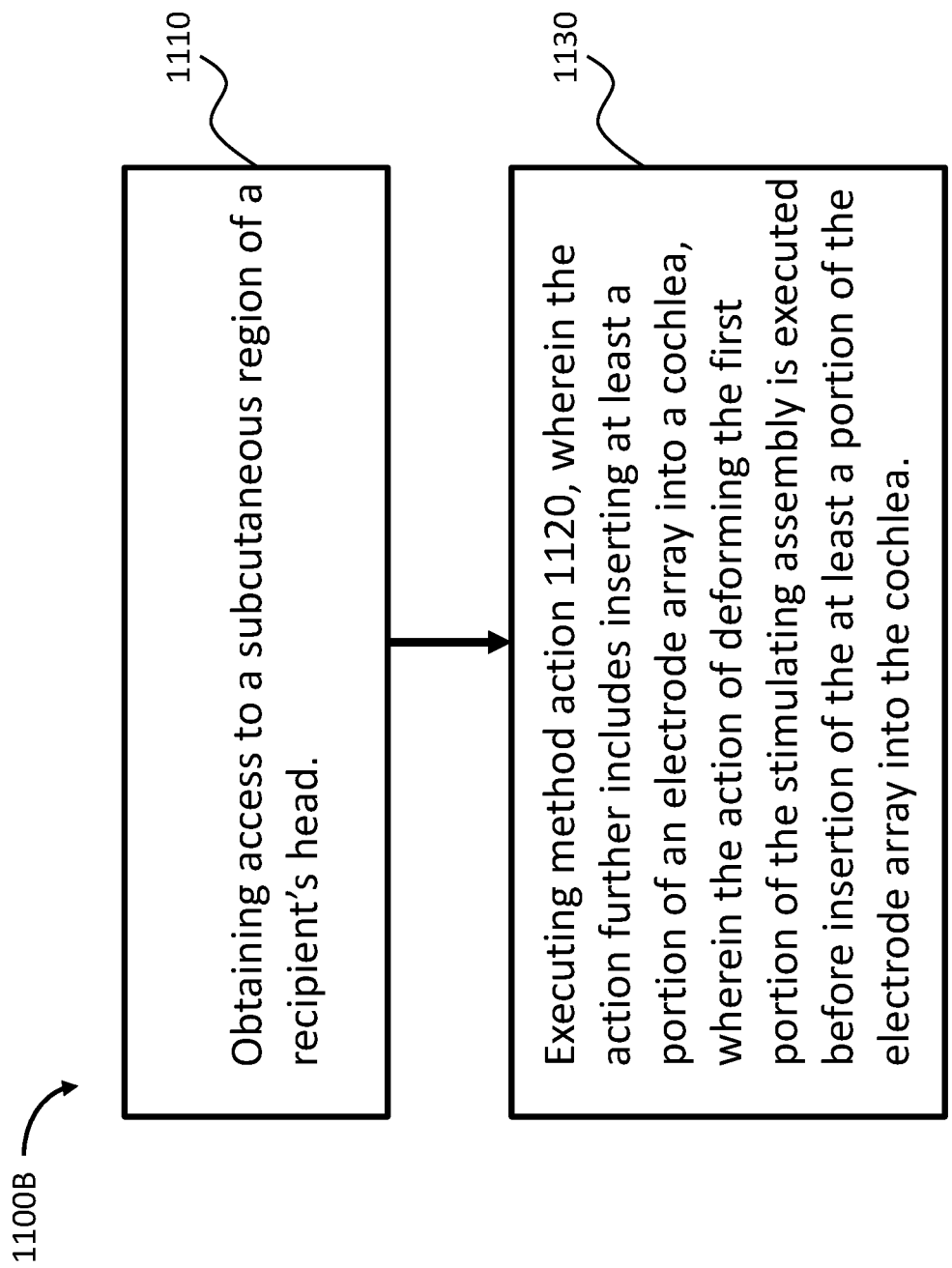
FIG. 11B is a flowchart according to another exemplary method.

FIG. 11A depicts a flowchart for an exemplary method 1100A, which includes method actions 1110 and 1120 (it can include other method actions). Method action 1110 entails obtaining access to a subcutaneous region of a recipient's head. In an exemplary embodiment, this can entail cutting into the skin of the recipient to reach the mastoid bone. In an exemplary embodiment, this can further entail excavating the portions of the mastoid bone to establish the mastoid cavity, the bed, and the channel, etc. That said, in an alternate embodiment, method action 1110 can be executed by obtaining access to a subcutaneous region, the path to which was previously established by another entity. That is, the person executing method action 1110 need not necessarily be the person to cut into the recipient and/or excavate the portions of the mastoid bone, etc. After executing method action 1110, method action 1120 is executed, which entails implanting a stimulating assembly at the subcutaneous region, wherein the action of implanting the electrode assembly includes plastically deforming a first portion of the stimulating assembly so as to maintain the first portion now deformed at a first orientation due to the deformation of the first portion. In an exemplary embodiment, this entails establishing the bend 1010 detailed above, or any of the other bends detailed herein and/or variations thereof.

Method 1100B depicts a variation of method 1100A, or more accurately, an expansion thereof. Method 1100B includes method action 1110, which is identical to that of method 1100A. Method 1100B further includes method action 1130, which entails executing method action 1120, wherein the action further includes inserting at least a portion of an electrode array into a cochlea. In method action 1130, the action of deforming the first portion of the stimulating assembly is executed before insertion (at least full insertion) of the at least a portion of the electrode array into the cochlea.

That said, in an alternate embodiment, method action 1130 entails executing method action 1120, wherein the action also further includes inserting at least a portion of an electrode array into a cochlea, except that the action of deforming the first portion of the stimulating assembly is executed after insertion of the at least a portion of the electrode array into the cochlea. The remaining portion of the electrode array is then inserted into the cochlea. Indeed, in at least some exemplary embodiments, any order of actions that can enable the teachings detailed herein and/or variations thereof to be practiced can be utilized in at least some exemplary embodiments.

Still further, keeping in mind that in the current described exemplary methods, cochlear implant 900B is being implanted, in some exemplary actions of implanting the stimulating assembly includes plastically deforming a second portion of the stimulating assembly so as to maintain the second portion now deformed at a second orientation due to the deformation of the second portion. In this regard, this can entail establishing bend 1020. However, it is noted that this can also be executed utilizing any of the other cochlear implants detailed herein. This can be achieved via cochlear implant 900A, or cochlear implant 600. That is, the various bends can be established in the same malleable structural component, just at different portions thereof.

Note further that in an exemplary method, the action of deforming the first portion of the stimulating assembly is executed before insertion of the at least a portion of the electrode array into the cochlea, and the action of deforming the second portion of the stimulating assembly is executed after insertion of the at least a portion of the electrode array into the cochlea.

Note further that in an exemplary method, the action of deforming the first portion of the stimulating assembly is executed before insertion of the at least a portion of the electrode array into the cochlea, and the action of deforming the second portion of the stimulating assembly is also executed before insertion of the at least a portion of the electrode array into the cochlea.

Note further that in an exemplary method, the action of deforming the first portion of the stimulating assembly is executed after insertion of the at least a portion of the electrode array into the cochlea, and the action of deforming the second portion of the stimulating assembly is also executed after insertion of the at least a portion of the electrode array into the cochlea.

Note further that in some exemplary embodiments, subsequent actions of deforming a third or fourth portion can be executed before and/or after the insertion of the at least a portion of the electrode array to the cochlea. Note further that previously deformed portions can be re-deformed, such as before insertion of the at least a portion of the electrode array into the cochlea and/or after insertion of the at least a portion of the electrode array into the cochlea.

Still further, in an exemplary method, the accessed subcutaneous region need not include the channel 552 in the mastoid bone 550 of the recipient leading to the mastoid cavity 553, although in the current exemplary methods, the channel is present. In at least some of these exemplary embodiments, the mastoid cavity is part of a cavity that also includes the middle ear cavity, which combined cavity is bounded in part by a round and an oval window of a cochlea of the recipient. With this as background, the action of implanting the electrode assembly includes placing the first portion of the stimulating assembly into the artificial channel 552 such that a first sub-portion is located in the channel and a second sub-portion extends from the channel into the mastoid cavity. In this exemplary embodiment, the action of deforming the first portion of the stimulating assembly entails bending the first portion such that the second sub-portion is moved from a first orientation relative to the first sub-portion to a second orientation relative to the first sub-portion, and the plastic deformation maintains the second sub-portion at the second orientation (e.g., the orientation established by bend 1010 of FIG. 10A). In view of the various figures detailed herein, it can be seen that in some exemplary embodiments, the resulting second orientation is such that a longitudinal axis of the second sub-portion is at least about 45 degrees from a longitudinal axis of the first sub-portion. This angle can be represented by $\theta$ in FIG. 10F. In some exemplary embodiments, the resulting second orientation is such that a longitudinal axis of the second sub-portion is at least about 60 degrees from a longitudinal axis of the first sub-portion. In some exemplary embodiments, the resulting second orientation is such that a longitudinal axis of the second sub-portion is at least about 75 degrees from a longitudinal axis of the first sub-portion. In some exemplary embodiments, the resulting second orientation is such that a longitudinal axis of the second sub-portion is at least about 80 degrees from a longitudinal axis of the first sub-portion. In some exemplary embodiments, the resulting second orientation is such that a longitudinal axis of the second sub-portion is at least about 85 degrees from a longitudinal axis of the first sub-portion.

Figure 12:
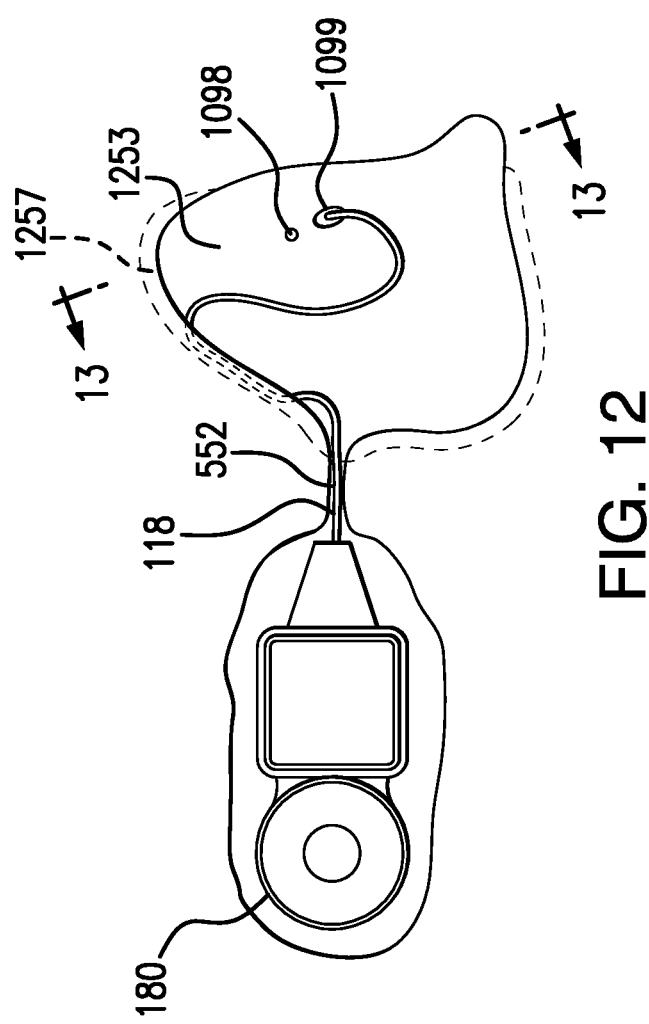
FIG. 12 is a top-view of a portion of the anatomy of a human along with another exemplary embodiment.
Figure 13:
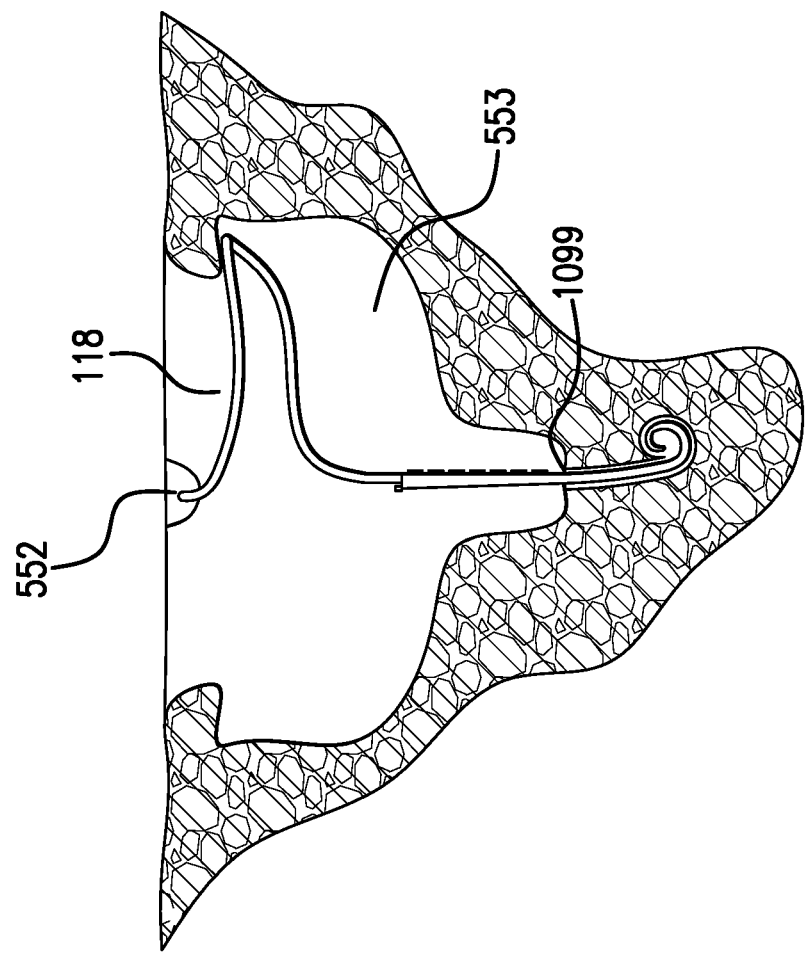
FIG. 13 is a side view of a portion of the anatomy of a human along with another exemplary embodiment.

It is noted that some exemplary embodiments can have utilitarian value in that the lead assembly of the cochlear implants can be maintained in the mastoid cavity without the use of a so-called bony overhang. In this regard, FIG. 12 depicts a top view of an alternate embodiment to implanting a stimulating assembly according to the teachings detailed herein, depicting bony overhang 1257, with FIG. 13 depicting the accompanying cross-sectional side view of a portion thereof. Here, unlike the mastoid cavity 553 above, mastoid cavity 1253 includes bony overhang 1257. In an exemplary embodiment, during the establishment of the mastoid cavity by removing bone of the mastoid bone, the surgeon or other health care professional leaves a bony overhang 1257. In an exemplary embodiment, this bony overhang is utilized to maintain or otherwise provide resistance against the lead assembly 181 from springing out of the mastoid cavity 1253 owing to the aforementioned elasticity detailed above or other phenomenon. In this regard, as can be seen, the lead assembly 181 can be tucked underneath the bony overhang 1257. That said, in some exemplary embodiments, the various method actions detailed herein can include executing one or more or all of the methods detailed herein without placing any portion of the stimulating assembly against any bone overhanging the mastoid cavity. Corollary to this is that in an exemplary embodiment, the methods detailed herein include the action of securing a portion of the stimulating assembly located between an intracochlear electrode and a receiver/stimulator connected to the stimulating assembly in a mastoid cavity without contacting a bony overhang of the mastoid cavity. Note further, that in an exemplary embodiment, the methods detailed herein can include establishing a mastoid cavity, wherein upon the establishment of the mastoid cavity, no bony overhang is present. This is because the exemplary embodiments detailed herein can, in some instances, alleviate any utilitarian value with respect to the aforementioned bony overhang.

It is noted that the aforementioned method actions are but exemplary. Other exemplary methods include other method actions and/or variations of the actions detailed herein. Any method that can enable the teachings detailed herein and/or variations thereof to be practiced can be utilized in at least some exemplary embodiments. Any of the configurations/orientations detailed herein of any other components of the disclosed cochlear implants correspond to a disclosure of a method for placing the stimulating assembly is into those configurations.

Some alternate configurations of the malleable structures will now be detailed.

FIG. 14 presents a side view of an exemplary alternate embodiment, and FIG. 15 depicts a cross-sectional view thereof. Briefly, it is noted that as with the embodiment of FIG. 7, there exists an elongate stimulation assembly of a cochlear implant (or other implantable stimulation device), comprising an intra-cochlear portion including an array of electrodes, and lead wires 1489 (only one is shown, in FIG. 14, for purposes of clarity, but more are shown in FIG. 15) extending from the intra-cochlear region in electrical communication with the array of electrodes, the lead wires being located in an elongate lead body 1483. As with the embodiment of FIG. 7, the elongate stimulation assembly includes a malleable component 1210 extending in an elongate manner at least partially along with the lead wires 1498. As with FIG. 7, the malleable component 1210 is located closer to an outer surface of the lead body 1483 than at least one of the lead wires 1498.

It is further noted that in an exemplary embodiment, the malleable component is located the same distance from an outer surface of the lead body as at least one of the lead wires.

In the exemplary embodiment of FIG. 14, the malleable component 1210 is also a metallic wire. However, whereas the malleable component 1210 was embedded in the body 1483 (e.g., embedded in the silicone in which the wire leads were also embedded), or otherwise located within a conduit forming the lead body, in this embodiment, the malleable component 1210 is located outside the body/outside the silicone. In an exemplary embodiment, the malleable component 1210 is bonded to the body 1483. In an exemplary embodiment, the malleable component 1210 is mechanically attached in some manner to the body 1483. By way of example only and not by way of limitation, surgical sutures or metal bands or silicone bands, or plastic bands can extend about the body 1483 while also encompassing the malleable component 1210. Any arrangement that can enable sufficient portions of the body 1483 to be coupled to the malleable component 1210 so that the teachings detailed herein and/or variations thereof can be enabled and practiced can be utilized in at least some exemplary embodiments. In an exemplary embodiment, by way of example only and not by way of limitation, the malleable component or otherwise the stiffening material located outside the body/outside the silicone, could be used, in some exemplary embodiments, as an extra-cochlear electrode. In an exemplary embodiment, the entire malleable component could be used as such, at least the portions thereof that are located outside the body/silicone. That said, in an alternate embodiment, the malleable component could be insulated or otherwise provided with a coating, but a portion of this insulation and/or coating could be not present, thus exposing the malleable component within the coating to the ambient environment so that this exposed portion can be utilized as the extra cochlear electrode. In a similar vein, in an exemplary embodiment, the portion of the malleable component expose the ambient environment can be utilized as the return electrode. Accordingly, in an exemplary embodiment, the malleable component could extend to the receiver stimulator of the implanted cochlear implant. That said, in an alternate embodiment, the malleable component may and prior to extending to the receiver your stimulator component, but the malleable component can still be in electrical communication with the receiver stimulator component. For example, a separate electrical lead wire separate from the stimulating leads could extend from the receiver stimulator, but instead of extending to the electrodes of the electrode array, could extend to the malleable component.

It is noted that the longitudinal axis 1499 has been "moved" relative to axis 1299 to account for the fact that the overall outer diameter of the stimulating assembly has been extended, thus the center thereof has been moved downward owing to the placement of the malleable component outside the body.

Briefly, it is noted that the wire leads 1489 are arrayed in a helical structure, as seen. To be clear, while the embodiment of FIG. 14 depicts the malleable component 1210 located on the outside of the body 1483, an alternate embodiment can utilize the helical wires along with the malleable component 1210 embedded in the body 1483. That is, the current application has been presented in an efficient matter to convey the various concepts, but it is to be understood that some embodiments entail combining concepts of one embodiment with concepts of another embodiment. Indeed, some exemplary embodiments entail a combination of one or more features from one embodiment with one or more features of another embodiment unless otherwise indicated or otherwise impractical to do so.

In view of FIGS. 14 and 15, it can be seen that in some exemplary embodiments, the extra-cochlear portion of the stimulating assembly includes a lead body, and the malleable component is a metal wire located completely outside the lead body. It is further noted that in some exemplary embodiments, the malleable structure is located completely away from the lead body in an offset manner. Connection brackets or the like can be utilized to place the lead body into mechanical connection with the malleable structure (e.g., posts can be located every millimeter or so along the length of the malleable structure, etc.).

In view of FIGS. 14 and 15, an exemplary embodiment includes a stimulating assembly where the extra-cochlear portion includes a lead body 1483, and the malleable component 1210 is a metal wire located at least partially external to the lead body 1483 attached to the lead body 1483. FIG. 16A depicts another example of such an embodiment, where the malleable component 1210 is partially embedded in the body 1483. Corollary to the above, exemplary embodiments include embodiments where the malleable component is a metal wire located at least partially external to the lead body and attached to the lead body. FIG. 16B depicts full embedding, where the body includes extra material to encapsulate the malleable structure.

FIG. 17 depicts an alternate embodiment of the arrangement of FIG. 16, where the lead wires 1498 and malleable component 1210 have been rotated 90° in a clockwise direction relative to that which is the case in FIG. 16A. That is, the malleable component 1210, instead of being located at the bottom of the body of 1483, is located to the side of the body 1483 (relative to the frame of reference where the bottom corresponds to the portion closest to the bottom of the channel formed in the mastoid bone, etc.). It is further noted that in at least some exemplary embodiments, the malleable component 12 can be located on the other side of the longitudinal axis 1499 relative to that which is depicted in FIG. 17. Note further, that in an exemplary embodiment, the various components could have been rotated 180° relative to that which is the case depicted in FIG. 16A. That is, the malleable component 1210 can be located on the top of the body 1483. Note further, other orientations of the malleable component and/or other components can be utilized (e.g., the malleable component could be located at the 7:30 position, the 10:30 position, or any other position that can have utilitarian value).

FIG. 18 presents yet another alternative embodiment, where two malleable components 1210 are located on opposite sides of body 1483. While this dual-malleable component embodiment is depicted with respect to the malleable components being located at the 3 o'clock position and that the 9 o'clock position, in alternative embodiments, the malleable components can be located at the 12 o'clock position and at the 6 o'clock position or any other positions for that matter. Note further that the positioning need not necessarily be symmetric about the longitudinal axis 1499. Additionally, three or more malleable components can be utilized. Further, the malleable components need not necessarily be identical. In some embodiments, one of the malleable components can have a larger diameter than the other malleable component. Moreover, it is noted that the material properties of one malleable component can be different than the material properties of another malleable component (e.g., one could be made of one material and one could be made from another material). Additionally, one of the malleable components could be at least partially embedded in the body 1483, while one other of the malleable components could be completely outside the body 1483. Still further, in an exemplary embodiment, both of the malleable components can be at least partially within the body 1483, and in some embodiments, all of the malleable components are completely within body 1483. Again, any arrangement that can enable the teachings detailed herein and/or variations thereof to be practiced can be utilized in at least some exemplary embodiments.

In view of FIG. 18, in an exemplary embodiment, there is a cochlear implant that is configured to prevent the movement of the at least a portion of the lead assembly due to the elasticity via a plurality of malleable wires co-located with the lead assembly. In this exemplary embodiment, the plurality of wires are located outside the lead assembly extending parallel thereto and extend through a same plane that is normal to a local direction of extension of the lead assembly.

FIG. 19 depicts another alternate embodiment, where the malleable structural component is a tube 1910 that encompasses the body of the lead assembly. In an exemplary embodiment, the tube 1910 is configured so as to avoid collapsing upon bending. It is noted that while the embodiment of FIG. 19 depicts the tube 1910 on the outside of the body of the lead assembly, in an alternate embodiment, the tube can be implanted in the body of the lead assembly.

Thus, in an exemplary embodiment, there is a cochlear implant configured to prevent the movement of the at least a portion of the lead assembly due to the elasticity via a structure co-located with the lead assembly, wherein the structure is a tube extending about the lead apparatus.

Still further, in an exemplary embodiment, implantation of an implant utilizing the arrangement of FIG. 19 can entail a method of bending the stimulating assembly by an amount limited to the amount beyond which crimping and/or collapsing of the tube 1910 would result. Still further, in an exemplary embodiment, the tube can be asymmetrical about the longitudinal axis 1499. Such an exemplary embodiment can be seen in FIG. 20, where the wall thickness at the bottom of tube 2010 is thinner than the wall thickness at the top of tube 2010. In an exemplary embodiment, this can avoid the aforementioned collapsing and/or crimping, or at least mitigate the effects thereof. Indeed, in an exemplary embodiment, a portion of the tube can be configured to separate from another portion (e.g., split), so as to avoid the collapsing/crimping phenomenon. Still further, in an exemplary embodiment, the tube includes a break zone configured to separate upon the bending. In an exemplary embodiment, the break zone is an area of relatively thinner wall thickness relative to the wall thicknesses of other components of the tube. That said, in an alternate embodiment, the tube can have a slit therein running parallel to the longitudinal axis 1499 so that upon bending, the portions forming walls of the slit can expand from one another so as to avoid or otherwise alleviate the aforementioned collapsing and/or crimping.

Corollary to the above is that a portion of a tube structure can be utilized/a C-shaped structure can be utilized as the malleable component. In this regard, FIG. 21 depicts another exemplary embodiment of a malleable structure 2110 in the form of a C-shaped elongate component (elongate in the direction of the longitudinal axis 1499). As can be seen, the malleable structure 1210 extends about a portion of the body of the lead assembly. While the embodiment depicted in FIG. 21 depicts a C-shaped structure that subtends an angle of about 170° about the longitudinal axis 1499, in some alternative embodiments, the angle subtended is less than 170° or greater than 170° (e.g., about 145°, about 270°, etc.). Any arrangement that can enable the teachings detailed herein and/or variations thereof to be practiced can be utilized in at least some exemplary embodiments.

FIG. 22 depicts an alternative embodiment where there is both an outside malleable structure 2110 and a malleable structure 2220 encapsulated in the body of the lead assembly. Thus, an exemplary embodiment entails a plurality of malleable structures, where one of the structures is located further away from the longitudinal axis of the lead assembly than the lead wires. While some exemplary embodiments, such as that depicted in FIG. 22, are such that the body completely separates the malleable structure located outside the body from the malleable structure located inside the body, in some alternate embodiments, the structures are connected to each other by another malleable structure and/or a rigid structure and/or a flexible structure other than silicone, or other structure establishing the bulk of the body of the lead assembly.

Figure 23:
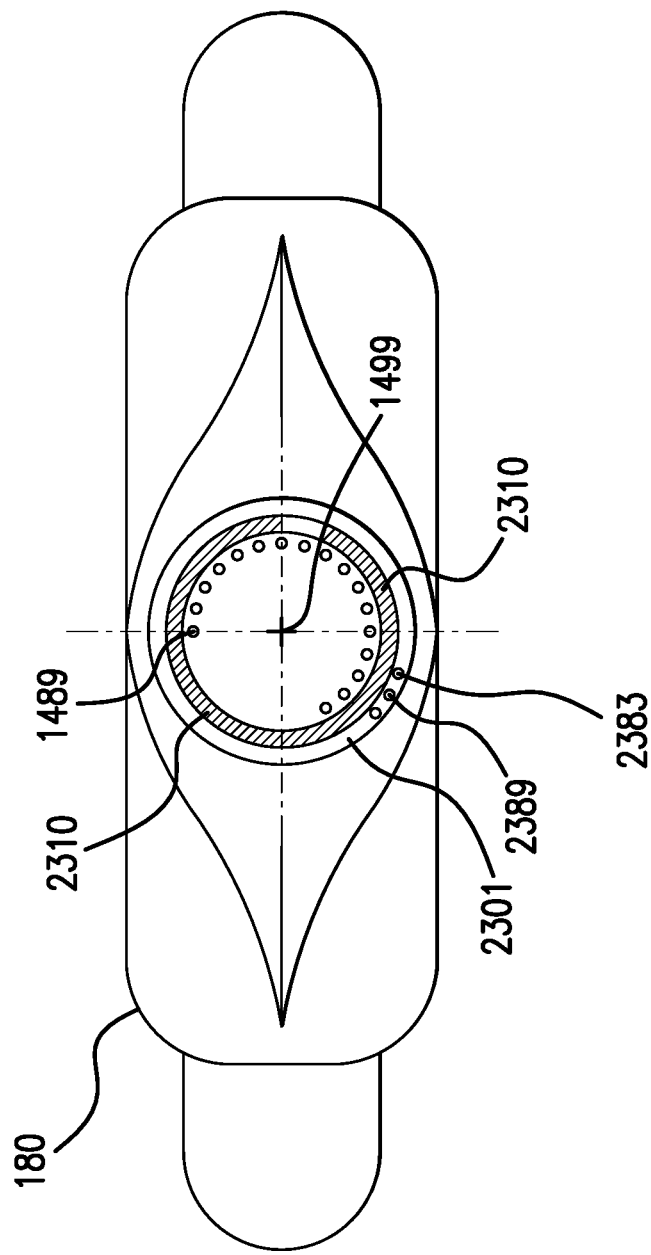
FIG. 23 is a cross-sectional view of another alternate embodiment of the embodiment of FIG. 6.

As noted above, some embodiments can utilize the tube structure embedded in the body of the lead assembly. In this regard, FIG. 23 depicts a malleable structure in the form of a tube 2310 completely embedded in the body 2383 of the lead assembly. Note further that in this exemplary embodiment, the body 2383 includes a portion inside the tube 2310 and a portion located outside the tube 2310, annotated as 2301. In an exemplary embodiment, the portion 2301 is also made of silicone. In an exemplary embodiment, there are holes or passages located through the walls of the tube 2310 such that when the silicone body is molded, the silicone on the outside of the tube 2310 is in the silicone communication with the silicon on the inside of the tube 2310. Note further that in this exemplary embodiment, there are lead wires 2389 located on the outside of the tube 2310 as well as lead wires 1498 located inside the tube 2310. Thus, while in this embodiment, the malleable structure 2310 is still located away from the longitudinal axis 1499 a greater distance than at least one of the lead wires 1498, and is also located closer to the surface of the body 2383 and at least one of the lead wires 1498, there are other lead wires that are located closer to the surface of the body than the malleable structure 2310, and located further away from the longitudinal axis 1499 then the malleable structure 2310.

Figure 25:
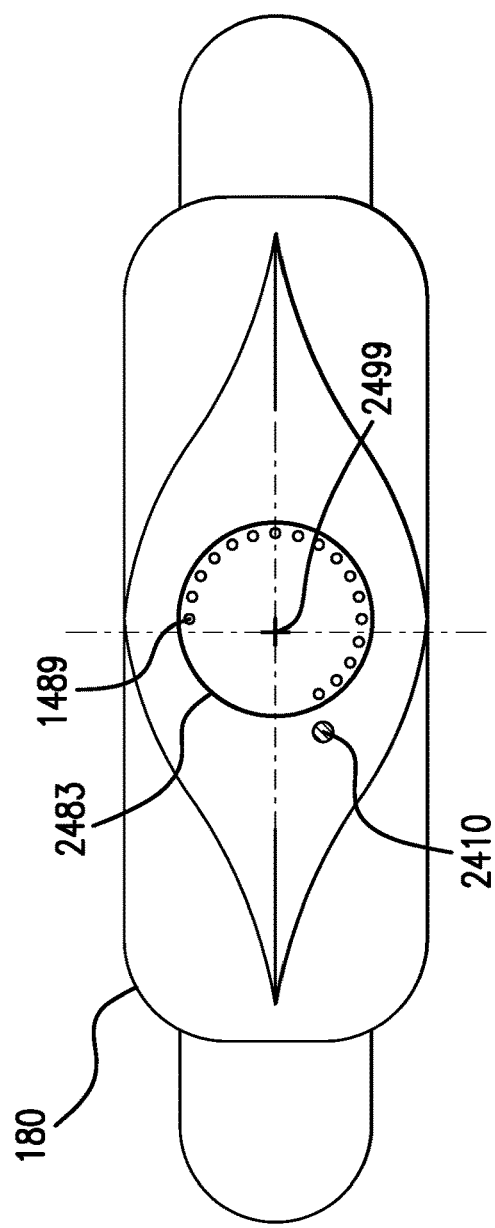
FIG. 25 is a cross-sectional view of the embodiment of FIG. 24.
Figure 24:
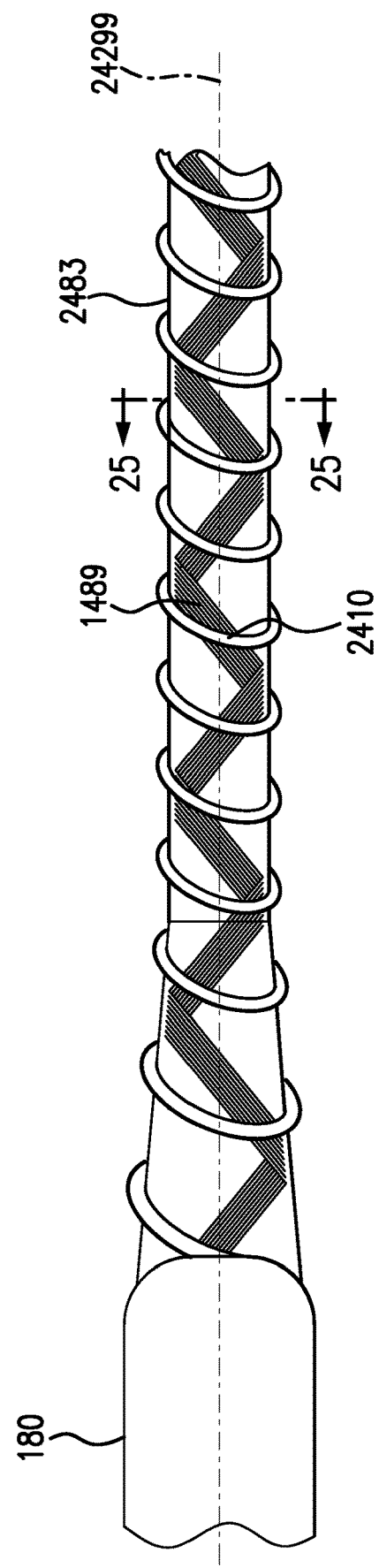
FIG. 24 is a quasi-functional side view of a portion of another embodiment of the embodiment of FIG. 6.

FIGS. 24 and 25 depict an alternate embodiment where the malleable component is a helical structure. More particularly, as can be seen, structure 2410 is a malleable helical structure that extends about the outer surface of the body 1483 of the lead assembly. As can be seen, in this exemplary embodiment, the malleable helical structure is wrapped around at least some of the lead wires 1489, which are also in a helical structure.

In the embodiments of FIGS. 24 and 25, the helical structure extends about the lead body 1483 at least partially external to the lead body. In the embodiments of these figures, the helical structure extends fully externally to the lead body. Here, the helical structure is attached to the surface of the lead body 1483 as can be seen. The attachment can be through bonding or any suitable mechanical structure. That said, in an alternate embodiment, the helical structure itself can be utilized to hold itself to the lead body 2483. That is, because the helical structure winds about the lead body 1483, it will hold itself in place. Along these lines, in an exemplary embodiment, the helical structure that extends about the lead body is configured such that the lead body can move locally relative to the helical structure. That is, the body can move by at least some amount in the longitudinal direction (e.g., in the direction of longitudinal axis 1499) and/or in the lateral direction by at least some amount relative to the helical structure 2410. In at least some exemplary embodiments, this can have utilitarian value where helical structure 2410 prevents the global movement of the lead body 2483. That is, while the lead body 2483 can move locally (e.g., within the confines of the helical structure 2410), the lead body cannot move globally (cannot change the trajectory/orientation of the helical structure 2410, and thus cannot move globally).

It is noted that while the aforementioned movement features are disclosed with respect to a helical structure, in some alternative embodiments, the aforementioned movement features can also be achieved utilizing some other structures. By way of example only and not by way of limitation, the lead body can be flexibly attached to the malleable wires detailed herein so that limited local movement can occur, but no global movement can occur.

While the embodiments of FIGS. 24 and 25 depict the helical structure located outside the lead body, in some alternate embodiments, the helical structure can be embedded within the body. In this regard, FIG. 26 depicts a helical structure 2610 embedded within the body 2683 of a stimulating assembly.

FIGS. 27 and 28 depict an alternate embodiment where the malleable component is again a helical structure. More particularly, as can be seen, structure 2710 is a malleable helical structure that extends inside the body 2783 of the lead assembly. As can be seen, in this exemplary embodiment, the malleable helical structure is a first helix, while the lead wires 1489 are also in a second helix, where the first helix and the second helix form a double helix. As can be seen, the outer diameter of the first helix is about the same as the outer diameter of the second helix.

In the embodiments of FIGS. 27 and 28 the helical structure extends within the lead body 2783, about the longitudinal axis 2799. In the embodiments of these figures, the helical structure extends fully internally to the lead body 2783.

It is further noted that concomitant with the embodiments presented above where two or more malleable structures are utilized, in an exemplary embodiment, the cochlear implants according to at least some exemplary embodiments are configured to prevent the movement of the at least a portion of the lead assembly due to the elasticity via a malleable double helix assembly co-located with the lead assembly. That is, in some embodiments, two separate structures both having separate helix shapes can be utilized. That said, in an alternate embodiment, the double helix can be part of a single structure, where two sub-components have the helix structure, and are connected together by another sub-component. Corollary to this is that the embodiments presented above where the malleable components are two separate structures can also be practiced where the malleable components are part of substructures of the same structure connected together by a third structure.

Note further that in some exemplary embodiments, a double helix structure can be utilized where the lead wires form one of the helixes, and the malleable component forms another one of the helixes. The two helixes can be equidistant from the longitudinal axis of the lead assembly, or, in an alternate embodiment, one of the helixes can be closer to the longitudinal axis than the other of the helixes. In an exemplary embodiment, the malleable helix is located further away from the longitudinal axis, and/or closer to the outer surface of the body of the lead assembly then the helix formed by the lead wires.

Figure 29:
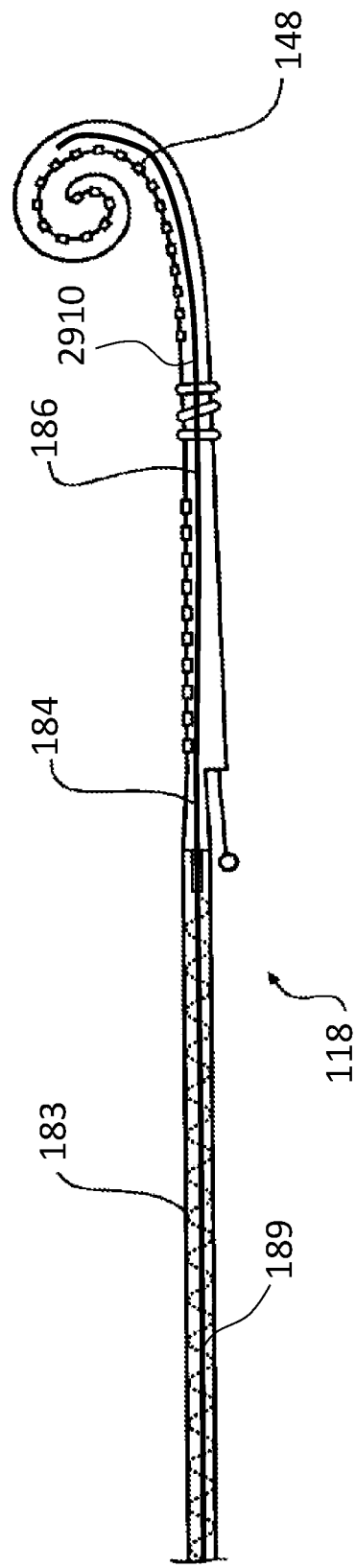
FIG. 29 depicts a schematic according to another exemplary embodiment.

The teachings detailed above have generally been directed towards a structure that is located in the extra cochlear region/outside of the intracochlear region 188 of the elongate stimulating assembly. That is, all of the embodiments detailed above have disclosed the malleable portion/malleable structures being located in the lead assembly. Thus, the distal ends of any of the malleable portions or other structure detailed above to resist movement of a portion of the elongate stimulating assembly have all ended prior to reaching the intra-cochlea region. Indeed, most embodiments detailed above have been disclosed where the distal end of the malleable portion or other structure detailed above to resist movement of a portion of the elongate stimulating assembly of all ended prior to the end of the lead assembly 181 and have not extended into the electrical array 190. FIG. 29 depicts an alternate embodiment where the malleable portion (here, element 2910) extends from the body 183 of the lead assembly into the electrode array 190 in general, and into the intra-cochlea region 188 of the electrode array in particular.

Figure 30:
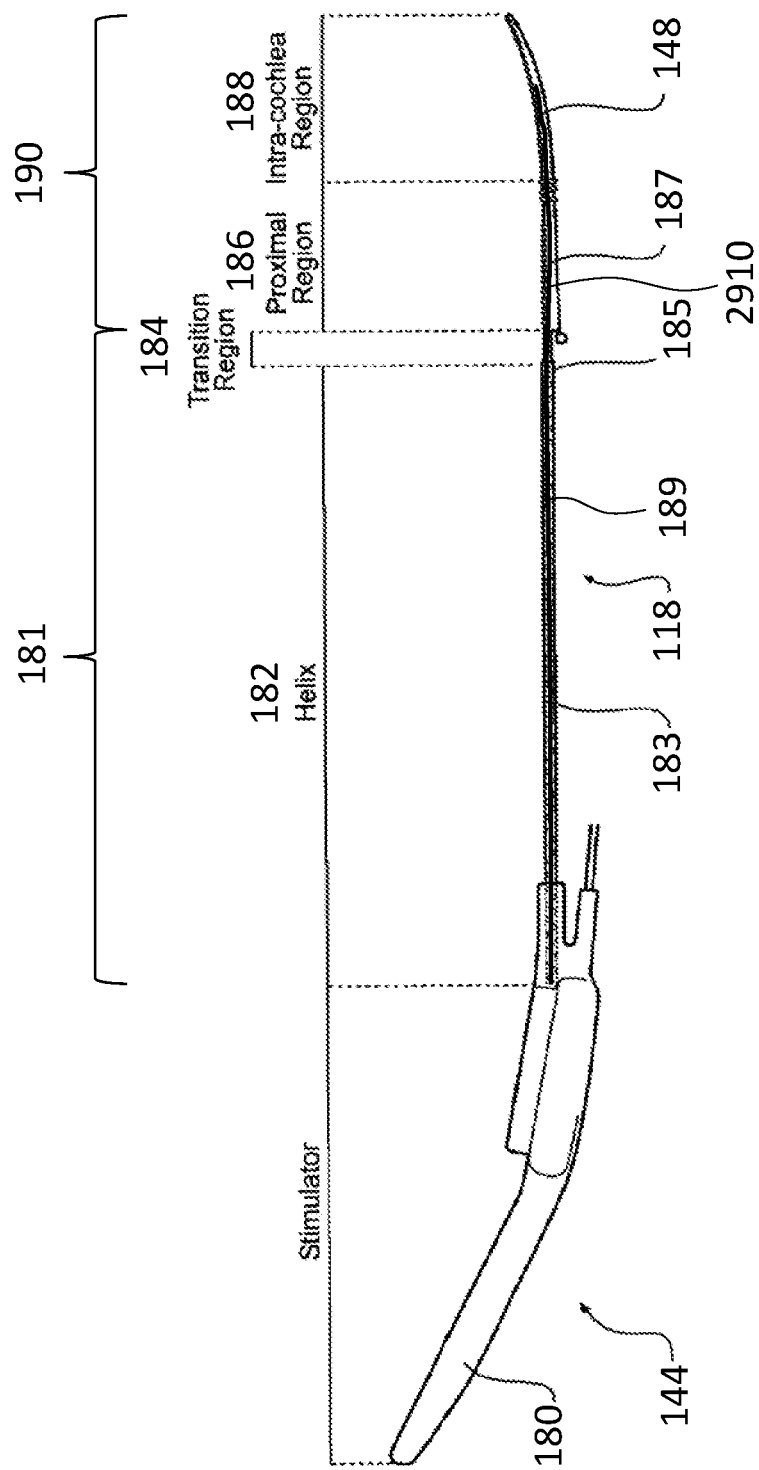
FIG. 30 depicts a schematic depicting additional details of the embodiment of FIG. 29.

FIG. 29 corresponds to FIG. 2 above, except that malleable portion 2910 is located inside the lead assembly and inside the electrode array. In an exemplary embodiment, malleable portion 2910 corresponds to any of the malleable portions detailed above and/or to any of the structures detailed herein that have been disclosed to resist movement of a given portion of the elongate stimulating assembly due to elasticity or the like. FIG. 30 corresponds to FIG. 1B above, except that, as of FIG. 29, malleable portion 2910 is located inside the lead assembly and inside the electrode array. As can be seen, malleable portion 2910 extends all the way from the receiver stimulator 180 to the intracochlear region 188 of the electrode array 190. Thus, in an exemplary embodiment, malleable portion 2910 is an elongated version of structure 910 of FIG. 9A above. That is, in FIG. 9A, the structure 910 extended at least substantially the full length between the receiver/stimulator 180 and the electrode array assembly 190. Here, structure 2910 extends at least substantially the full length between the receiver/stimulator 180 and a location inside the intracochlear region 188 of the electrode array, such that the structure 2910 is located in at least a portion of the intracochlear region 188 of the electrode array.

It is noted that in at least some exemplary embodiments, any of the aforementioned functionalities detailed above with respect to the malleable portions or otherwise structures detailed above that resist movement of the elongate stimulating assembly are applicable to the embodiments where the malleable portions/structures extend into the intracochlear region, both globally, and locally with respect to the portions of the elongate stimulating assembly that include the malleable portion/structure. By way of example only and not by way of limitation, to the extent that some of the embodiments resist movement at, for example, the midpoint of the lead assembly, owing to the fact that the malleable portion is located at the midpoint, the embodiments where the malleable portion or otherwise the structure is located within the intracochlear region also experience the phenomenon of resisting movement, at least with respect to the components that include the malleable portion/structure.

Figure 31:
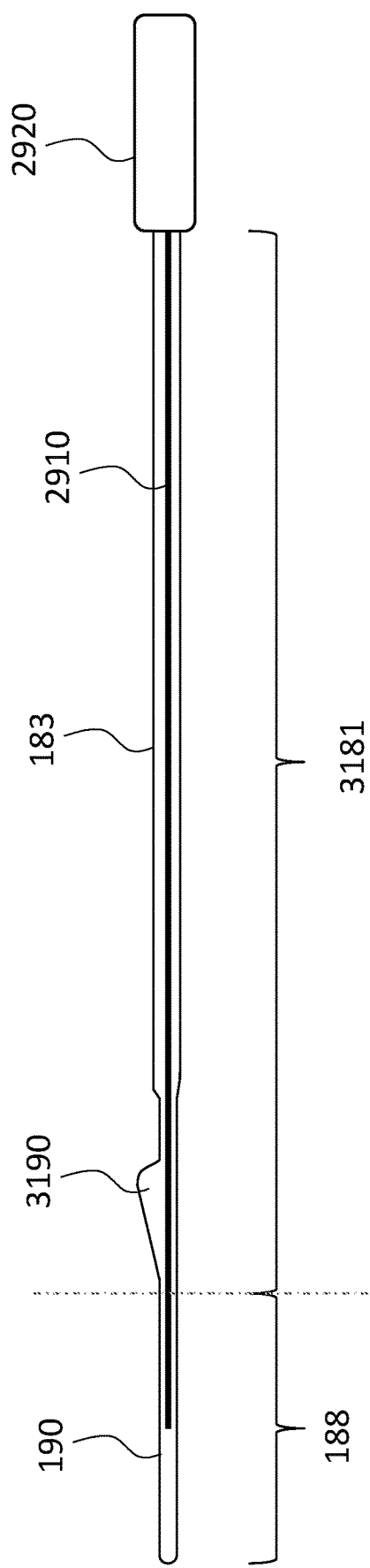
FIG. 31 depicts a schematic depicting a quasi-conceptual view of an exemplary embodiment.

FIG. 31 depicts an exaggerated view of an implantable portion of a cochlear implant for purposes of discussion. The elongate stimulating assembly has been divided into two regions: the intracochlear region 188 and the extra cochlear region 3181. As can be seen, the extra cochlear region 3181 extends from the intracochlear region to the receiver stimulator 2920, which corresponds to the receiver stimulator 180 detailed above. In this exemplary embodiment, structure 2910 extends all the way from the receiver stimulator 2920 to the electrode array, passing gripping nub/gripping wing 3910 (which is utilized so as to provide the surgeon or other healthcare professional a body that can be gripped by a tool or the like during insertion, which body will not be damaged by the compressive forces applied thereto, and which body also provides a good reaction surface to react to torques and the like, along with other utilitarian value as is recognized in the industry) and into the intracochlear region 188. In this exemplary embodiment, the structure 2910 is a monolithic structure that contiguously extends from the receiver stimulator 2920 to the intracochlear region 188. Additional details of the structure will be described in greater detail below. However, it is briefly noted that any of the structures detailed above can be utilized with respect to the embodiments of FIGS. 29, 30 and 31, and any of the other embodiments detailed below unless otherwise specified.

Accordingly, in an exemplary embodiment, there is an elongate stimulation assembly of an implantable stimulation device, such as that depicted in FIG. 31 and the other figures detailed herein. In an exemplary embodiment, this assembly includes an intracochlear portion including an array of electrodes, such as by way of example only and not by way of limitation, intracochlear region 188 of electrode array 190. Still further, in an exemplary embodiment, this assembly includes an extra-cochlear portion extending from the intracochlear portion. With reference to FIG. 31, this is portion 3181. Concomitant with the teachings detailed above, in an exemplary embodiment, the malleable portion, such as malleable portion 2910, extends from the extra cochlear portion to the intracochlear portion such that the extra cochlear portion and the intracochlear portion also include respect to portions of the malleable component.

Figure 32A:
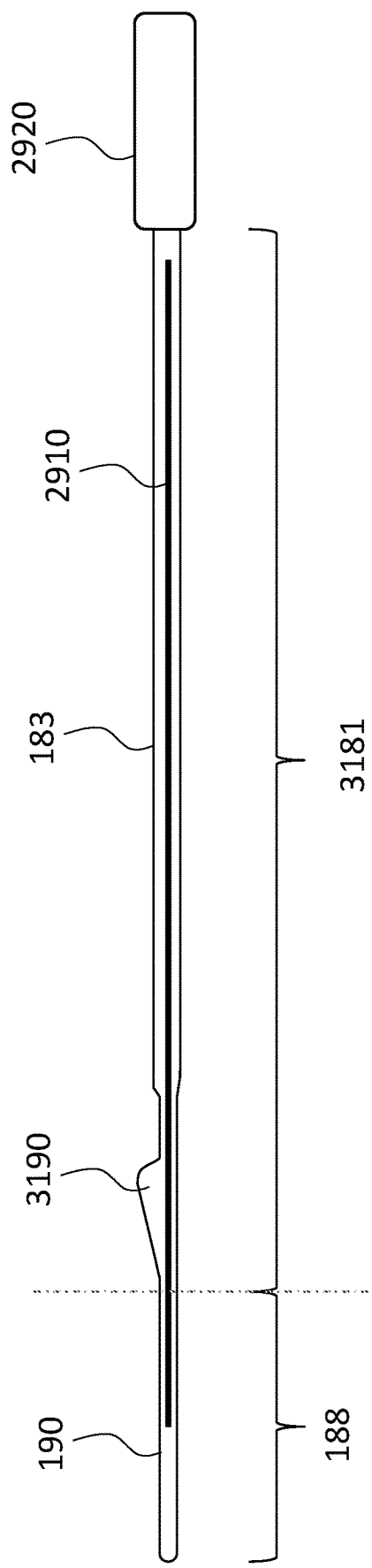
FIGS. 32A-43 depicts schematics depicting quasi-conceptual views of various exemplary embodiments.

The embodiment of FIG. 31 depicts the malleable component 2910 extending from the intracochlear portion 188 all the way to the receiver stimulator 2920. However, in alternate embodiments, the malleable portion 2910 does not extend all the way to the receiver/stimulator. FIG. 32A depicts such an exemplary embodiment, where the malleable portion 2910 extends only to a location that is proximate to the receiver/stimulator 2920. Thus, in an exemplary embodiment, in view of FIGS. 31 and 32A, there is an elongate stimulation assembly that includes a malleable portion that extends at least to a location proximate to a receiver/stimulator.

Figure 32B:
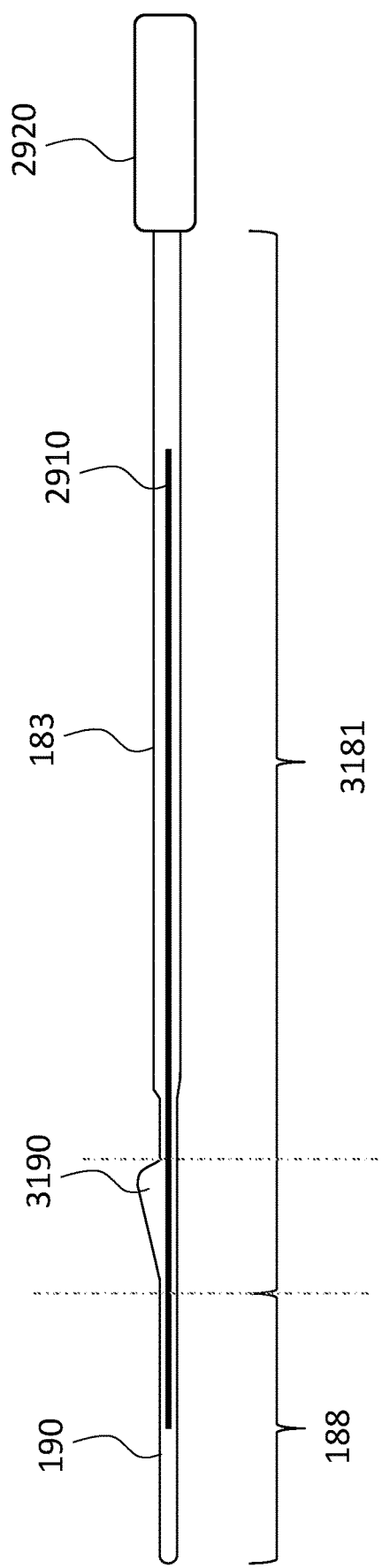

FIG. 32B depicts an alternate embodiment where the malleable portion 2910 does not extend to a location proximate the receiver/stimulator 2920. However, the malleable portion 2920 extends over more than 50% the length of the lead assembly (the portion from the receiver/stimulator 2920 to the beginning of nub 3190, which in this embodiment begins the beginning of the lead assembly 190) and over more than 50% the length of the extra cochlear region 3181 of the elongate stimulation assembly. In an exemplary embodiment, the malleable portion 2910 extends more than 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% of the length of the lead assembly and/or the length of the intracochlear region, and/or extends a length of any value, or range of values therebetween in 0.1% increments the length of the lead assembly and/or the length of the intracochlear region (e.g., extends a length of 33.2% to 88.3% of the intracochlear region and/or the lead assembly, extends 55.5% the length of the lead assembly or the intracochlear region, etc.). In an exemplary embodiment, the malleable portion 2910 extends the entire length.

In an exemplary embodiment, the malleable component extends from the intra-cochlear portion to a location at least proximate a housing containing a stimulator of the implantable stimulating device (e.g., the stimulator of the stimulator receiver 180), or the malleable component extends from the intra-cochlear portion to the housing.

Figure 33:
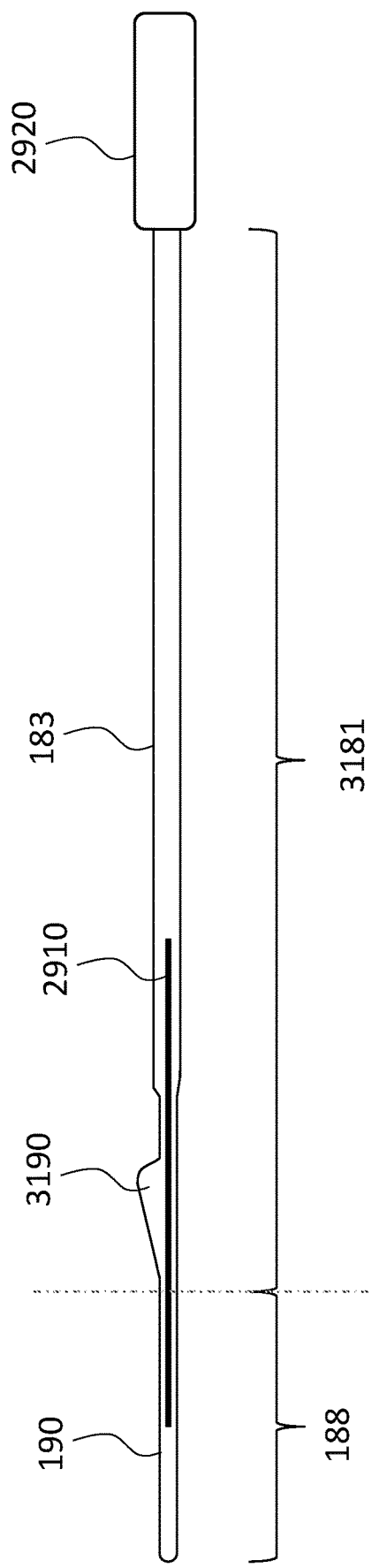

FIG. 33 depicts an exemplary embodiment where the malleable portion 2910 extends a length that is less than 50% of the length of the lead assembly and less than 50% a length of the extra cochlear region 3181. In an exemplary embodiment, the malleable portion 2910 extends less than 10%, 15%, 20%, 25%, 30%, 33.333% ($\frac{1}{3}^{rd}$), 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% of the length of the lead assembly and/or the length of the intracochlear region. In an exemplary embodiment, portion 2910 is a basil stiffener in that it provides stiffness to a basil portion of the intra-cochlear portion of the electrode array.

Figure 34:
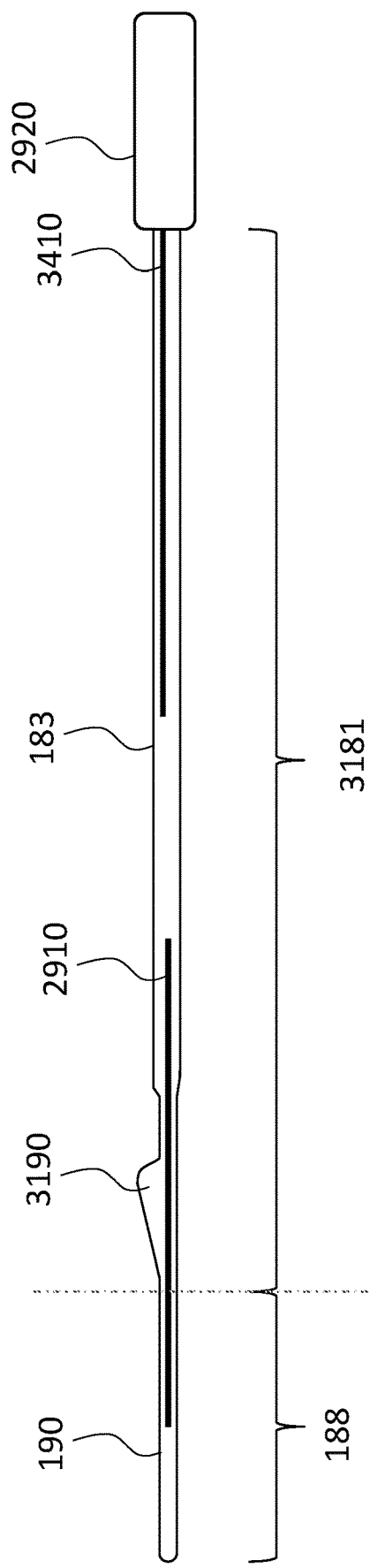

FIG. 34 depicts an alternate embodiment that includes two separate and distinct malleable portions: malleable portion 2910 and the malleable portion 3410. As can be seen, the malleable portions are separated by a space. Thus, in an exemplary embodiment, there is an elongate stimulation assembly according to the teachings detailed above, that further includes a second malleable component 3410 that is separate from the malleable component 2910 that extends to the intracochlear portion of the elongate stimulating assembly/that is located in the intracochlear portion. As can be seen, the second malleable component 3410 is longitudinally spaced away from the malleable component 2910 that extends to the intracochlear portion. By longitudinally spaced away from the malleable component, it is meant that there is a space in the longitudinal direction of the elongate stimulating assembly where neither the malleable portion 2910 nor the malleable portion 3410 or present. (It is noted that such an embodiment can include a third malleable portion located in such space, although in some other embodiments, it is noted that the space can be free of any malleable component.)

FIG. 34 also depicts that the malleable component 2910 is laterally spaced away from the malleable component 3410. That is, as can be seen, with the frame of reference of FIG. 34, malleable portion 3410 is located "higher" than malleable portion 2910. Note also that in some embodiments, not only are the malleable components not aligned in the vertical lateral component, in some other embodiments, the malleable components are not aligned in the lateral component extending in and out of the page that constitute to the frame of reference of FIG. 34. That said, in some alternate embodiments, the malleable portions are laterally aligned with one another in one dimension (any of the two) or laterally aligned in both dimensions. Note also that in some exemplary embodiments, the malleable portions about one another such that there is no space in the longitudinal direction between the two portions. Note also that in some exemplary embodiments, the two portions overlap in the longitudinal direction.

In an exemplary embodiment, the extra-cochlear portion and the intra-cochlear portion of the malleable portion, combined, extend a first length from a housing containing a stimulator of the implantable stimulation device (e.g., the housing of the receiver stimulator), and the second malleable component and the malleable component that extends to the intra-cochlear portion have a combined second length which is less than or equal to about 99%, 98%, 97%, 96%, 95%, 90%, 85%, 80%, 75%, 70%, 66.66% (⅔rds), 65%, 60%, 55%, 50%, 45%, 40%, 35%, 33.333% ($\frac{1}{3}^{rd}$), 30%, 25%, 20%, 15%, or 10%, or any value or range of values therebetween in 0.1% increments, of the first length. In an exemplary embodiment, the portion of the malleable component that is a part of the intra-cochlear portion extends less than X % of a length of the intra-cochlear portion, and the portion of the malleable component that is part of the extra-cochlear portion extends less than Y % of the length of the extra-cochlear portion. In an exemplary embodiment, X and/or Y is 5%, 10%, 15%, 20%, 25%, 30%, 33.333% ($\frac{1}{3}^{rd}$), 35%, 40%, 45%, 50%, 55%, 60%, 65%, 66.667% (⅔rds), 70%, 75%, 80%, 85%, 90%, 95%, or 100% or any value or range of values therebetween in 0.1% increments.

It is noted that at least some of the embodiments detailed above have been disclosed in terms of the placement of the malleable portion at a location offset from the longitudinal axis of the elongate stimulating assembly, and/or have been disclosed in terms of placement of the malleable portion relative to the electrical leads of the lead assembly. In some exemplary embodiments, the embodiments that utilize the intracochlear malleable portion also utilize such features as disclosed above. Accordingly, in an exemplary embodiment, any of the teachings detailed above with respect to the extra cochlear malleable portion/structure that limit or otherwise prevent movement are also applicable to the embodiments directed to the intracochlear malleable portion/structure. That said, in some alternate embodiments the teachings relating to the placement of the malleable portion at a location offset from the longitudinal axis and/or placement of the malleable portion relative to the electrical leads are not applied to the embodiments that utilize the intracochlear malleable portion and/or structures that resist movement owing to the elastic properties of the elongate stimulating assembly. That is, in an exemplary embodiment, the intracochlear malleable portion is located at the longitudinal centerline of the elongate stimulating assembly. That is, in an exemplary embodiment, there is an elongate stimulation assembly of an implantable stimulation device, wherein a portion thereof includes a malleable component as detailed herein and/or variations thereof that extends from the intra-cochlear portion to a location in the extra cochlear portion, the extra-cochlear portion includes a plurality of electrical lead wires in electrical communication with the array of electrodes. There is also a malleable component extending in an elongate manner such that at least a portion of the malleable component is located closer to a longitudinal axis of the extra-cochlear portion than a portion of least one of the electrical leads of the plurality of electrical leads. Note also that this could be the case with respect to the malleable portion that is entirely located external to the intracochlear portion, at least when utilized with embodiments that include a separate malleable portion located in the intracochlear portion.

Also, in an exemplary embodiment, there is an elongate stimulation assembly of a cochlear implant, comprising an intra-cochlear portion including an array of electrodes, lead wires extending from the intra-cochlear region in electrical communication with the array of electrodes, the lead wires being located in an elongate lead body, and a malleable component extending in an elongate manner at least partially along with the lead wires, wherein the malleable component is located further from an outer surface of the lead body than at least one of the lead wires or wherein the malleable component is located the same distance from the outer surface of the lead body as at least one of the lead wires, wherein the malleable component has a portion extending into an intra-cochlear region. Also, in an exemplary embodiment, these aspects are also the case with respect to the second or third malleable component that does not have a portion in the intra-cochlear region but is used in conjunction with another malleable portion in the intra-cochlear region (e.g., 3410 when used with 2910 as seen in FIG. 34, etc.). In any event, any of the teachings detailed herein with respect to one embodiment can be combined with respect to another embodiment unless otherwise specified, providing that the art enables such combination.

Figure 35:
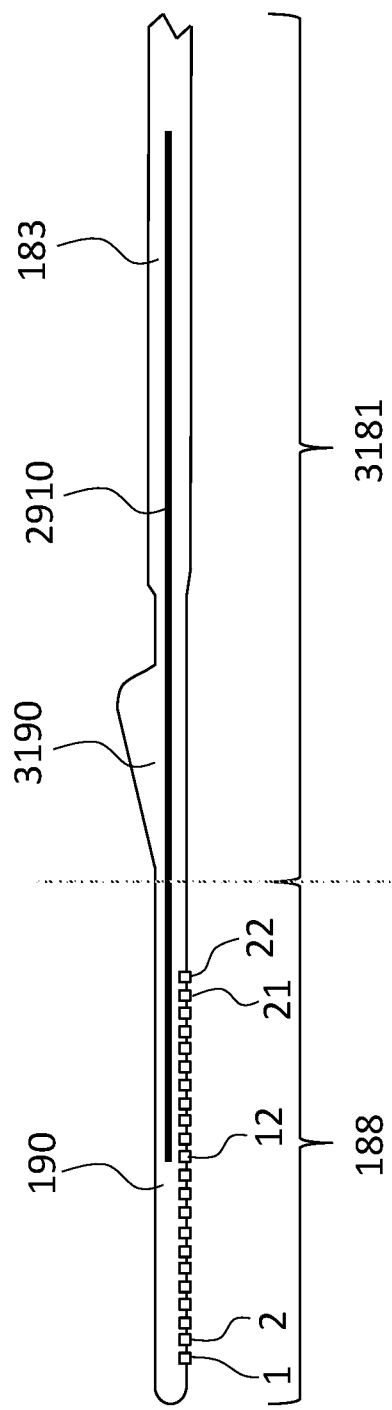

FIG. 35 depicts some additional details of the exemplary intracochlear malleable portion 2910. Specifically, FIG. 35 depicts a close-up view of the electrode array 190 and a distal portion of the lead assembly in general, and a distal portion of the body 183 of the lead assembly in particular. As can be seen, malleable portion 2910 extends only a portion of the length of the array of electrodes. In the embodiment of FIG. 35, there are 22 separate electrodes, and these electrodes are numbered from 1 to 22. It is noted that in at least some other embodiments, fewer electrodes or more electrodes will be utilized. In an exemplary embodiment, the electrode array has 2, 3, 4, 5, 6, 7, 8, 9, 10, 11, 12, 13, 14, 15, 16, 17, 18, 19, 20, 21, 22, 23, 24, 25, 26, 27, 28, 29, or 30, or more electrodes. In any event, the below teachings will be described in terms of the 22 electrode array.

Figure 36:
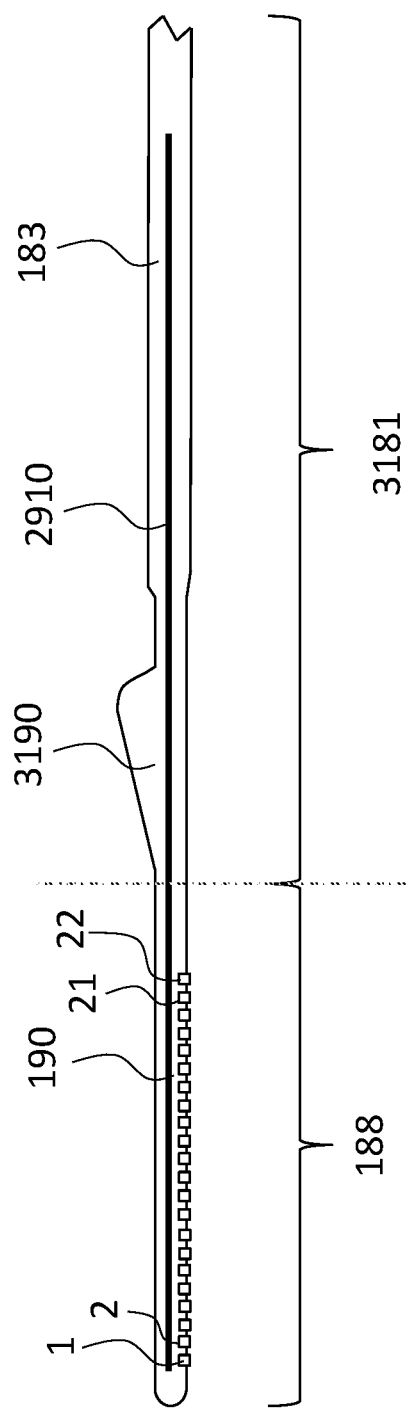

As can be seen, the malleable portion 2910 extends only past electrode numbers 12-22 of electrodes 1-22. Thus, in an exemplary embodiment, the malleable component of the electrode array extends past more than 50% of the electrodes of the electrode array. That said, in some embodiments, the malleable component of the electrode array extends past fewer than 50% of the electrode array, while extending past at least one electrode of the electrode array. Conversely, FIG. 36 depicts an exemplary embodiment where the malleable component 2910 extends past all of the electrodes of the electrode array (here, all 22 electrodes).

In an exemplary embodiment, the malleable component does not extend past more than 99%, 98%, 97%, 96%, 95%, 90%, 85%, 80%, 75%, 70%, 66.66% (⅔rds), 65%, 60%, 55%, 50%, 45%, 40%, 35%, 33.333% ($\frac{1}{3}^{rd}$), 30%, 25%, 20%, 15%, or 10% of the total number of electrodes of the electrode array, or any value or range of values therebetween in 0.1% increments. Accordingly, in an exemplary embodiment, the malleable component does not extend past with two thirds of the electrodes of the electrode array. In an exemplary embodiment, the malleable component extends past more than 99%, 98%, 97%, 96%, 95%, 90%, 85%, 80%, 75%, 70%, 66.66% (⅔rds), 65%, 60%, 55%, 50%, 45%, 40%, 35%, 33.333% (1/3$^{rd}$), 30%, 25%, 20%, 15%, or 10% of the total number of electrodes of the electrode array, or any value or range of values therebetween in 0.1% increments. Accordingly, in an exemplary embodiment, the malleable component extends past all of the electrodes or past 90% of the electrodes.

In an exemplary embodiment, the array of electrodes includes at least XX electrodes arrayed along a longitudinal direction of the intra-cochlear portion; and the malleable component extends from the extra-cochlear portion into the intra-cochlear portion such that the malleable component extends past at least YY of the electrodes of the electrode array. In an exemplary embodiment, XX is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more and YY is any of XX providing that it is not larger than a given XX, and zero. In an exemplary embodiment, XX can be 10 and YY can be 0, 1, 2, 3, 4, 5, 6, 7, 8, 9, or 10 (but not 11 or more, as that would exceed 10). In an exemplary embodiment, XX can be 22, and YY can be any number from and including 0 to and including 22.

It is noted that at least some exemplary embodiments include a single malleable component that extends at least substantially the entire length of the extra cochlear portion at substantially the entire length of the intracochlear portion. In an exemplary embodiment, the malleable component extends at least substantially the entire length of the extra cochlear portion and no more than about 80% of the intra-cochlear portion.

The figures detailed herein that include the electrodes are, in some embodiments, representative of electrode arrays where the distance from the tip of the electrode array to the most proximal electrode (e.g., electrode 22 in FIG. 38), is 5, 6, 7, 8, 9, 11, 12, 13, 14, 15, 16, 17, 18, 19, 20, 21, 22, 23, 24, 25, 26, 27, 28, 29, or 30 mm plus or minus 1 mm for any of the aforementioned dimensions, or any value or range of values therebetween in 0.1 mm increments (e.g., 20-25.3 mm, 8.1 to 10.5 mm, etc.).

It is noted that in some embodiments, element 2910 is not a malleable component, but instead a component that is not malleable. For example, element 2910 can be instead a Nitinol component or a component that is elastic, including super elastic. (Some additional details of this are described below.) Accordingly, in an exemplary embodiment, there is an elongate stimulation assembly of an implantable stimulation device, comprising an intra-cochlear portion including an array of electrodes, and an extra-cochlear portion extending from the intra-cochlear portion, wherein a first malleable component (e.g., element 3410) is located in the extra-cochlear portion, and a stiffener component (e.g., element 2910) is located in the intra-cochlear portion, the stiffener component being separate from the first malleable component. To be clear, in an exemplary embodiment, the stiffener can be a malleable component. Accordingly, in an exemplary embodiment, the stiffener component is a second malleable component separate from the first malleable component.

Concomitant with various embodiments described above, irrespective of the makeup of the stiffener component, the stiffener component has a first portion located in the intra-cochlear portion and a second portion located in the extra cochlear portion. In this regard, the relative dimensions detailed above with respect to the malleable portion that has component is located in the intracochlear portion the extra cochlear portion are also applicable to the stiffener of these embodiments.

Figure 37:
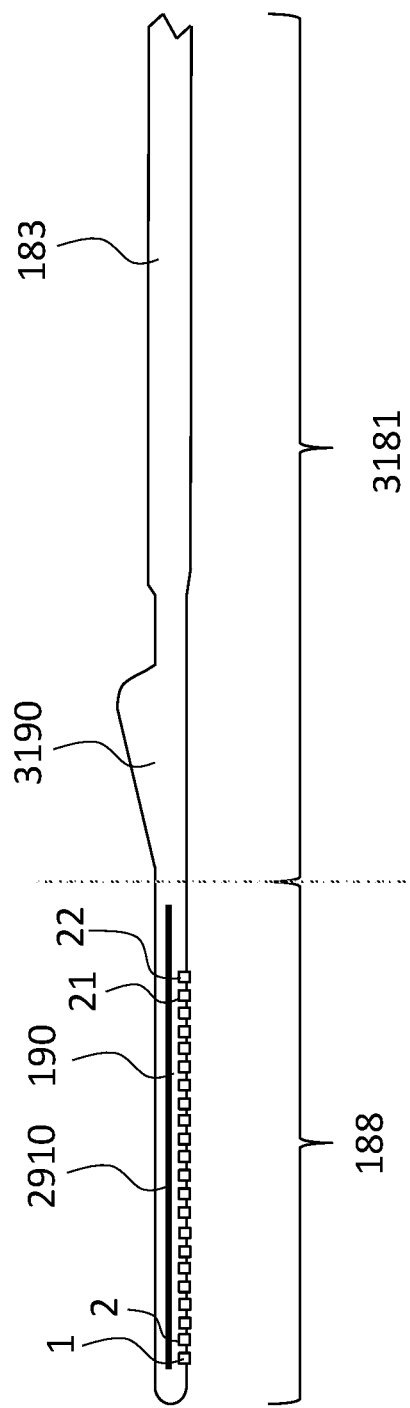

FIG. 37 depicts an alternate embodiment where the stiffener 2910 is located only in the intracochlear portion 188. That is, in an exemplary embodiment, the stiffener does not extend into the extra cochlear portion. Corollary to this is that in at least some exemplary embodiments, the first malleable component does not extend into the intracochlear portion.

Figure 38:
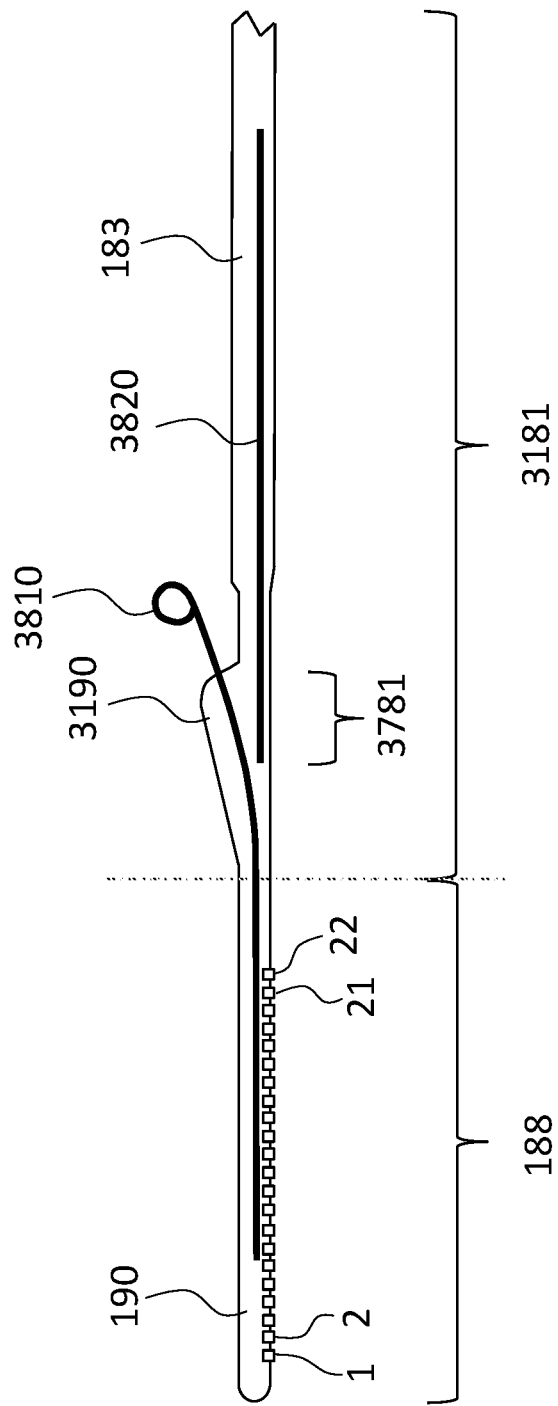

FIG. 38 depicts another exemplary embodiment where the stiffener 3810 is in the form of a removable stylet. Some additional details of the stylet 3810 will be described below. However, it is noted that stylets of the removable type enable a surgeon or other healthcare professional to retract or otherwise remove the stylet from the electrode array as the electrode array is being inserted into the cochlea so as to maintain a relatively stiffer portion at the local portion of the electrode array where the stylet is still present, while permitting the stylet to flex or otherwise bend by reducing the stiffness of the portion at the local portion of the electrode array from which the stylet has been removed.

In some exemplary embodiments, the stylet or any other removable stiffeners detailed herein and/or variations thereof can have a stopper to prevent overinsertion of the stylet into the elongate stimulating assembly. This stopper can be a moulded ring of silicone that extends about the stylet and/or can be a larger diameter handle from which the stylet protrudes, to facilitate handling. In an exemplary embodiment, the stopper can be a portion of the stylet that curves backwards towards the distal end of the stylet, so as to abut the interfacing surface of the elongate stimulating assembly.

It is noted that the removable stiffeners detailed herein can be a fixed single tool that is sterilizeable/resterilizeable, for multiple uses, or can be single use items.

In the embodiment of FIG. 38, the first malleable component is element 3820. Element 3820 is a totally extra cochlear component. As can be seen, the first stiffening component 3810 overlaps in the longitudinal direction of the elongate stimulation assembly with the first malleable component 3820. That said, in an alternate embodiment, there is no overlap in the longitudinal direction. Also, while the embodiment depicted in FIG. 38 is such that the first malleable component 3820 does not extend into the intra-cochlear portion 188, in an alternate embodiment, the first malleable component 3820 extends into the intracochlear portion 188. While the embodiments detailed herein with respect to element 3810 have been directed to a removable stylet, the teachings detailed herein with respect to element 3810 can also be applicable to a component that is not removable (e.g., element 2910 as applied in FIG. 37). Again, any feature of any embodiment disclosed herein can be combined with any other feature of any other embodiment disclosed herein unless otherwise noted. In this vein, while the embodiment of FIG. 38 has been described in terms of a single completely extra cochlear malleable component (element 3820), in an exemplary embodiment, two or more completely extra cochlear malleable components can be utilized with the stiffener. Accordingly, in an exemplary embodiment, there is an elongate stimulating assembly including a first and a second malleable component that are separate from one another, and are completely located in an extra cochlear portion of the elongate stimulating assembly, used in combination with a stiffener that includes at least a portion that is located in an intracochlear region of the elongate stimulating assembly, which stiffener is separate from the first malleable component and the second malleable component. In an exemplary embodiment, there can be a third malleable component that is completely located in an extra cochlear region. A fourth and/or a fifth and/or a sixth or more malleable components can be provided in the extra cochlear region. In at least some exemplary embodiments, one or more or all of the malleable components having portions located in the extra cochlear region or longitudinally spaced away from one or more or all of the other malleable components and/or the stiffener, while in other embodiments, one or more or all of the malleable components overlap one another in the longitudinal direction and/or one or more of the malleable components overlaps with the stiffener in the longitudinal direction.

Note also that in at least some exemplary embodiments, one or more of the stiffener components can extend into the intracochlear region from the extra cochlear region. In a similar vein, the stiffener component that has a portion in the intracochlear region can be completely located in the intracochlear region, while in other embodiments the stiffener can have a portion that is located in the intracochlear region while including another portion that is located in the extra cochlear region. Also, in an exemplary embodiment, one or more of the malleable components that are located in the extra cochlear region can be the only malleable component that is completely outside the intracochlear region of the elongate stimulating assembly. Corollary to this is that in at least some exemplary embodiments, the stiffener is the only malleable component that includes a portion that is located in the intracochlear region.

Figure 39:
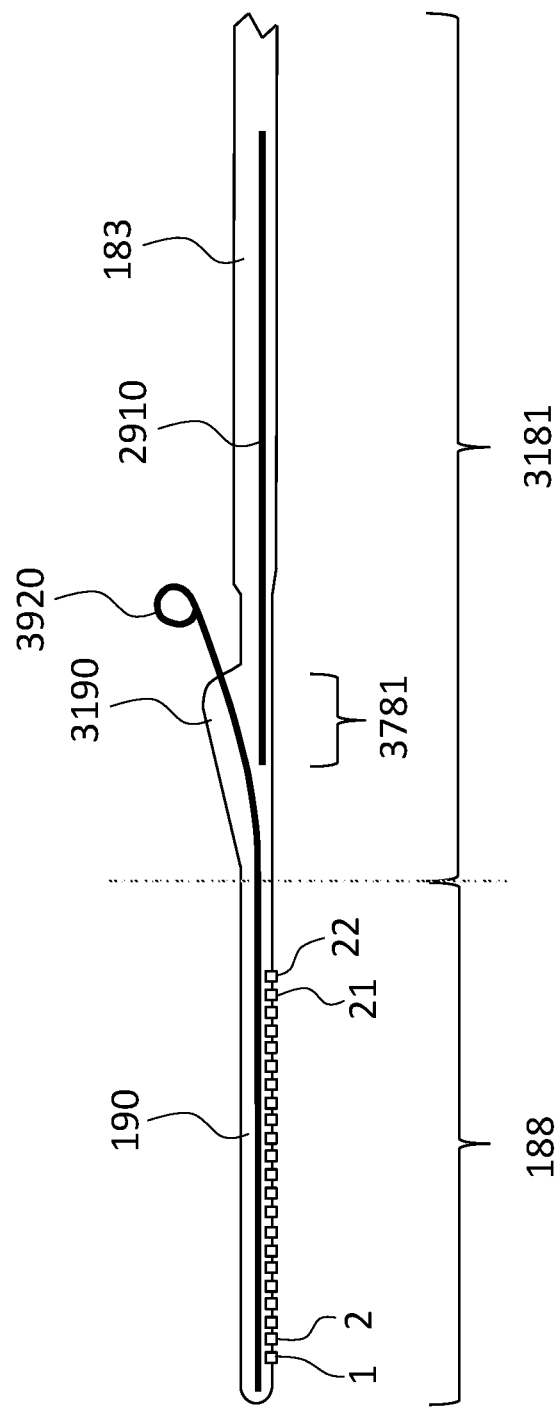

It is noted that the aforementioned lengths of extension of the malleable component that is located in the intracochlear region are also applicable to the embodiments that utilize a stiffener that is located in the intracochlear region, whether that stiffener is removable or not removable. Accordingly, FIGS. 38 and 39 depict some exemplary blanks of extension of the stylet, where stylet 3820 of the embodiment of FIG. 38 extends past all but the most distal six (6) electrodes, while stylet 3920 of the embodiment of FIG. 39 extends past all of the electrodes of the electrode array. Indeed, as can be seen, the stylet 3920, prior to removal, extends all the way to a location proximate the tip of the electrode array 190 (effectively extending to the tip—the embodiment of FIG. 39 maintains a portion made up of the material that is utilized to carry the electrodes (e.g., silicone) or other material that is located between the tip of the electrode array and the tip of the stylet, as there is utilitarian value with respect to not having the tip of the stylet extend beyond or be flush with the tip of the electrode array. In this regard, at least some exemplary embodiments have a portion located between the tip of the electrode array and the tip of a stylet such that the portion will prevent the electrode array from being pushed in the proximal direction relative to the stylet 3920. That is, the structural integrity of the distal portion of the electrode array 190 at least in the area between the tip of the stylet and the tip of the electrode array is such that longitudinal forces applied to the electrode array having a vector in the proximal direction likely to be experienced during insertion of the electrode array into the cochlea with the stylet 3920 fully inserted therein (due to friction on the outside diameter of the electrode array as the electrode array interfaces with the cochleostomy, due to the tip of the electrode array contacting bone or the like, etc., all while an insertion force applied to the electrode array (typically via a tool gripping the nub 3190) have a vector in the distal direction) will not drive the carrier portion of the electrode array 190 "downward" such that the stylet 3920 pierces or otherwise breaks the tip and extends through the tip. In an exemplary embodiment, a boot can be located in the electrode array that provides a barrier between the tip of the electrode array and the tip of a stylet to prevent such protrusion. The point is, by "the removable stiffener extending to a location proximate a tip of the intracochlear portion" of the electrode array, it is meant that there is a portion of the electrode array that is positioned between the tip of the stylet and the tip of the electrode array that is present for at least structural reasons.

Figure 40:
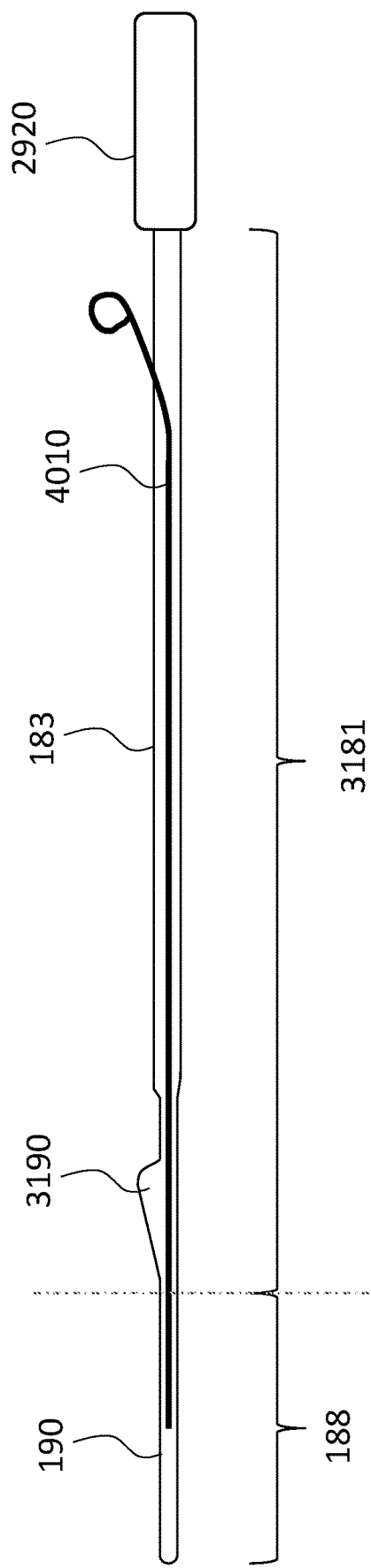

Also that the removable stiffener concept is not limited to simply utilization thereof in the intracochlear regions of the elongate stimulating assembly. The removable stiffener can be located in the extra cochlear portions as well, or, more accurately, a substantial portion of the elongate stiffener can be located in the extra cochlear portions. To this end, FIG. 40 depicts a stiffener 4010 that is removable that extends a substantial length of the lead assembly/extends a substantial length of the extra cochlear region 3181 of the elongate stimulating assembly. That said, in some alternate embodiments, the stiffener 4010 extends less than a substantial length of the lead assembly/extra cochlear region 3181. In an exemplary embodiment, any of the aforementioned extension lengths of the malleable components detailed above are applicable to the stiffener 4010 or any of the other stiffener detailed herein removable or the like. In an exemplary embodiment, the stiffener 4010 is malleable, while in other embodiments, the stiffener is elastic. In an exemplary embodiment, the stiffener 4010 can be removed, or more accurately, retracted, a distance such that the stiffener 4010 is not located in the intra-cochlear portion 188 of the electrode array, but still remains in the extra cochlear portion, such as by way of example only and not by way limitation, such that the tip is located approximately of the beginning of the lead assembly/distally of the end of the electrode array assembly. Thus, in an exemplary embodiment, the stiffener 4010 can be utilized as a stylet during insertion of the electrode array into the cochlea, which stylet is removed from the cochlea after insertion of the electrode array, but can also be utilized as a stiffening member for the lead assembly. In an exemplary embodiment, the surgeon could clip or otherwise separate the portion of the stiffener that extends out of the lead assembly at a location at or below the surface of the lead assembly so that the portion of the stiffener that has been retracted from the elongate stimulating assembly does not irritate or otherwise cause problems after implantation. In an exemplary embodiment, the surgeon or the like can put a piece of material or the like over the opening so as to ensure that the stiffener will not migrate further out of the assembly. Alternatively and/or in addition to this, this material can also be utilized to make sure that the stiffener does not migrate forward into the electrode array after implantation. In an exemplary embodiment, the electrode array assembly can be configured to be crimped or otherwise to be manipulated so as to prevent movement of the stiffener, or at least the portion of the stiffener that remains in the elongate stimulating assembly.

Figure 41:
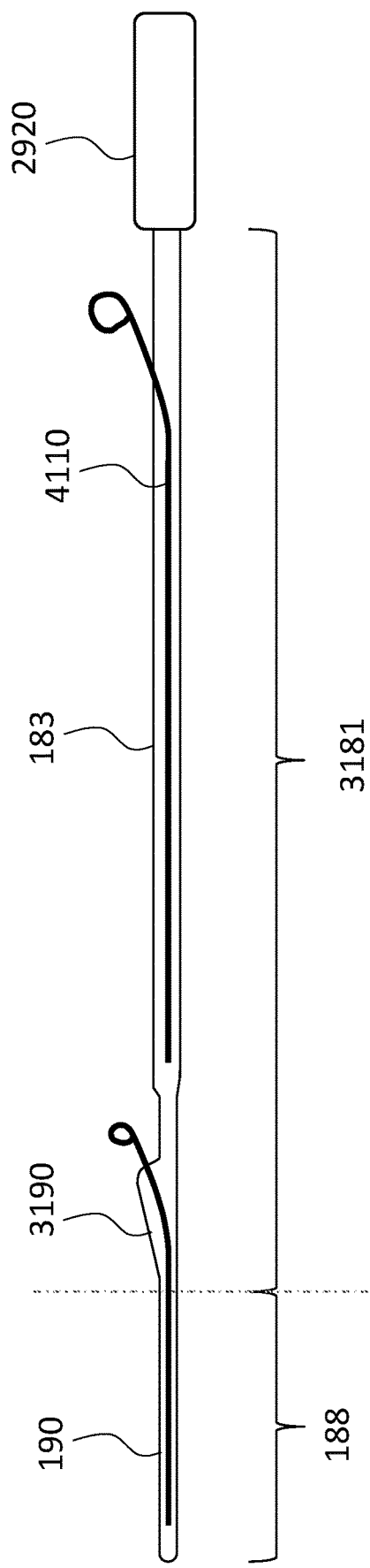

While the embodiment of FIG. 40 depicts the stiffener 4010 extending from the extra cochlear region 3180 into the intracochlear region, in an alternate embodiment, there are a plurality of removable stiffeners. FIG. 41 depicts such an exemplary embodiment, wherein the intracochlear stiffener is located in the electrode array, and a completely extra cochlear removable stiffener 4110 is located in the extra cochlear portion.

Figure 42:
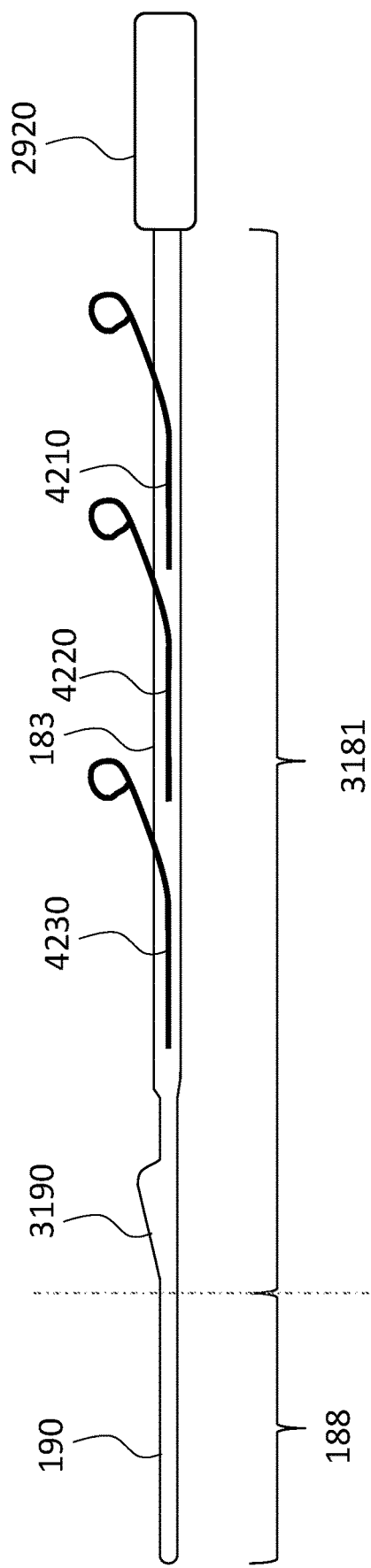

Note also that the removable features of the stiffener can have utilitarian value with respect to achieving control of the local relative stiffness of the electrode array. In this regard, a plurality of removable stiffeners can be located in the extra cochlear region. FIG. 42 conceptually depicts an exemplary embodiment that includes a first removable stiffener 4210, a second removable stiffener 4220, and a third removable stiffener 4230, each laterally spaced apart from one another along the lead assembly. In an exemplary embodiment, a surgeon or other healthcare professional can selectively remove one or more of these stiffeners so as to control or otherwise establish a local stiffness of the lead assembly. For example, an exemplary scenario can entail a surgical procedure where the surgeon finds that the elasticity of the lead assembly must be combatted at generally the midpoint of the extra cochlear portion 3181, but not at other portions away from the midportion. Thus, the surgeon can remove stiffener 4230 and stiffener 4210, while maintaining 4220 in place. Alternatively, the surgeon or other healthcare professional may find that stiffness has utilitarian value at locations everywhere save for the location closest to the receiver stimulator 2920. Thus, the surgeon or other healthcare professional will remove the stiffener 4210, while maintaining the others in place. It is noted that in at least some exemplary embodiments, the elongate stimulation assembly can be provided with features so as to maintain the removable stiffeners in place if the surgeon chooses not to remove such. This can provide for prevention of migration or the like of the removable stiffener from the elongate stimulation assembly after implanted into the recipient.

While the embodiment depicted in FIG. 42 depicts at least the portions of the stiffeners that are inside the lead assembly as being longitudinally spaced from one another, thus leaving a location where the lead assembly is not stiffened beyond that which results from the general structure thereof, in an alternate embodiment, the stiffeners can extend past one another, or be located such that ends thereof are located, with respect to the longitudinal direction, where the beginnings of others begin, at least until removed.

In some exemplary embodiments, the handle portions of the removable stiffeners can be removed by the surgeon after implantation and/or prior to implantation if the surgeon deems that the removable stiffener should not be removed (i.e., the removable stiffener should be in place after implantation of the implantable component).

In a similar vein to the embodiment of FIG. 42, in an exemplary embodiment, the elongate stimulation assembly can be configured with a plurality of openings along the length thereof (e.g., spaced every 10 mm, every 15 mm, spaced in an uneven manner, etc.) that leads to an inner channel of the lead assembly. In an exemplary embodiment, the surgeon or other healthcare professional determines where added stiffening has utilitarian value, and inserts the stiffener into the lead assembly at those locations such that the inserted stiffener extends into the channel and along the longitudinal length of the lead assembly a desired length. In this regard, in an exemplary embodiment, a kit can be provided with a plurality of different stiffeners having different lengths (duplicate stiffeners can also be provided), and the surgeon or other healthcare professional can insert the stiffener of a desired length at a desired location to achieve a local desired stiffness. This can be done a plurality of times. Indeed, configurations can be provided so that the stiffeners can overlap one another such that one local region of the lead assembly can be stiffer than another region of the lead assembly that also has the stiffeners. Note also that in an exemplary embodiment, the surgeon can shorten the stiffener to his or her liking. That is, one or more stiffeners of a long length (e.g., longer than the length of the elongate stimulating assembly) can be provided to the surgeon or other healthcare professional, and the surgeon or other healthcare professional can shorten the lengths of the stiffeners as is found to be utilitarian, and then insert the shortened stiffeners into the elongate stimulating assembly.

Corollary to the above is that in an alternate embodiment, one or more stiffeners can be provided in the array assembly, which stiffeners can be frangible or the like at certain locations upon the application of a pressure and/or upon the application of some other stimulus (e.g., ultraviolet radiation, etc.). The surgeon can break or otherwise weaken the stiffener at certain locations to reduce the stiffness of the elongate stimulation assembly at those locations where such has utilitarian value.

Accordingly, in an exemplary embodiment, there is an elongate stimulating assembly including an extra cochlear portion, wherein the extra cochlear portion is configured to have a stiffness that is adjustable at a local portion thereof. In an exemplary embodiment, the adjustability results from the ability to remove and/or insert a stiffening component as detailed above and/or as would otherwise be enabled by the art. In an exemplary embodiment, adjustability results from the configuration where the malleable component located in the extra cochlear region has a stiffness that is adjustable at a local portion thereof (e.g., due to the frangible nature of the malleable component, etc.).

It is noted that these exemplary embodiments can be used in conjunction with the intracochlear stiffener, whether such stiffener be a malleable component or not, and also as a separate feature without utilization in conjunction with such intracochlear stiffeners. Again, any feature detailed herein can be used separately without any other feature detailed herein unless otherwise specified. In this vein, an exemplary embodiment includes the utilization of a removable stiffener in the intracochlear region without a stiffener located in the lead portion of the elongate lead assembly. With reference to FIG. 38, and exemplary embodiment includes an electrode array 190 that includes a removable stiffener 3920, which electrode array is part of an elongate stimulating assembly, where there is no element 2910 or any other stiffener component/malleable component located in the extra cochlear portion of the elongate stimulating assembly. Not that there are not embodiments that utilize the removable stiffener in conjunction with the stiffener located in the extra cochlear portion, as noted above, it is just that this embodiment utilizes such without the stiffener components in the extra cochlear portion (at least other than the portion of the removable stiffener that extends from the intracochlear portion into the extra cochlear portion). In an exemplary embodiment, the electrode array is a so-called straight electrode array. That is, when the removable stiffener is removed, and in the absence of all other forces on the electrode array, the natural state of the electrode array is to be substantially straight. This as opposed to a so-called curved electrode array, where at least when any removable stiffener is removed, and in the absence of all other forces on the electrode array, the natural state of the electrode array is to be at least somewhat curved.

Figure 43:
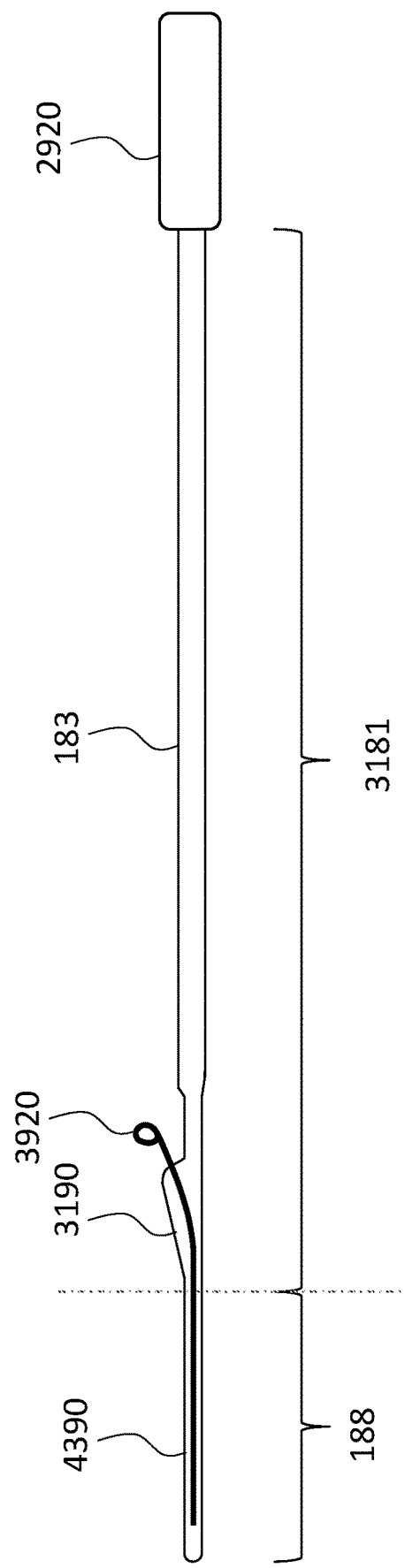

Accordingly, in an exemplary embodiment, there is a stimulation assembly of a cochlear implant, such as that depicted in FIG. 39 (where, in some embodiments, element 2910 is not present, or any other stiffener for that matter, such as seen in FIG. 43 by way of example, comprising, a straight electrode array 4390, including an intra-cochlear portion 188 including an array of electrodes (1-22, for example, but which can be more or less, according to the teachings detailed herein, and an extra-cochlear portion (the portion of the electrode array that is located in region 3181). In this exemplary embodiment, there is a removable stiffener (e.g., 3920, located in the straight electrode array, the removable stiffener 3920 extending from the extra cochlear portion to a location proximate a tip of the intra-cochlear portion (concomitant with the embodiment of FIG. 39 in this regard). Here, the removable stiffener is a removable stylet, concomitant with such stylets known in the art. Still, in some embodiments, the removable stiffener is an elastic component, such as a component made from Nitinol. In an exemplary embodiment, the stiffener has super elastic features, as noted above.

In an exemplary embodiment, the straight electrode array has no stiffener therein other than the removable stiffener.

It is noted that some features of the straight electrode array can have utilitarian value with respect to preserving so-called residual hearing. In this regard, in an exemplary embodiment, the embedded and/or removable stiffeners detailed herein that are located in the intracochlear region can be provided so as to obtain a so-called lateral wall placement of the electrode array and/or a so-called mid scala placement of the electrode array. In an exemplary embodiment, the stiffener can be sufficiently malleable so as to malleably deform as the electrode array is inserted into the cochlea due to forces applied by the lateral wall onto the electrode array as the electrode array extends further into the cochlea (owing to the curvature of the cochlear).

In the embodiments where the stiffener is a removable stylet, the stiffener can have any of the configurations detailed above with respect to the structure that is utilized to control or otherwise reduce or eliminate movement of the lead assembly due to the elasticity of that structure. In this regard, the teachings detailed above with respect to reducing movement or otherwise controlling movement of the lead assembly due to the elasticity of the lead assembly are also applicable to reducing movement or otherwise controlling movement of the electrode array due to the elasticity of the electrode array. In this regard, in an exemplary embodiment, the stiffener located in the electrode array, movable or otherwise, is configured to provide less stiffness than that which would correspond to traditional stylets, at least those approved for use by the FDA and/or the European Medicines Agency and/or the comparable agencies in the United Kingdom, Republic of France, the Federal Republic of Germany, Japan, the Republic of Korea, and/or the People's Republic of China. In an exemplary embodiment, the stiffness of the stiffener is no more than 90%, 85%, 80%, 75%, 70%, 65%, 60%, 55%, 50%, 45%, 40%, 35%, or 30% of that which is present with respect to aforementioned approved stylets, all other things being equal, at, for example, a mid-point of the stiffener, at a location $\frac{1}{4}^{th}$ or $\frac{1}{3}^{rd}$ of the length (from either or both ends), on average, at 2, or 3, or 4, or 5, or more evenly spaced locations along the stiffener. That said, in some embodiments, the stiffener located in the intracochlear portion is designed to increase the elasticity of the electrode array relative to that which would be the case in the absence of the stiffener and/or relative to that which would be the case with conventional stylets. In an exemplary embodiment, the elasticity of the stiffener is more than 50%, 75%, 100%, 125%, 150%, 200%, 250%, 300%, 350%, 400%, 450%, 500%, 600%, 700%, 800%, 900%, or more than that which is present with respect to aforementioned approved stylets, all other things being equal, at, for example, a mid-point of the stiffener, at a location $\frac{1}{4}^{th}$ or $\frac{1}{3}^{rd}$ of the length (from either or both ends), on average, at 2, or 3, or 4, or 5, or more evenly spaced locations along the stiffener.

In an exemplary embodiment, the stiffeners utilized in the embodiments detailed herein are made of annealed platinum, having a diameter of 100 to 250 micrometers over at least 50% of the length thereof, and at least over 60%, 65%, 70%, 75%, 80%, or 85%, or more or all of the length thereof. Palladium and/or gold can be utilized alternatively and/or instead of platinum. In some alternate embodiments, the stiffeners utilized in the embodiments detailed herein are substantially devoid, including completely devoid, of platinum, palladium and/or gold. In an exemplary embodiment, the stiffeners consist essentially of platinum, palladium and/or gold, while in other exemplary embodiments, the stiffeners consist essentially of materials other than platinum, palladium and/or gold.

It is noted that in some embodiments, the removable stiffeners can have rounded or bulbus tips to facilitate insertion into the lumen into which the stiffeners are placed so as to avoid damage to the body of the electrode array (e.g., the silicone forming the lumen in which the removable stiffener is located). This can also be the case with the stiffeners that are not removable as well.

It is noted that in at least some exemplary embodiments, the removable stiffeners can include locking components or securing components of the secure the removable stiffeners in place along a longitudinal position thereof. For example, the removable stiffeners can be configured such that graduated insertion depth can be predetermined and the removable stiffeners will be secured in place at those graduated insertion depths. It is also noted that other portions of the elongate stimulating assembly can include such locking features.

Figure 44:
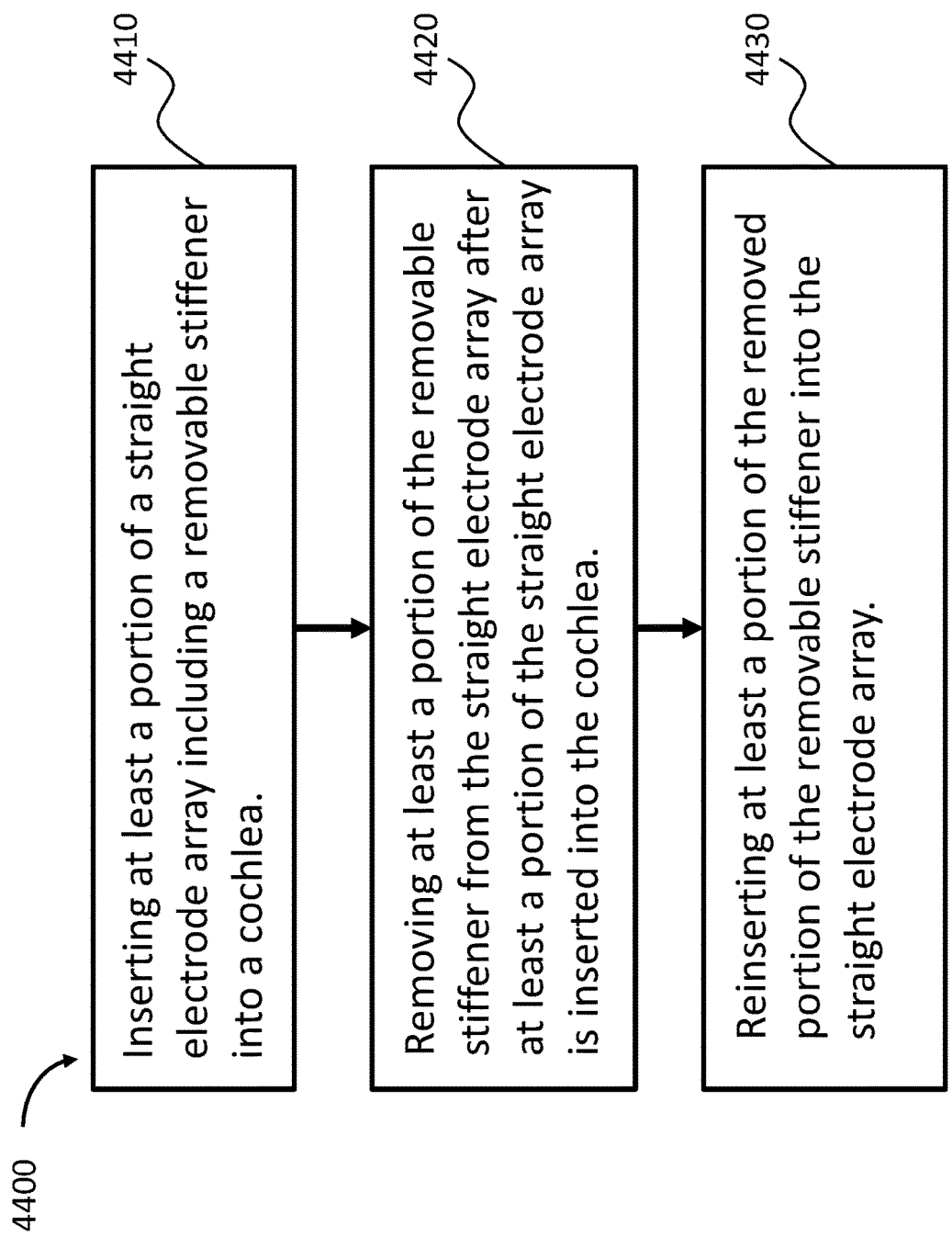
FIG. 44 depicts an exemplary flow chart according to an exemplary method.

FIG. 44 presents an exemplary flowchart for an exemplary method, method 4400, according to an exemplary embodiment. Method 4400 includes method action 4410, which includes inserting at least a portion of a straight electrode array including a removable stiffener, such as any of the electrode array's detailed herein and/or variations thereof in the form of a straight electrode array, into a cochlea of a recipient. In this embodiment, the straight electrode array is at least partially located in the electrode array such that a portion of the stiffener is also inserted into the cochlea (albeit such that the body of the electrode array is interposed between the stiffener and the environment inside the cochlea). Method 4400 further includes method action 4420, which includes removing at least a portion of the removable stiffener from the straight electrode array after at least a portion of the straight electrode array, which portion includes at least a portion of the stiffener, is inserted into the cochlea. That is, the portion that is removed is a portion that was already in the cochlea (again, albeit such that the body of the electrode array is interposed between the removable stiffener in the environment of the cochlea). In an exemplary embodiment, the removable stiffener is completely removed from the straight electrode array, while in other embodiments, only a portion of the removable stiffener is removed. In any event, method 4400 further includes method action 4430, which includes reinserting at least a portion of the removed portion of the removable stiffener into the straight electrode array. In the case where method action 4420 corresponds to complete removal of the removable stiffener, method action 4430 corresponds to inserting at least a portion of the removable stiffener back into the electrode array. This can also include reinserting the entire stiffener.

In an exemplary embodiment of the aforementioned methods, the stiffener bends during one of the aforementioned method actions. Indeed, in an exemplary embodiment, where the stiffener is an elastic component, the stiffener is maintained in the electrode array without retraction while at least 30%, 35%, 40%, 45%, 50%, 55%, 60%, 65%, 70%, 75%, 80%, 85%, 90%, 95%, or all of the longitudinal length of the intracochlear portion of the electrode array is inserted in the cochlea. In an exemplary embodiment, again where, for example, the stiffener is an elastic component, no more than 20%, 25%, 30%, 35%, 40%, 45%, 50%, 55%, 60%, 65%, 70%, 75%, 80%, 85%, or 90% by longitudinal length of the portion of the stiffener that is located in the electrode array and/or the portion of the stiffener that is inserted into the cochlea with the electrode array is removed at the point where one or more of the aforementioned percentages of the electrode array is inserted into the cochlea.

Note also that precedent method action 4430, in an exemplary method, the method action of removing at least some or all of the straight electrode that was inserted into the cochlea is executed. That is, in an exemplary embodiment, or more specifically, in an exemplary scenario of insertion of the electrode array into the cochlea, a surgeon can execute method action 4420, and then determine that the insertion regime is not proceeding according to that as desired or otherwise according to that which has more utilitarian value than that which is occurring. The surgeon can determine that he or she should remove part and/or all of the electrode array from the cochlea, which electrode array was previously inserted during this procedure. So as to achieve the stiffening characteristics corresponding to that which existed at the time that the portion of the electrode array that was removed from the cochlea, the surgeon or other healthcare professional reinserting at least a portion of the removable stiffener. This can be done while the removed portion of the electrode array is removed from the cochlea and/or while the removed portion is being removed from the cochlea.

While the focus of method 4400 has been directed towards a straight electrode array, in some alternate embodiments, method 4400 can be executed utilizing a curved electrode array.

An exemplary embodiment includes utilizing the removable stiffeners so as to vary in insertion depth of in a given electrode array over a relatively long period of time. For example, in an exemplary embodiment, at a first temporal period, the electrode array is inserted only a shallow insertion depth, such as 10 to 12 to 14 to 16 to 18 mm into the cochlea. In this regard, in this exemplary embodiment, the recipient has residual hearing at the lower and mid frequencies. Thus, the electrode array is inserted in the cochlea to stimulate the portions of the cochlea that are receptive to higher frequency sounds. In this exemplary embodiment, a removable stiffener is utilized during this insertion process, and subsequently completely removed from the electrode array. Alternatively, a removable stiffener is utilized, but the stiffener is retained in the electrode array, so as to provide stiffness in the portions of the electrode array located in the basal region. In any event, after some period of time, where the residual hearing of the recipient decreases, which could be one year, two years, three years, four years, five years or more after the initial insertion, and it is thus utilitarian to revise the electrode array positions to achieve a deeper insertion depth, a new removable stiffener is inserted into the electrode array while the electrode array is still inside the cochlea. This new removable stiffener can be partially or fully inserted into the electrode array. The surgeon or other healthcare professional then subsequently inserts the electrode array further into the cochlea, utilizing the new removable stiffener to provide stiffness to the electrode array in a conventional manner. In an exemplary embodiment, the surgeon or other healthcare professional subsequently inserts the electrode array into the cochlea a distance of 22 to 24 to 26 mm or more so as to achieve a full insertion depth thereof. Subsequent to full insertion, or during the full insertion process, the stylet can be removed leaving the un stiffened electrode array in the cochlea, just as was the case with the partially inserted electrode array during the first temporal period. Alternatively, in the in an exemplary embodiment, the removable stiffener is maintained in the electrode array after the partial insertion, and thus is implanted into the recipient, which removable stiffener can be locked in place according to the teachings detailed above and/or variations thereof. Subsequently, after the residual hearing is lost, and the electrode array is to be inserted further into the cochlea, the implanted removable stiffener can be utilized in the traditional manner during the full advancement of the electrode array, and then removed according to the traditional manner.

In at least some exemplary embodiments, the method of inserting the electrode array into the cochlea is such that the removable stiffener is removed from the electrode array as the electrode array is inserted into the cochlea, or, more accurately, the removable stiffener is removed from the electrode array as the portion of the electrode array reaches the basal turn of the cochlea so as to avoid contact with the wall of the cochlea and the portion of the electrode array that is stiffened by the removable stiffener. By way of example only and not by way of limitation, the electrode array can be inserted into the cochlea with the removable stiffener fully advanced into the electrode array, without moving the stiffener relative to the electrode array. However, as the electrode array reaches the first turn of the cochlea, or, more accurately, as the portion of the electrode array that is stiffened by the removable stiffener reaches the first turn the cochlea, the surgeon or other health care professional prevents the removable stiffener from advancing further into the cochlea. In an exemplary embodiment, the surgeon or other healthcare professional holds the stiffener in a static position relative to the anatomy of the recipient while the surgeon or other healthcare professional continues to advance the electrode array into the cochlea.

It is noted that in some exemplary embodiments, a portion of the electrode array that is stiffened by the removable stiffener can contact the lateral wall of the cochlea. In an exemplary embodiment, this can occur prior to reaching the first basal turn. In this regard, in at least some exemplary embodiments, there is no direct reactive force that reacts in the opposite direction of electrode advancement, contrary to that which exists when the electrode array reaches the first basal turn. In at least some exemplary embodiments, it is the contact of the lateral wall of the cochlea with a portion of the electrode array that is stiffened by the removable stiffener at and beyond the first basal turn that is avoided according to some exemplary method insertions, while contact of the lateral wall of the cochlea with a portion of the electrode array that is stiffened by the removable stiffener prior to the first basal turn is not avoided.

Figure 45:
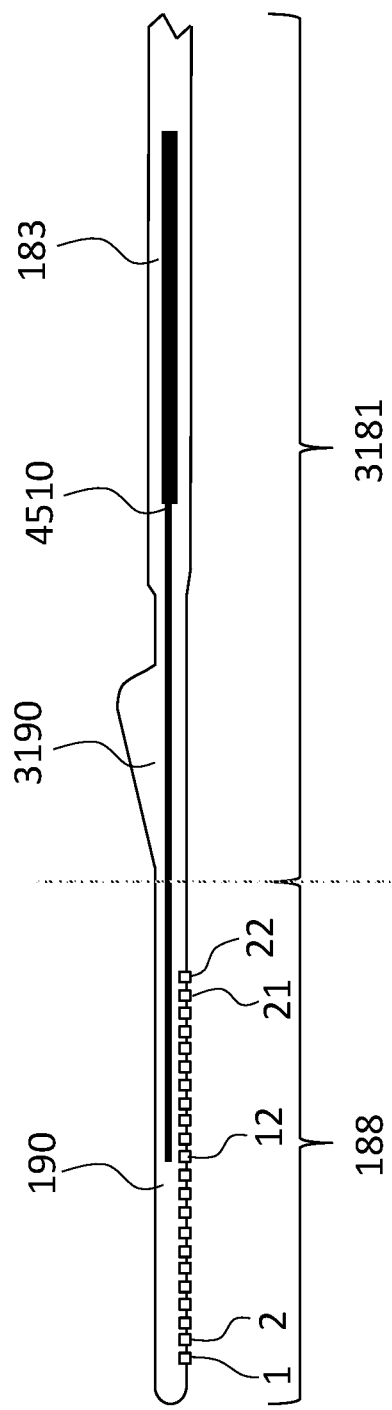
FIG. 45 depicts a schematic according to another exemplary embodiment.

Briefly, it is noted that in at least some exemplary embodiments, a stiffness of the portion of the malleable component/stiffener that is part of the intra-cochlear portion is different than a stiffness of the portion of the malleable component that is part of the extra-cochlear portion. In some exemplary embodiments, this can be achieved by varying a diameter of the stiffener/malleable component. An exemplary embodiment of this is depicted in FIG. 45, where stiffener 4510 has a first diameter within the intracochlear portion of the smaller than that of a second diameter of the stiffener 4510 in the extra cochlear portion. Thus, in this exemplary embodiment, the portion of the stiffener/malleable component that is in the intracochlear portion is stiffer than the portion that is in the extra cochlear portion (all other things being equal). That said, in some alternative embodiments, this arrangement can be reversed, where the first diameter of the stiffener within the intracochlear portion is larger than that of the second diameter in the extra cochlear portion, and thus the portion that is in the extra cochlear portion of the stiffener portion in the intracochlear portion (all other things being equal). Note also that this concept can be applied to other locations along the extra cochlear portions of the various malleable component detailed herein and/or variations thereof.

In some alternate embodiments, a material stiffness of a portion of the stiffener/malleable component that is part of the intracochlear portion is different than a material stiffness of the portion of the stiffener/malleable component that is part of the extra-cochlear portion, wherein the stiffener/malleable component is a monolithic component. By "material stiffness," it is meant that the stiffness of the material as a material property, as opposed to the stiffness that results from the structural geometry. That is, irrespective of the relative dimensions of the stiffener, when a per unit basis, the stiffness of the material is different. By way of example only and not by way of limitation, this can be achieved by tempering or heat-treating the two portions of the stiffener differently, such that one portion has a higher stiffness than the other portion. In an exemplary embodiment, one portion can be fully annealed (e.g. the portion in the intracochlear region or at least a portion thereof) in one portion can be partially annealed (e.g. the portion outside the intracochlear region, or at least a portion thereof). In an exemplary embodiment, the material stiffness of the portion that is located in the intracochlear region is greater than that which is the case in the extra cochlear portion while in other embodiments this is reversed. In an exemplary embodiment, the aforementioned material stiffnesses are different, where the stiffener is a monolithic component and the diameter of the stiffener is uniform between the two portions (the portion located in the intracochlear portion of the portion located in the extra cochlear portion).

Any device, system, and/or method that can enable the stiffener to have different stiffness is along the longitudinal length thereof can utilize in at least some exemplary embodiments.

In an exemplary embodiment, there is an elongate stimulation assembly of an implantable stimulation device, comprising an intra-cochlear portion including an array of electrodes; and an extra-cochlear portion extending from the intra-cochlear portion, wherein the extra-cochlear portion includes a malleable component extending in an elongate manner, a beginning of the malleable component extending from a location proximate the intra-cochlear portion (e.g., the beginning of the component being located at the beginning of the lead assembly (the distal beginning), or close thereto, and/or less than 1, 2, 3, 4, 5, 6, 7, 8, 9, 10, 11, 12, 13, 14, 15, 16, 17, 18, 19, 20 mm distally or proximally the distal beginning of the lead assembly or a distance from the end of the intracochlear portion) to a location in the extra-cochlear portion that is less than about XXX the length of the elongate stimulation assembly. In an exemplary embodiment, XXX 90%, 85%, 80%, 75% (three-quarters), 70%, 66.66% (⅔rds), 65%, 60%, 55%, 50%, 45%, 40%, 35%, 33.333% (⅓$^{rd}$), 30%, 25%, 20%, 15%, or 10%.

It is noted that in an exemplary embodiment, the stylet/removable stiffener of the intra-cochlear portion, or any other stiffener removable or otherwise, can be tapered, or have generally varying cross-section, to have a varied bending stiffness along its length.

It is noted that while in some embodiments, the structures detailed herein are depicted as having a cross-section that is circular, other embodiments can utilize structures having cross-sections of different shapes, such as by way of example only and not by way of limitation, square shapes, diamond shapes, hexagonal shapes, etc., of cross-sections can be utilized. Further, while the structures detailed herein are depicted as having symmetrical cross-sections, in some alternative embodiments, the cross-sections are non-symmetric. By way of example only and not by way limitation, non-even rectangular shapes, oval shapes, pentagonal shapes and/or triangular cross-sections can be utilized. Any structure that can enable the teachings detailed herein and/or variations thereof to be practiced can be utilized in at least some exemplary embodiments.

It is noted that with respect to the helical structures detailed above, in at least some exemplary embodiments, the helical structures are wires formed into a helical shape.

It is noted that in at least some exemplary embodiments, the malleable structures detailed herein can be utilized to conduct electricity or otherwise conduct stimulation signals in a manner analogous to and/or the same as that which occurs with respect to the lead wires. In an exemplary embodiment, the malleable component establishes electrical communication with at least one electrode of the array of electrodes.

It is noted that in at least some exemplary embodiments, the teachings detailed herein can have utilitarian value with respect to reducing and/or eliminating a torque that is applied to the electrode array due to the lead assembly. Accordingly, an exemplary embodiment entails an implanted stimulating assembly that is relatively torque free with respect to the electrode array assembly while the electrode array assembly is located in the cochlea. Still further by way of example, in an exemplary embodiment, the teachings detailed herein can have utilitarian value with respect to reducing and/or eliminating electrode migration out of the cochlea and/or within the cochlea (e.g., twisting of the electrode array within the cochlea, movement of the electrode array out of the cochlea, at least in part, etc.). In at least some exemplary embodiments, the aforementioned teachings can result in fatigue failure relief/a reduction in failure due to fatigue of one or more portions of the stimulating assembly.

It is further noted that in at least some exemplary embodiments, the teachings detailed herein can have utilitarian value with respect to managing the growth of bone tissue with respect to children as they grow. That is, in an exemplary embodiment, because of the additional portion of the stimulating assembly located within a cavity formed by the mastoid cavity in the middle ear (the "slack"), growth of the mastoid bone which moves the receiver/stimulator away from the cochlea will not impart a stress on to the stimulating assembly that would pull the stimulating assembly out of the cochlea or otherwise impart a torque and/or a force onto the electrode array located in the cochlea.

As noted above, some and/or all of the teachings detailed herein can be used with a hearing prosthesis, such as a cochlear implant. That said, while the embodiments detailed herein have been directed towards cochlear implants, other embodiments can be directed towards application in other types of hearing prostheses, such as by way of example, other types of electrode arrays used in medical devices (e.g., pacemakers, nerve stimulators, etc.). Indeed, embodiments can be utilized with any type of medical device that utilizes an implanted electrode array, or even a non-implanted array, at least if there is utilitarian value with respect to conducting a test for an open circuit while the electrode array is located within packaging.

It is noted that any disclosure with respect to one or more embodiments detailed herein can be practiced in combination with any other disclosure with respect to one or more other embodiments detailed herein.

In an exemplary embodiment, there is an elongate stimulation assembly of an implantable stimulation device, comprising an intra-cochlear portion including an array of electrodes; and an extra-cochlear portion extending from the intra-cochlear portion, wherein the extra-cochlear portion includes a plurality of electrical lead wires in electrical communication with the array of electrodes and a malleable component extending in an elongate manner such that at least a portion of the malleable component is located further away from or the same distance from a longitudinal axis of the extra-cochlear portion than a portion of least one of the electrical leads of the plurality of electrical leads.

In an exemplary embodiment as described above and/or below, there is an elongate stimulation assembly as described above and/or below, wherein the malleable component is a metallic element. In an exemplary embodiment as described above and/or below, there is an elongate stimulation assembly as described above and/or below, wherein the extra-cochlear portion includes a lead body; and the malleable component is a metal wire embedded in the lead body. In an exemplary embodiment as described above and/or below, there is an elongate stimulation assembly as described above and/or below, wherein: the extra-cochlear portion includes a lead body; and the malleable component is a metal wire located completely outside the lead body. In an exemplary embodiment as described above and/or below, there is an elongate stimulation assembly as described above and/or below, wherein: the extra-cochlear portion includes a lead body in which are located the plurality of lead wires; and the malleable component establishes electrical communication with at least one electrode of the array of electrodes. In an exemplary embodiment as described above and/or below, there is an elongate stimulation assembly as described above and/or below, wherein: the malleable component is a helical structure wrapped around at least some of the lead wires. In an exemplary embodiment as described above and/or below, there is an elongate stimulation assembly as described above and/or below, wherein: the extra-cochlear portion includes a lead body; the lead wires are encapsulated in the lead body; and the malleable component is a helical structure extending about the lead body at least partially external to the lead body. In an exemplary embodiment as described above and/or below, there is an elongate stimulation assembly as described above and/or below, wherein: the malleable component is a helical structure wrapped around all of the lead wires.

In an exemplary embodiment, there is an elongate stimulation assembly of a cochlear implant, comprising: an intra-cochlear portion including an array of electrodes; lead wires extending from the intra-cochlear region in electrical communication with the array of electrodes, the lead wires being located in an elongate lead body; and a malleable component extending in an elongate manner at least partially along with the lead wires, wherein the malleable component is located closer to an outer surface of the lead body than at least one of the lead wires or wherein the malleable component is located the same distance from the outer surface of the lead body as at least one of the lead wires. In an exemplary embodiment, there is an elongate stimulation assembly of a cochlear implant as described above and/or below, wherein: the malleable component is a helical structure. In an exemplary embodiment, there is an elongate stimulation assembly of a cochlear implant as described above and/or below, wherein: the lead wires are encapsulated in the lead body; and the malleable component is a helical structure extending about the lead body attached to a surface of the lead body. In an exemplary embodiment, there is an elongate stimulation assembly of a cochlear implant as described above and/or below, wherein: the lead wires are encapsulated in the lead body; and the malleable component is a helical structure extending about the lead body such that the lead body can move locally relative to the helical structure. In an exemplary embodiment, there is an elongate stimulation assembly of a cochlear implant as described above and/or below, wherein: the lead wires are encapsulated in a lead body; and the malleable component is a helical structure extending about the lead body such that the lead body can move locally relative to the helical structure while preventing global movement of the lead body. In an exemplary embodiment, there is an elongate stimulation assembly of a cochlear implant as described above and/or below, wherein: the lead wires are encapsulated in a lead body; and the malleable component is attached to an outer surface of the lead body. In an exemplary embodiment, there is an elongate stimulation assembly of a cochlear implant as described above and/or below, wherein: the malleable component forms one helix of a double helix, and the lead wires form the other helix of the double helix.

In an exemplary embodiment, there is a method, comprising: obtaining access to a subcutaneous region of a recipient's head; implanting a stimulating assembly at the subcutaneous region, wherein the action of implanting the electrode assembly includes plastically deforming a first portion of the stimulating assembly so as to maintain the first portion now deformed at a first orientation due to the deformation of the first portion. In an exemplary embodiment, there is a method as described above and/or below, further comprising: inserting at least a portion of an electrode array into a cochlea, wherein the action of deforming the first portion of the stimulating assembly is executed before insertion of the at least a portion of the electrode array into the cochlea. In an exemplary embodiment, there is a method as described above and/or below, wherein: the action of implanting the stimulating assembly includes plastically deforming a second portion of the stimulating assembly so as to maintain the second portion now deformed at a second orientation due to the deformation of the second portion. In an exemplary embodiment, there is a method as described above and/or below, further comprising: inserting at least a portion of an electrode array into a cochlea, wherein the action of deforming the first portion of the stimulating assembly is executed before insertion of the at least a portion of the electrode array into the cochlea, and the action of deforming the second portion of the stimulating assembly is executed after insertion of the at least a portion of the electrode array into the cochlea. In an exemplary embodiment, there is a method as described above and/or below, wherein: the accessed subcutaneous region includes an artificial channel in a mastoid bone of the recipient leading to a mastoid cavity, wherein the mastoid cavity is part of a cavity that is bounded in part by a round and oval window of a cochlea of the recipient; the action of implanting the electrode assembly includes placing the first portion of the stimulating assembly into the artificial channel such that a first sub-portion is located in the channel and a second sub-portion extends from the channel into the mastoid cavity; and the action of deforming the first portion entails bending the first portion such that the second sub-portion is moved from a first orientation relative to the first sub-portion to a second orientation relative to the first sub-portion, and the plastic deformation maintains the second sub-portion at the second orientation.

In an exemplary embodiment, there is a method as described above and/or below, wherein: the second orientation is such that a longitudinal axis of the second sub-portion is at least about 45 degrees from a longitudinal axis of the first sub-portion. In an exemplary embodiment, there is a method as described above and/or below, wherein: the subcutaneous region includes a mastoid cavity; and the method is executed without placing any portion of the stimulating assembly against any bone overhanging the mastoid cavity. Wherein the action of implanting the electrode assembly further includes: inserting an intracochlear electrode into a cochlea through an opening therein; and securing a portion of the electrode assembly located between the intracochlear electrode and a receiver/stimulator connected to the stimulating assembly in a mastoid cavity without contacting a bony overhang of the mastoid cavity.

In an exemplary embodiment, there is an elongate stimulation assembly of an implantable stimulation device, comprising: an intra-cochlear portion including an array of electrodes; and an extra-cochlear portion extending from the intra-cochlear portion, wherein a malleable component extending from the extra-cochlear portion to the intra-cochlear portion such that the extra-cochlear portion and the intra-cochlear portion also include respective portions of the malleable component. In an exemplary embodiment, there is an elongate stimulation assembly of an implantable stimulation device as described above and/or below, wherein: the array of electrodes includes at least 10 electrodes arrayed along a longitudinal direction of the intra-cochlear portion; and the malleable component extends from the extra-cochlear portion into the intra-cochlear portion such that the malleable component extends past at least 5 of the electrodes of the electrode array. In an exemplary embodiment, there is an elongate stimulation assembly of an implantable stimulation device as described above and/or below, wherein: the malleable component does not extend past more than ⅔rds of the electrodes of the array of electrodes. In an exemplary embodiment, there is an elongate stimulation assembly of an implantable stimulation device as described above and/or below, wherein: the malleable component extends at least one of past all of the electrodes or past 90% of the electrodes. In an exemplary embodiment, there is an elongate stimulation assembly of an implantable stimulation device as described above and/or below, wherein: the malleable component extends from the intra-cochlear portion to a location at least proximate a housing containing a stimulator of the implantable stimulating device, or the malleable component extends from the intra-cochlear portion to the housing. In an exemplary embodiment, there is an elongate stimulation assembly of an implantable stimulation device as described above and/or below, wherein: the malleable component extends at least substantially the entire length of the extra-cochlear portion and substantially the entire length of the intra-cochlear portion. In an exemplary embodiment, there is an elongate stimulation assembly of an implantable stimulation device as described above and/or below, wherein: the malleable component extends at least substantially the entire length of the extra-cochlear portion and no more than about 80% of the intra-cochlear portion. In an exemplary embodiment, there is an elongate stimulation assembly of an implantable stimulation device as described above and/or below, wherein: the malleable component is a monolithic component. In an exemplary embodiment, there is an elongate stimulation assembly of an implantable stimulation device as described above and/or below, wherein: a material stiffness of the portion of the malleable component that is part of the intra-cochlear portion is different than a material stiffness of the portion of the malleable component that is part of the extra-cochlear portion, wherein the malleable component is a monolithic component. In an exemplary embodiment, there is an elongate stimulation assembly of an implantable stimulation device as described above and/or below, wherein: a material stiffness of the portion of the malleable component that is part of the intra-cochlear portion is different than a material stiffness of the portion of the malleable component that is part of the extra-cochlear portion, wherein the malleable component is a monolithic component and a diameter of the malleable component is uniform between the two portions.

In an exemplary embodiment, there is an elongate stimulation assembly of an implantable stimulation device, comprising: an intra-cochlear portion including an array of electrodes; and an extra-cochlear portion extending from the intra-cochlear portion, wherein a first malleable component is located in the extra-cochlear portion; and a stiffener component is located in the intra-cochlear portion, the stiffener component being separate from the first malleable component. In an exemplary embodiment, there is an elongate stimulation assembly as described above and/or below, wherein: the stiffener component is a second malleable component separate from the first malleable component. In an exemplary embodiment, there is an elongate stimulation assembly as described above and/or below, wherein: the stiffener component has a first portion located in the intra-cochlear portion and a second portion located in the extra cochlear portion. In an exemplary embodiment, there is an elongate stimulation assembly as described above and/or below, wherein: the first malleable component does not extend into the intra-cochlear portion. In an exemplary embodiment, there is an elongate stimulation assembly as described above and/or below, wherein: the first malleable component overlaps with the stiffener component in a longitudinal direction of the elongate stimulation assembly. In an exemplary embodiment, there is an elongate stimulation assembly as described above and/or below, wherein: the stiffener component is a removable stylet. In an exemplary embodiment, there is an elongate stimulation assembly as described above and/or below, further comprising: a second malleable component that is separate from the first malleable component and separate from the stiffener. In an exemplary embodiment, there is an elongate stimulation assembly as described above and/or below, wherein: the second malleable component is longitudinally spaced away from the first malleable component. In an exemplary embodiment, there is an elongate stimulation assembly as described above and/or below, wherein: the first malleable component is the only malleable component that is completely outside the intra-cochlear portion. In an exemplary embodiment, there is an elongate stimulation assembly as described above and/or below, wherein: the stiffener component is an elastic component that extends at least about half the length of the intra-cochlear portion. In an exemplary embodiment, there is an elongate stimulation assembly as described above and/or below, wherein the first malleable component is a removable component. In an exemplary embodiment, there is an elongate stimulation assembly as described above and/or below, wherein: the first malleable component is configured to have a stiffness that is adjustable at a local portion thereof. In an exemplary embodiment, there is an elongate stimulation assembly as described above and/or below, wherein: the extra-cochlear portion is configured to have a stiffness that is adjustable at a local portion thereof.

It is noted that some embodiments include a method of utilizing the apparatuses and systems having one or more or all of the teachings detailed herein and/or variations thereof. In this regard, it is noted that any disclosure of a device and/or system herein also corresponds to a disclosure of utilizing the device and/or system detailed herein, at least in a manner to exploit the functionality thereof. Further, it is noted that any disclosure of a method of manufacturing corresponds to a disclosure of a device and/or system resulting from that method of manufacturing. It is also noted that any disclosure of a device and/or system herein corresponds to a disclosure of manufacturing that device and/or system. Moreover, any disclosure of a method action herein also corresponds to a system and/or a device for executing that method action. Also, any disclosure of a device of system herein corresponds to a disclosure of a method of using that device and/or system, and a method of manipulating that device and/or system using the features disclosed herein.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An elongate stimulation assembly of an implantable stimulation device, comprising:
   an intra-cochlear portion including an array of electrodes; and
   an extra-cochlear portion extending from the intra-cochlear portion, the extra-cochlear portion including a lead assembly, wherein
   the extra-cochlear portion includes a malleable component extending in an elongate manner, a beginning of the malleable component extending from a location proximate the intra-cochlear portion to a location in the extra-cochlear portion that is less than about three-quarters the length of the elongate stimulation assembly, and
   the malleable component extends more than 20% of the length of the lead assembly.

2. The assembly of claim 1, wherein:
   the extra-cochlear portion includes a plurality of electrical lead wires in electrical communication with the array of electrodes at least a portion of the malleable component is located further away from or the same distance from a longitudinal axis of the extra-cochlear portion than a portion of least one of the electrical leads of the plurality of electrical leads.

3. The assembly of claim 2, wherein:
   the extra-cochlear portion includes a lead body; and
   the malleable component is a metal wire embedded in the lead body for a substantial length of the lead body.

4. The assembly of claim 2, wherein:
   the extra-cochlear portion includes a lead body; and
   the malleable component is a metal wire located completely outside the lead body.

5. The assembly of claim 2, wherein:
   the extra-cochlear portion includes a lead body in which are located the plurality of lead wires; and
   the malleable component establishes electrical communication with at least one electrode of the array of electrodes.

6. The assembly of claim 1, wherein:
   the elongate stimulating assembly comprises a streamlined body that is generally concentric when in a straight configuration that extends from a distal end to a proximal end thereof; and
   the malleable component extends within the streamlined body.

7. The assembly of claim 1, wherein:
   the extra-cochlear portion includes a lead body; and
   the assembly is configured such that movement of the malleable portion moves the lead body in a one-to-one manner.

8. The assembly of claim 1, wherein:
   the malleable component is located in only the extra-cochlear portion.

9. The assembly of claim 1, wherein:
   the elongate stimulating assembly includes a main body that extends from a most proximal end to a most distal end, and the main body includes the extra-cochlear portion and the intra-cochlear portion, and the extra-cochlear portion and the intra-cochlear portion are aligned along a longitudinal direction; and
   the malleable component is located in the main body in its entirety.

10. The assembly of claim 1, wherein:
    the elongate stimulating assembly extends from a proximal end to a distal end, the distal end configured to attach to a receiver apparatus of an implant, and the assembly can be positioned such that a straight axis can be within the boundaries of the elongate stimulating assembly for at least almost all of its length in its entirety; and
    the malleable component is parallel with the straight axis.

11. The assembly of claim 1, wherein:
    the extra-cochlear portion extends from a proximal end to a distal end, the distal end configured to attach to a receiver apparatus of an implant, and the assembly can be positioned such that a straight axis can be within the boundaries of the extra-cochlear portion for at least almost all of its length in its entirety; and
    the malleable component is also within the boundaries of the extra-cochlear portion that bound the straight axis.

12. The assembly of claim 1, wherein:
    the elongate stimulating assembly extends from a proximal end to a distal end, the distal end configured to attach to a receiver apparatus of an implant, and the assembly can be positioned such that a straight axis can be in the interior of the stimulating assembly for at least almost all of its length in its entirety; and
    the malleable component is parallel with the straight axis.

13. The assembly of claim 1, wherein:
    the extra-cochlear portion includes a lead body, and
    the assembly is configured such that movement of the malleable portion moves the lead body in a one-to-one manner.

14. The assembly of claim 1, further comprising:
    a second malleable component that is separate from the malleable component, wherein the elongate stimulating assembly comprises a portion that extends along a single axis from a distal end to a proximal end thereof, and the first and second malleable components are entirely within the portion.

15. An elongate stimulation assembly of an implantable stimulation device, comprising:
an intra-cochlear portion including an array of electrodes; and
an extra-cochlear portion extending from the intra-cochlear portion, wherein
the extra-cochlear portion includes a malleable component extending in an elongate manner, a beginning of the malleable component extending from a location proximate the intra-cochlear portion to a location in the extra-cochlear portion that is less than about three-quarters the length of the elongate stimulation assembly, and
most of the extra-cochlear portion is at least generally coaxial with a proximal end of the intra-cochlear portion when the stimulating assembly is held straight.

16. The assembly of claim 15, wherein:
the malleable component extends less than about half the length of the elongate stimulation assembly.

17. The assembly of claim 15, wherein:
the extra-cochlear portion includes a lead body;
a substantial length of the lead body is restrained from movement by the malleable component and a substantial length of the lead body is unrestrained from movement by the malleable component.

18. The assembly of claim 15, wherein:
the extra-cochlear portion includes a lead body; and
the malleable component is embedded in the lead body and extends for a majority of a length of the lead body in a direction away from the intra-cochlear portion.

19. The assembly of claim 15, wherein:
the elongate stimulating assembly comprises a portion that extends along a single axis from a distal end to a proximal end thereof; and
the malleable component extends parallel to the single axis.

20. The assembly of claim 15, wherein:
the elongate stimulating assembly extends from a proximal end to a distal end, the distal end configured to attach to a receiver apparatus of an implant, and the assembly can be positioned such that a straight axis can be within the boundaries of the elongate stimulating assembly for at least almost all of its length in its entirety; and
the malleable component is configured to hold at least a portion of the elongate stimulating assembly straight when the malleable portion is straight.

21. An elongate stimulation assembly of an implantable stimulation device, comprising:
an intra-cochlear portion including an array of electrodes; and
an extra-cochlear portion extending from the intra-cochlear portion, wherein
the extra-cochlear portion includes a malleable component extending in an elongate manner, a beginning of the malleable component extending from a location proximate the intra-cochlear portion to a location in the extra-cochlear portion that is less than about three-quarters the length of the elongate stimulation assembly, and
the assembly further comprises a second malleable component that is separate from the malleable component, wherein the elongate stimulating assembly comprises a portion that extends along a single axis from a distal end to a proximal end thereof, and the first and second malleable components are entirely within the portion.

22. The assembly of claim 15, wherein:
a receiver/stimulator of a cochlear implant is connected to the elongate stimulation assembly at a first location of the elongate stimulation assembly;
the assembly includes:
a first structural component located proximate the receiver/stimulator, the first structural component being configured to resist movement of at least a first portion of the elongate stimulation assembly proximate the first structural component; and
a second structural component separate from the first structural component, the second structural component is located remote from the first structural component, the second structural component being configured to resist movement of at least a second portion of the elongate stimulation assembly proximate the second structural component, wherein
the second structural component is the malleable component, and a second malleable component comprises the first structural component.

23. The assembly of claim 15, wherein:
the extra-cochlear portion includes a lead assembly; and
the malleable component extends more than 20% of the length of the lead assembly.

24. The assembly of claim 15, wherein:
the extra-cochlear portion extends from a proximal end to a distal end, the distal end configured to attach to a receiver apparatus of an implant, and the assembly can be positioned such that a straight axis can be inside all outer surfaces of the extra-cochlear portion; and
the malleable component is parallel with the straight axis.

25. The assembly of claim 15, further comprising:
a second malleable component that is separate from the malleable component, wherein the elongate stimulating assembly comprises a portion that extends along a single axis from a distal end to a proximal end thereof, and the first and second malleable components are entirely within the portion.

26. The assembly of claim 21, wherein:
the extra-cochlear portion extends from a proximal end to a distal end, the distal end configured to attach to a receiver apparatus of an implant, and the assembly can be positioned such that a straight axis can be within all boundaries of the extra-cochlear portion; and
the malleable component is parallel with the straight axis.

27. The assembly of claim 21, wherein:
the extra-cochlear portion includes a lead body; and
the malleable component is embedded in the lead body and extends for at least a portion of a length of the lead body in a direction away from the intra-cochlear portion.

28. The assembly of claim 21, wherein:
the extra-cochlear portion includes a lead body; and
at least a majority of the malleable component is co-located with the lead body.

29. The assembly of claim 21, wherein:
a receiver/stimulator of a cochlear implant is connected to the elongate stimulation assembly at a proximal end of the elongate stimulation assembly; and
the elongate stimulation assembly extends in a monoextension manner from the proximal end to a distal end of the elongate stimulation assembly; and
the malleable component extends inside the monoextension structure.

30. The assembly of claim 21, wherein:
the extra-cochlear portion extends from a proximal end to a distal end, the distal end configured to attach to a receiver apparatus of an implant, and the assembly can be positioned such that a straight axis can be inside all outer surfaces of the extra-cochlear portion;
the malleable component is parallel with the straight axis; and
the extra-cochlear portion has a smooth outside profile.

31. The assembly of claim 21, wherein:
the extra-cochlear portion includes a lead assembly; and
the malleable component extends more than 20% of the length of the lead assembly.

32. The assembly of claim 21, wherein:
the extra-cochlear portion includes a lead body, and
the assembly is configured such that movement of the malleable portion moves the lead body in a one-to-one manner.

* * * * *